(12) United States Patent
Tierney et al.

(10) Patent No.: US 11,400,257 B2
(45) Date of Patent: Aug. 2, 2022

(54) FRICTIONLESS CATHETER

(71) Applicant: Teleflex Life Sciences PTE. LTD., Singapore (SG)

(72) Inventors: Morgan Tierney, Tullamore (IE); Ronald John Kelly, Oranmore (IE); David Scully, Tullamore (IE); Aleksejus Fominas, Athlone (IE); David Rowe, Fleetwood, PA (US); Rodney W. Denlinger, Lancaster, PA (US); Adrian Mahon, Walshisland (IE)

(73) Assignee: TELEFLEX LIFE SCIENCES PTE. LTD., Singapore (SG)

( * ) Notice: Subject to any disclaimer, the term of this patent is extended or adjusted under 35 U.S.C. 154(b) by 813 days.

(21) Appl. No.: 16/189,471

(22) Filed: Nov. 13, 2018

(65) Prior Publication Data

US 2019/0143078 A1 May 16, 2019

Related U.S. Application Data

(60) Provisional application No. 62/585,357, filed on Nov. 13, 2017.

(51) Int. Cl.
 *A61M 31/00* (2006.01)
 *A61M 25/00* (2006.01)
 (Continued)

(52) U.S. Cl.
 CPC .... *A61M 25/0113* (2013.01); *A61M 25/0017* (2013.01); *A61M 25/0054* (2013.01);
 (Continued)

(58) Field of Classification Search
 CPC combination set(s) only.
 See application file for complete search history.

(56) References Cited

U.S. PATENT DOCUMENTS 3,053,257 A 9/1962 Birtwell
3,084,693 A 4/1963 Cathcart et al.
(Continued)

FOREIGN PATENT DOCUMENTS

CN 105188824 A 12/2015
CN 105792872 A 7/2016
(Continued)

OTHER PUBLICATIONS

International Preliminary Report on Patentability and Written Opinion issued in PCT/IB2018/058932, dated May 28, 2020.
(Continued)

*Primary Examiner* — Tatyana Zalukaeva
*Assistant Examiner* — Ilya Y Treyger
(74) *Attorney, Agent, or Firm* — BakerHostetler

(57) ABSTRACT

A catheter may include a tubular member having a lumen and an outer surface, a sleeve configured to be positioned in the lumen in a retracted configuration and to evert over at least a portion of the outer surface in an everted configuration, and a filament configured to retract the sleeve into the retracted configuration. The catheter may include an aperture proximal of a distal end, where the filament extends through the aperture from the lumen. A pull member may be on a distal end of the filament. The filament may be looped, coiled, and/or bunched in the catheter when the sleeve is in the retracted configuration. A shuttle may be attached to a distal end of the sleeve, where the shuttle includes a tubular member configured to maintain patency of the sleeve, and the filament engages the shuttle to retract the sleeve into the lumen.

26 Claims, 43 Drawing Sheets

(51) Int. Cl.
  *A61M 25/01* (2006.01)
  *A61M 1/00* (2006.01)
  *A61M 27/00* (2006.01)
  *A61M 25/06* (2006.01)

(52) U.S. Cl.
  CPC ..... *A61M 25/0111* (2013.01); *A61M 25/0133* (2013.01); *A61M 25/002* (2013.01); *A61M 25/0119* (2013.01); *A61M 2025/0163* (2013.01); *A61M 2025/0175* (2013.01); *A61M 2025/0681* (2013.01); *A61M 2210/1089* (2013.01)

(56) References Cited

U.S. PATENT DOCUMENTS

| | | | |
|---|---|---|---|
| 3,168,092 A | 2/1965 | Silverman |
| 3,332,424 A | 7/1967 | Minteer |
| 3,421,509 A | 1/1969 | Fiore |
| 3,500,819 A | 3/1970 | Silverman |
| 3,583,391 A | 6/1971 | Cox et al. |
| 3,894,540 A | 7/1975 | Bonner, Jr. |
| 3,908,635 A | 9/1975 | Viek |
| 3,908,663 A | 9/1975 | Viek |
| 3,911,927 A | 10/1975 | Rich et al. |
| 4,170,996 A | 10/1979 | Wu |
| 4,321,915 A | 3/1982 | Leighton et al. |
| 4,540,409 A | 9/1985 | Nystrom et al. |
| 4,652,259 A | 3/1987 | O'Neil |
| 4,946,440 A | 8/1990 | Hall |
| 4,955,858 A | 9/1990 | Drews |
| 5,171,305 A | 12/1992 | Schickling et al. |
| 5,389,089 A | 2/1995 | Bauer et al. |
| 5,417,666 A | 5/1995 | Coulter |
| 5,454,795 A | 10/1995 | Samson |
| 5,531,717 A | 7/1996 | Feliziani et al. |
| 5,711,841 A | 1/1998 | Jaker |
| 5,779,670 A | 7/1998 | Bidwell et al. |
| 5,792,114 A | 8/1998 | Fiore |
| 5,897,535 A | 4/1999 | Feliziani et al. |
| 5,902,286 A | 5/1999 | Reitz |
| 5,989,241 A | 11/1999 | Plishka et al. |
| 6,007,521 A | 12/1999 | Bidwell et al. |
| 6,217,569 B1 | 4/2001 | Fiore |
| 6,286,555 B1 | 9/2001 | Pauker et al. |
| 6,585,721 B2 | 7/2003 | Fiore |
| 7,255,687 B2 | 8/2007 | Huang et al. |
| 7,380,658 B2 | 6/2008 | Murray et al. |
| 7,537,589 B2 | 5/2009 | Tsukada et al. |
| 7,601,158 B2 | 10/2009 | House |
| 7,789,873 B2 | 9/2010 | Kubalak et al. |
| 7,938,807 B2 | 5/2011 | House |
| 7,938,838 B2 | 5/2011 | House |
| 7,967,798 B2 | 6/2011 | Reydel et al. |
| 8,326,437 B2 | 12/2012 | Cully et al. |
| 8,414,562 B2 | 4/2013 | House |
| 8,529,549 B2 | 9/2013 | Tanghoj et al. |
| 8,771,286 B2 | 7/2014 | House |
| 8,845,620 B2 | 9/2014 | House |
| 8,888,747 B2 | 11/2014 | House |
| 8,894,563 B2 | 11/2014 | Connors et al. |
| 8,932,262 B2 | 1/2015 | Ostfeld et al. |
| 8,986,286 B2 | 3/2015 | Tanghoej et al. |
| 9,079,006 B1 | 7/2015 | Ovcharchyn et al. |
| 9,138,510 B2 | 9/2015 | Madsen |
| 9,168,354 B2 | 10/2015 | Hannon et al. |
| 9,649,472 B2 | 5/2017 | Kearns et al. |
| 9,661,992 B2 | 5/2017 | Lerner et al. |
| 9,789,284 B2 | 10/2017 | Nickel |
| 9,821,142 B2 | 11/2017 | Hannon et al. |
| 9,925,355 B2 | 3/2018 | Foley et al. |
| 9,931,486 B2 | 4/2018 | Schertiger et al. |
| 10,118,019 B2 | 11/2018 | Murray et al. |
| 10,406,322 B2 | 9/2019 | O'Flynn et al. |
| 10,434,282 B2 | 10/2019 | Kearns et al. |
| 10,758,704 B2 | 9/2020 | Hickmott et al. |
| 10,912,917 B2 | 2/2021 | Terry |
| 2004/0073194 A1 | 4/2004 | Olsen et al. |
| 2005/0197627 A1 | 9/2005 | Huang et al. |
| 2005/0245876 A1 | 11/2005 | Khosravi et al. |
| 2006/0178722 A1 | 8/2006 | Jaker et al. |
| 2007/0073107 A1 | 3/2007 | Peartree et al. |
| 2007/0106233 A1 | 5/2007 | Huang et al. |
| 2008/0171991 A1 | 7/2008 | Kourakis |
| 2008/0172037 A1 | 7/2008 | Huang et al. |
| 2011/0098682 A1 | 4/2011 | Ahmed et al. |
| 2011/0098689 A1 | 4/2011 | Nau, Jr. et al. |
| 2011/0114520 A1 | 5/2011 | Matthison-Hansen |
| 2011/0190736 A1 | 8/2011 | Young et al. |
| 2015/0105756 A1 | 4/2015 | O'Brien et al. |
| 2015/0133727 A1 | 5/2015 | Bacich et al. |
| 2015/0272735 A1 | 10/2015 | Kaufmann |
| 2015/0273183 A1 | 10/2015 | Foley et al. |
| 2015/0297863 A1 | 10/2015 | Hannon et al. |
| 2015/0352329 A1 | 12/2015 | Watanabe |
| 2016/0175570 A1 | 6/2016 | Nickel |
| 2016/0213459 A1 | 7/2016 | Janardhan et al. |
| 2016/0235934 A1 | 8/2016 | Poulsen et al. |
| 2016/0346108 A1 | 12/2016 | Arnault De La Menardiere et al. |
| 2017/0000978 A1 | 1/2017 | Murray et al. |
| 2017/0056622 A1 | 3/2017 | O'Flynn et al. |
| 2017/0368232 A1 | 12/2017 | Montes de Oca |
| 2020/0222659 A1 | 7/2020 | Schertiger et al. |

FOREIGN PATENT DOCUMENTS

| | | |
|---|---|---|
| CN | 206285332 U | 6/2017 |
| JP | 7-308383 A | 11/1995 |
| JP | 6386858 B2 | 9/2018 |
| WO | 8705523 A1 | 9/1987 |
| WO | 9624403 A1 | 8/1996 |
| WO | 2014/074147 A1 | 5/2014 |
| WO | 2014173046 A1 | 10/2014 |
| WO | 2018041903 A1 | 3/2018 |

OTHER PUBLICATIONS

International Search Report and Written Opinion issued in PCT/IB2018/058932, dated Feb. 22, 2019.

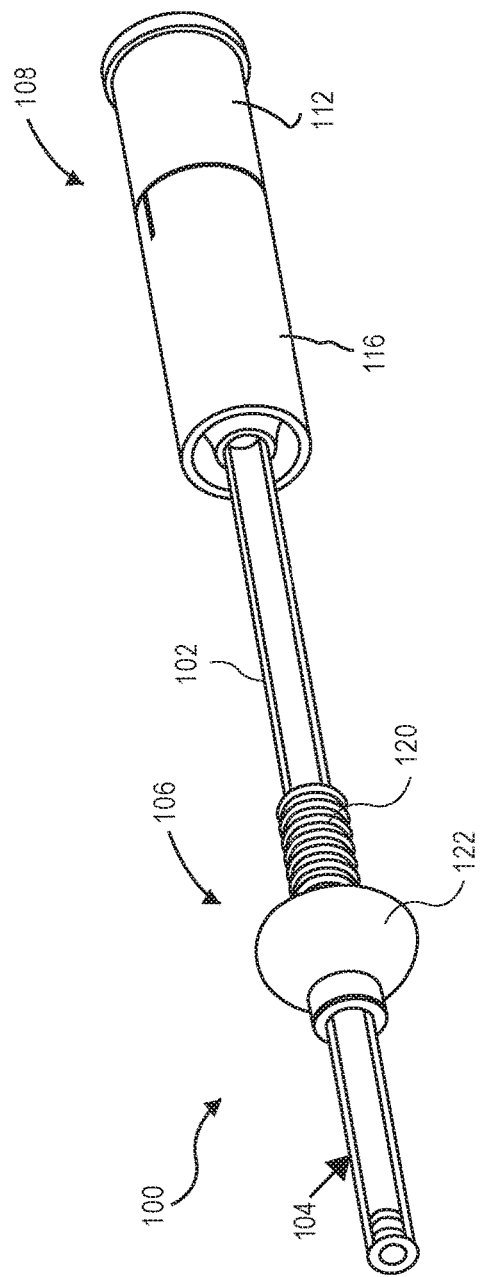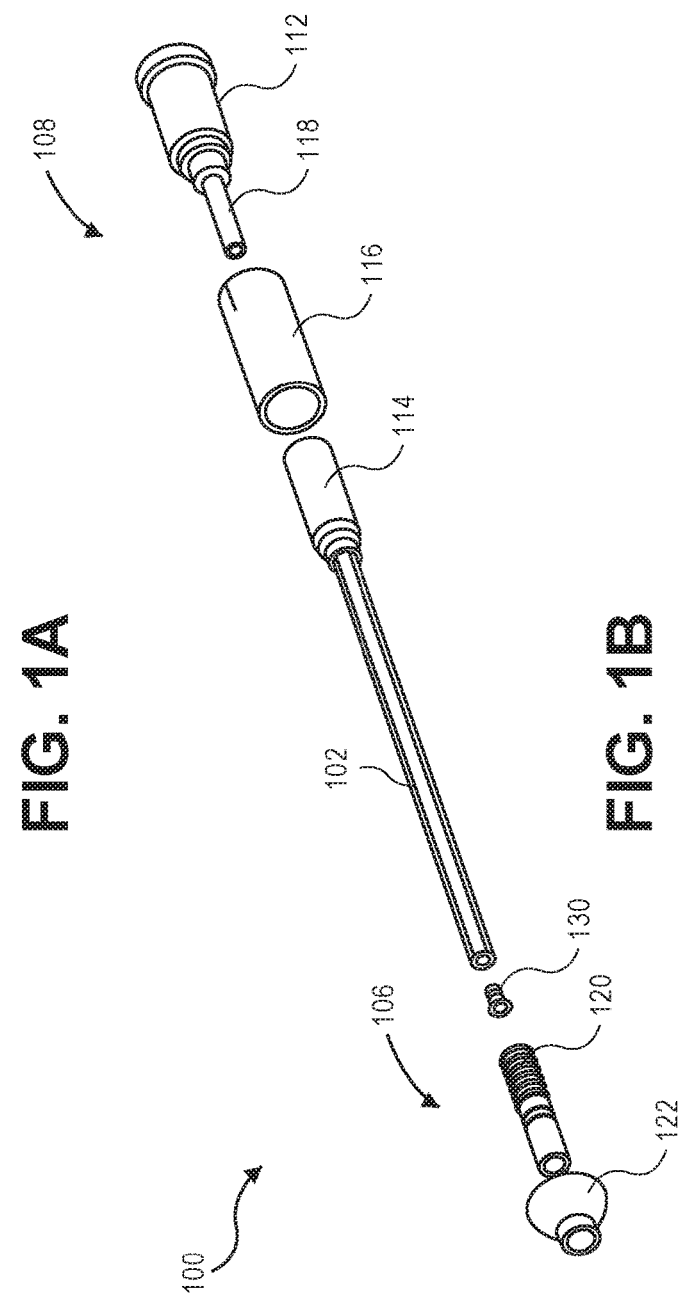
FIG. 1A
FIG. 1B

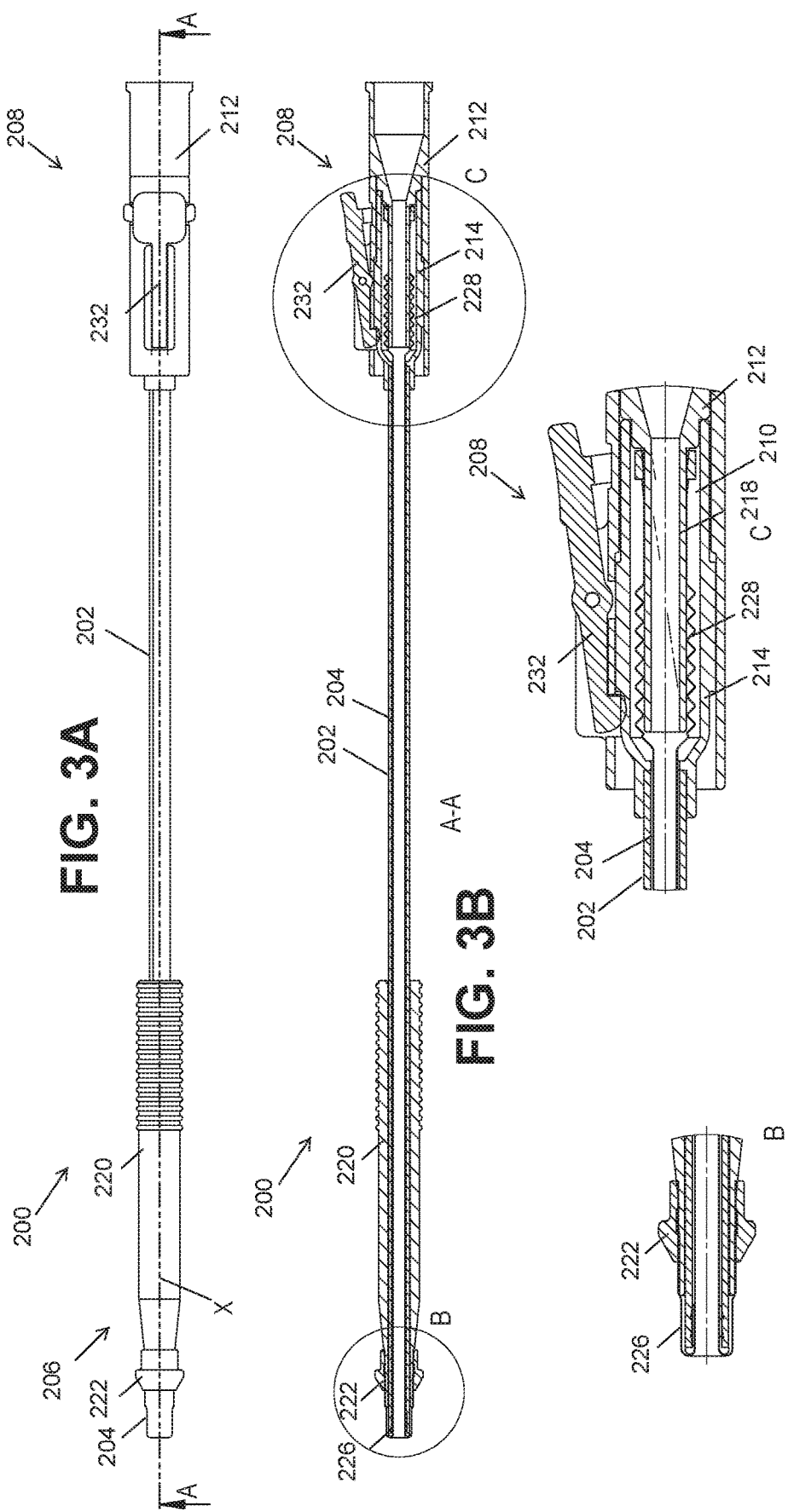

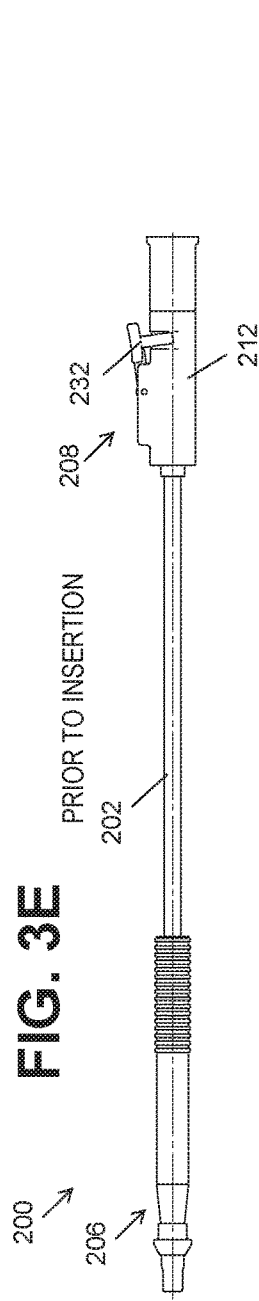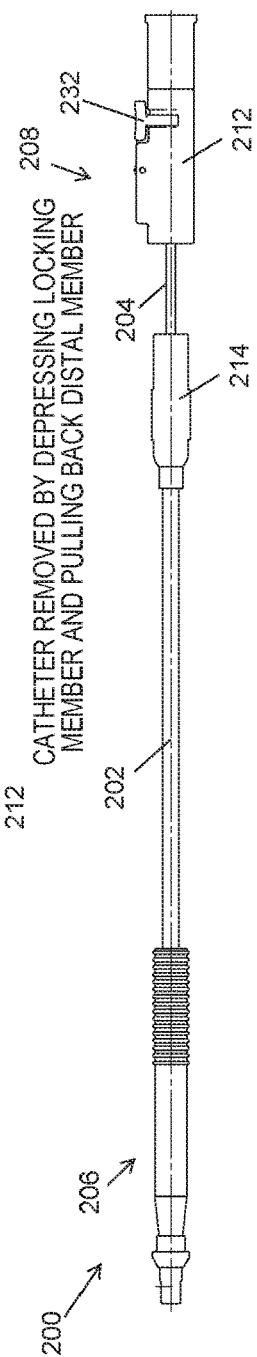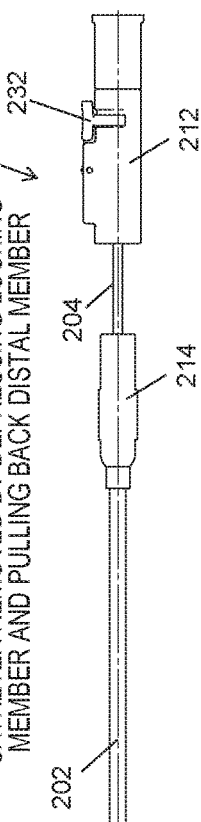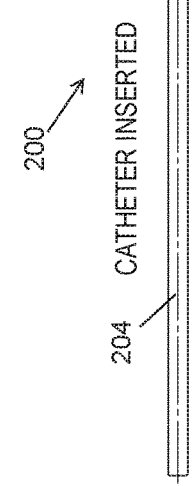

CATHETER INSERTED

D-D

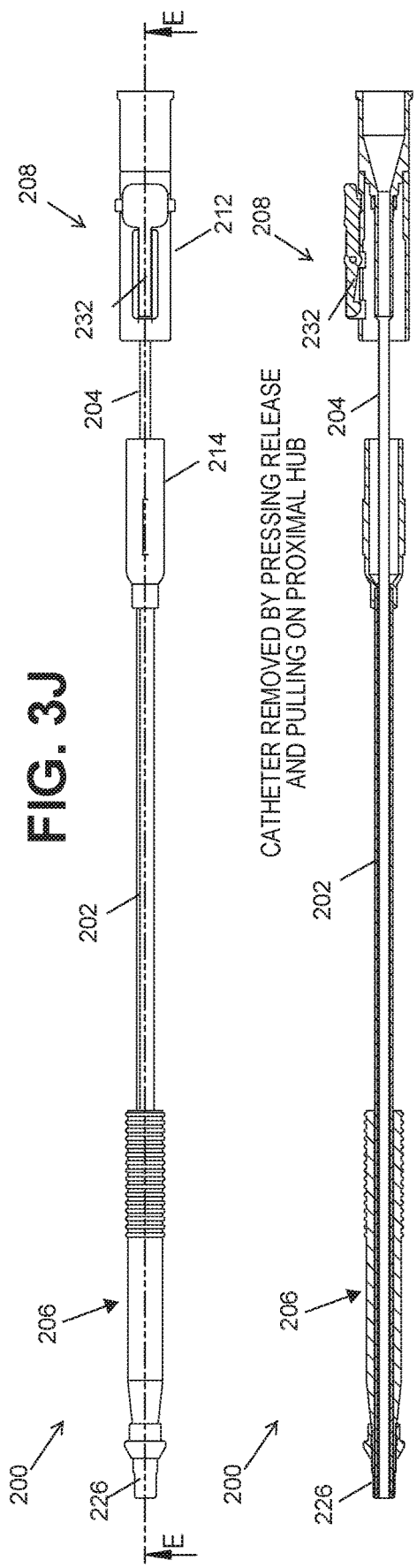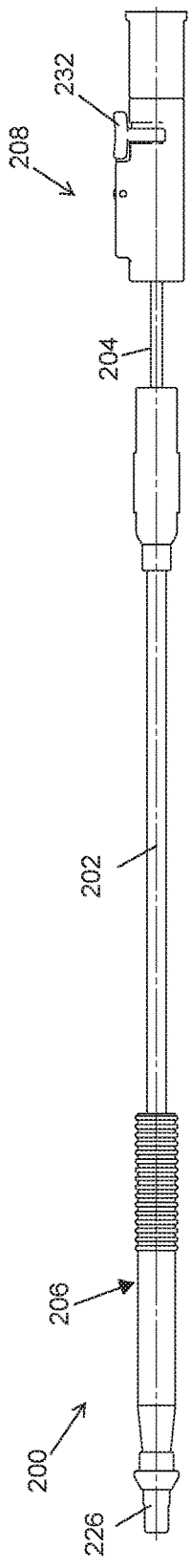

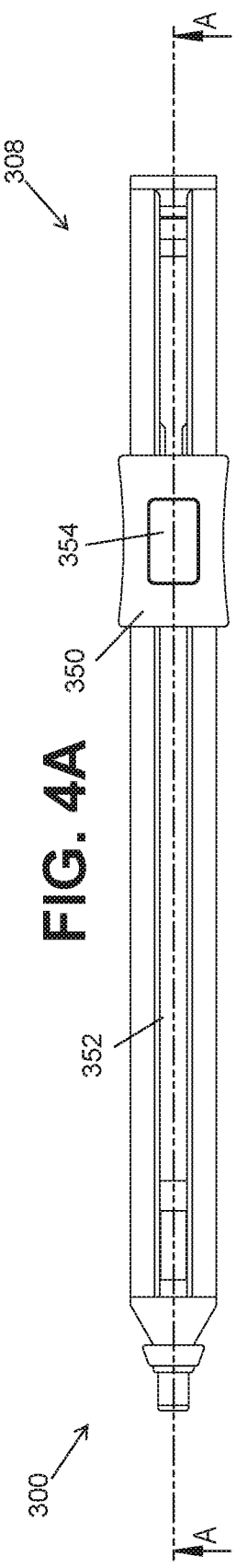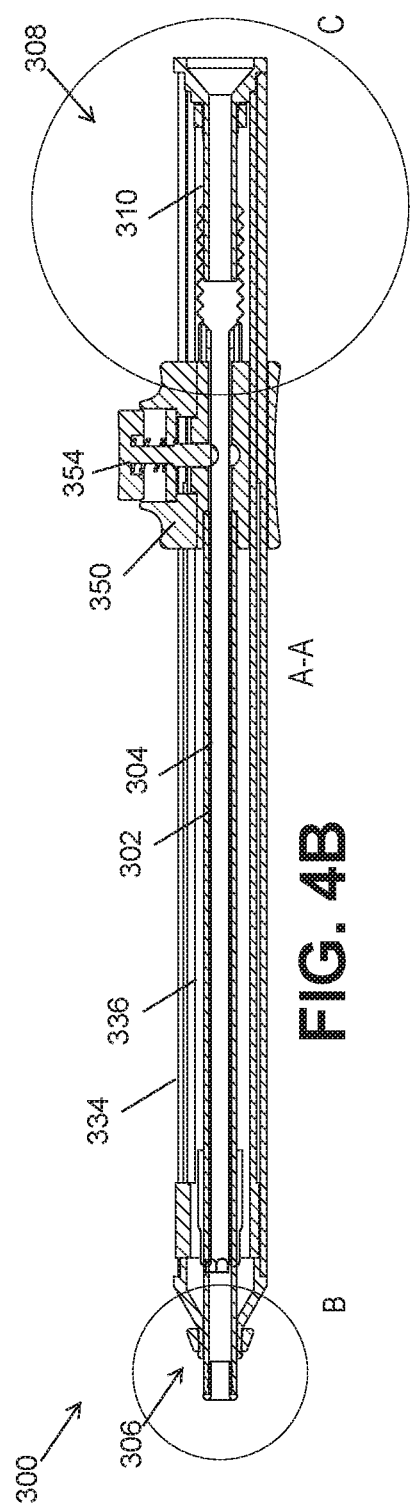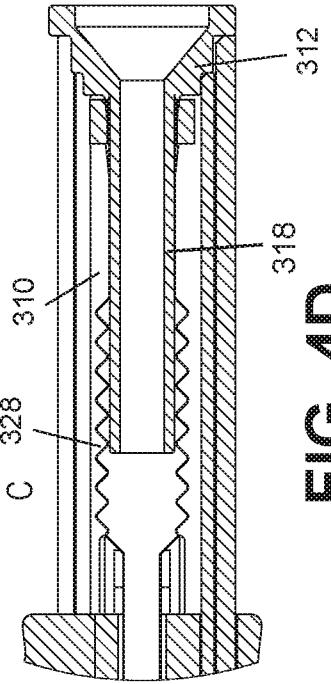

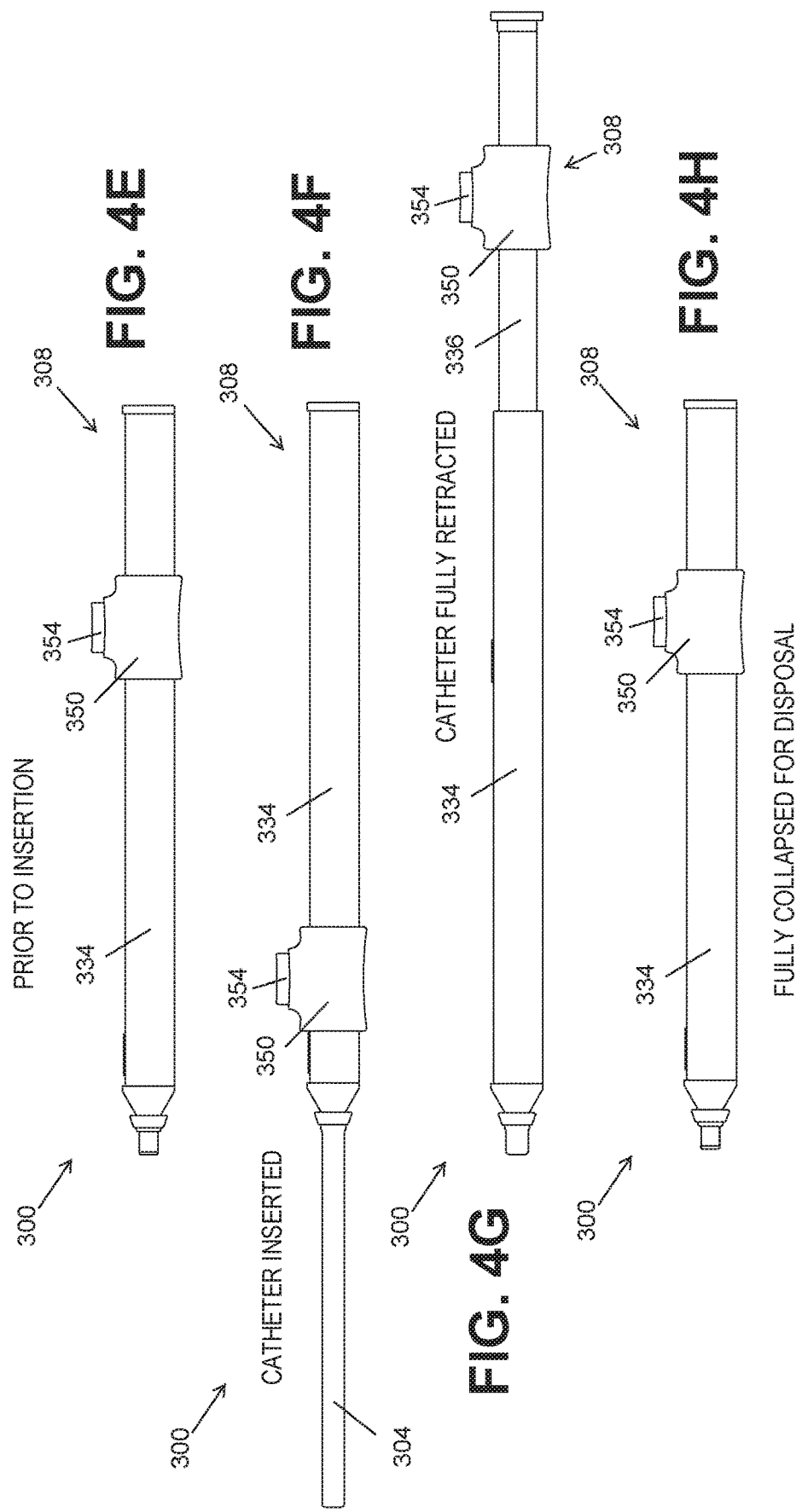

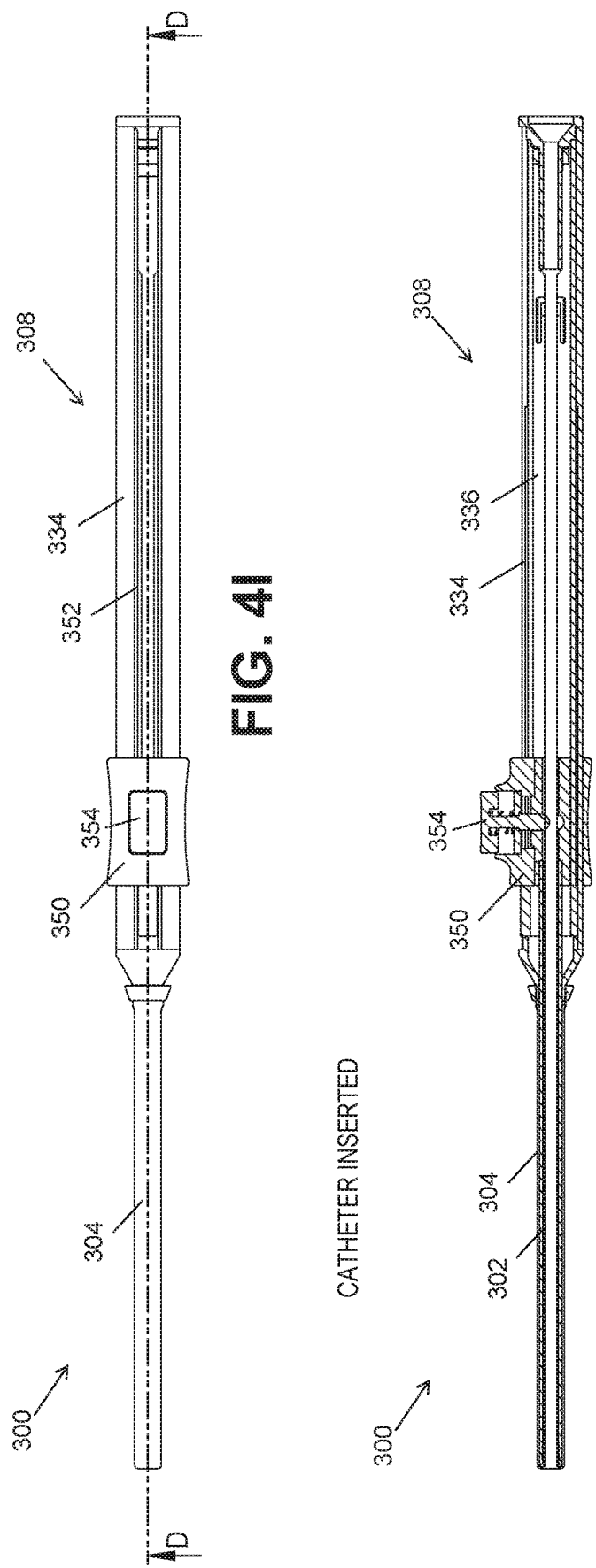

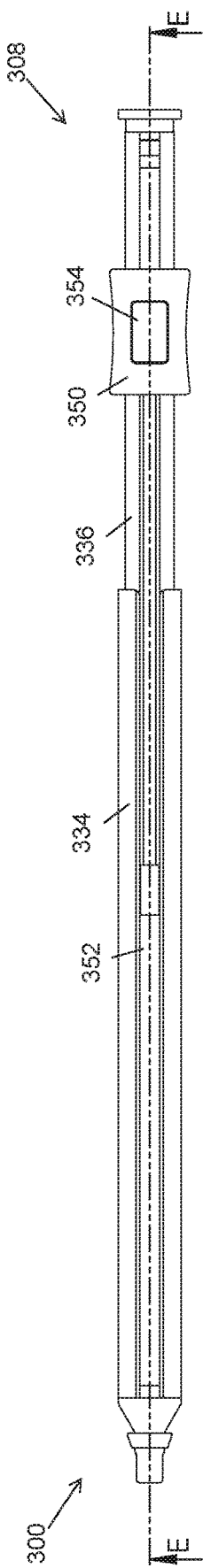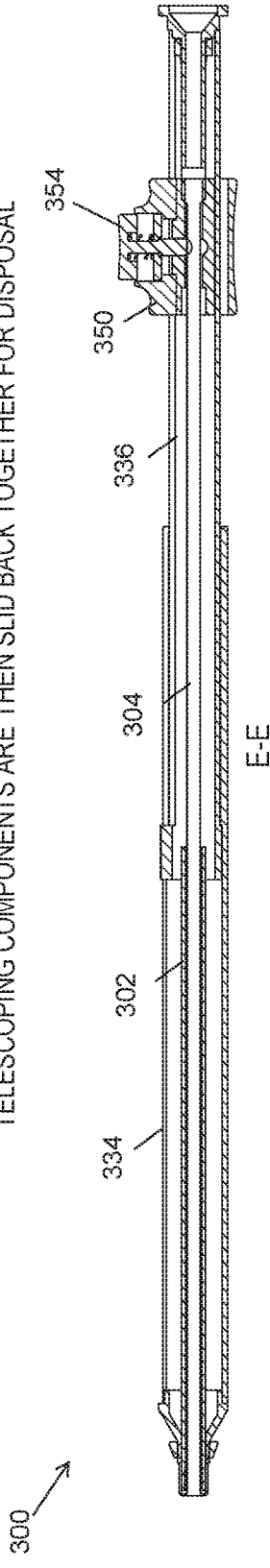

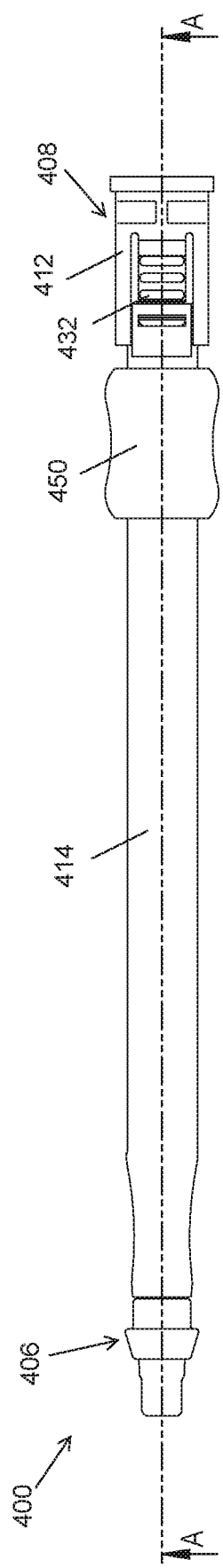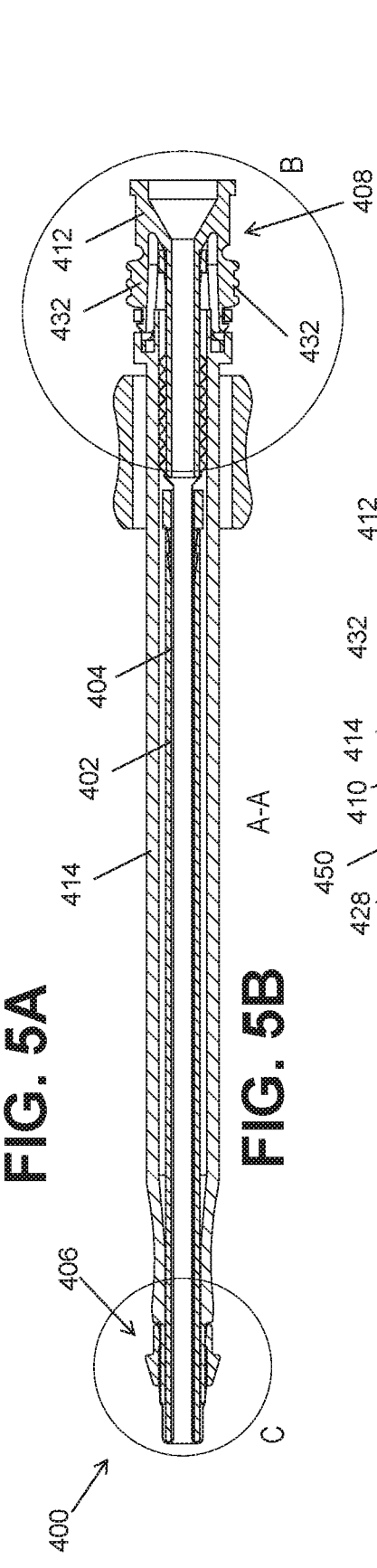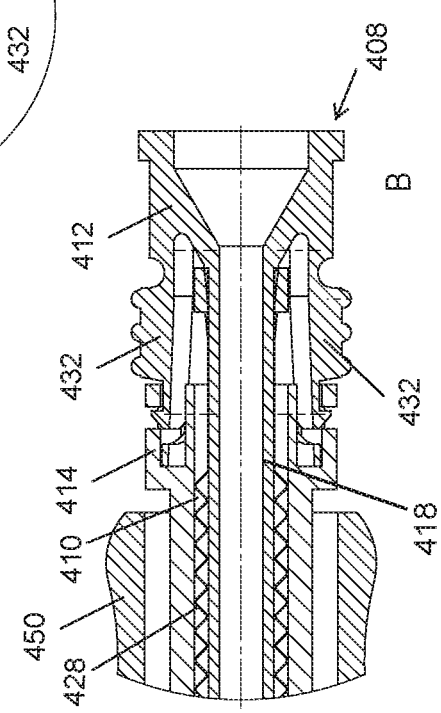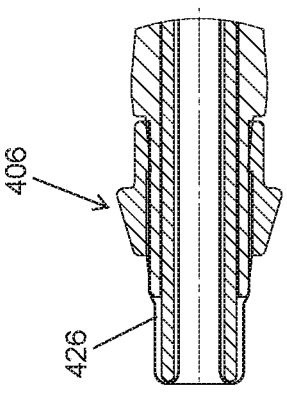
FIG. 5A
FIG. 5B
FIG. 5D
FIG. 5C

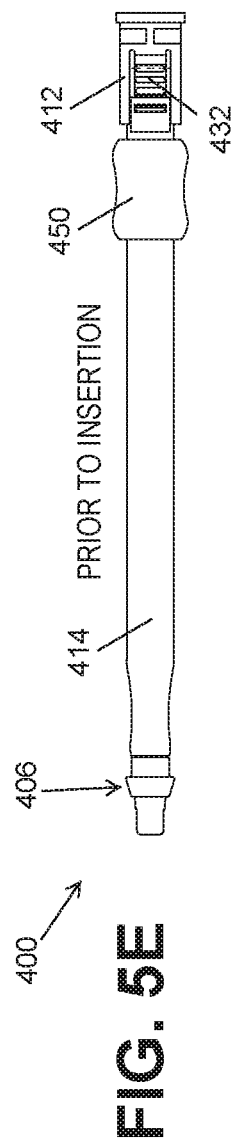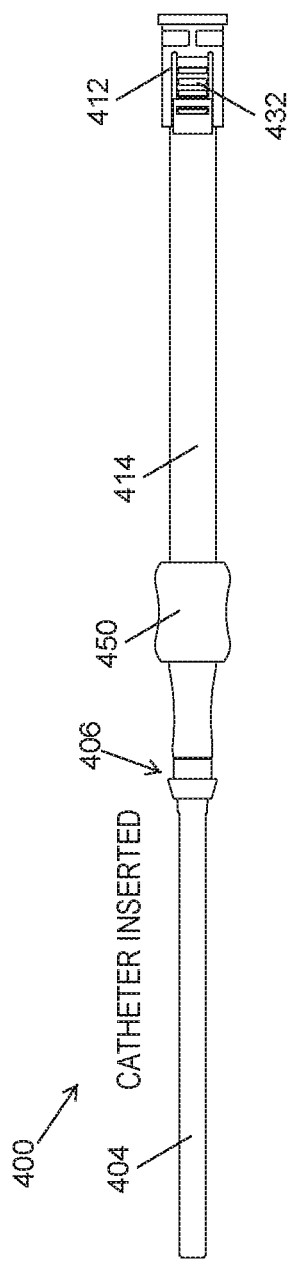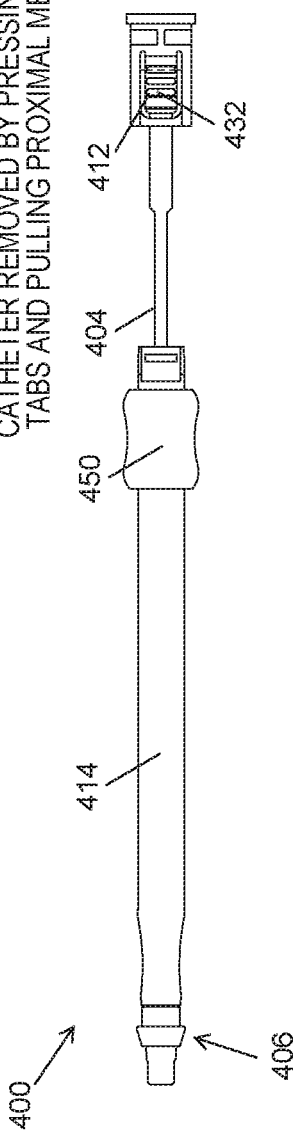

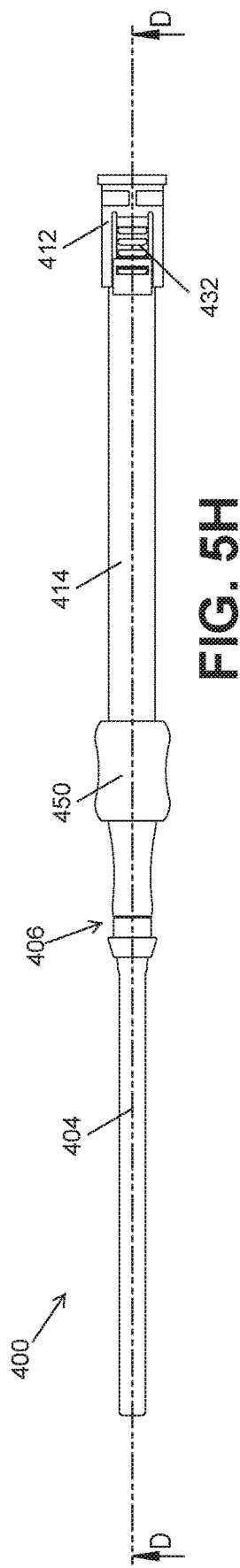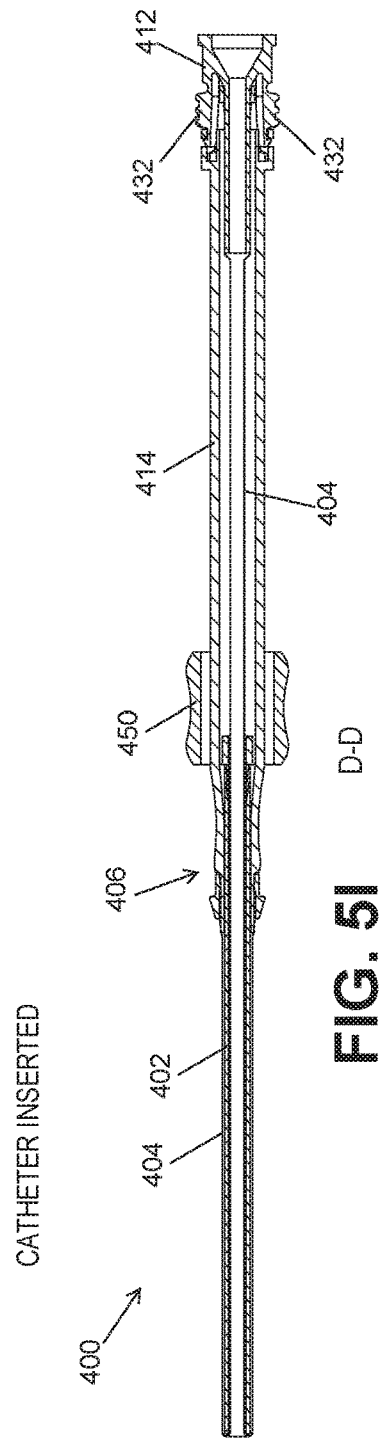

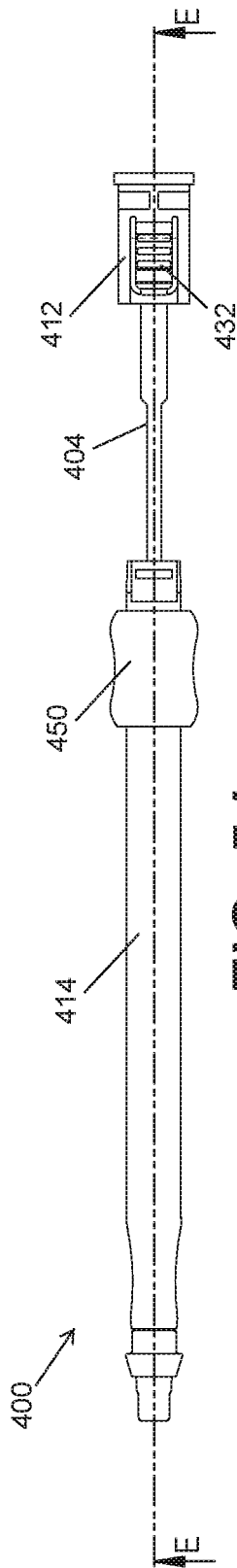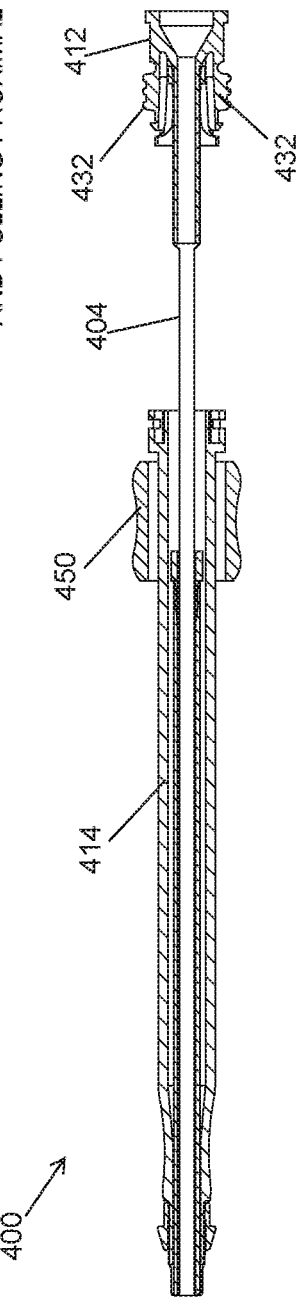

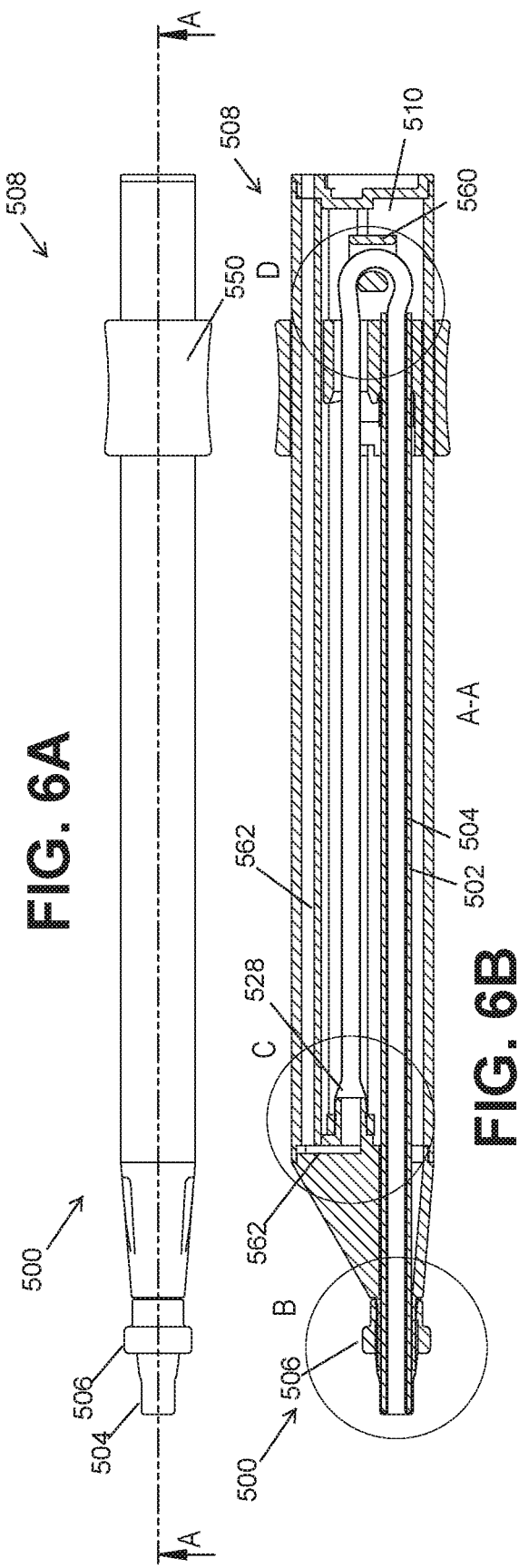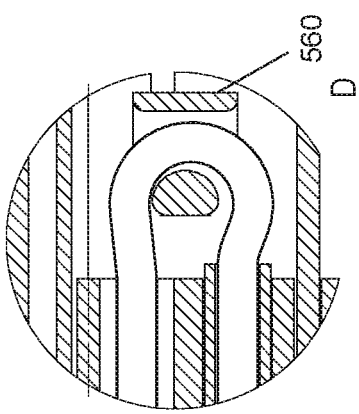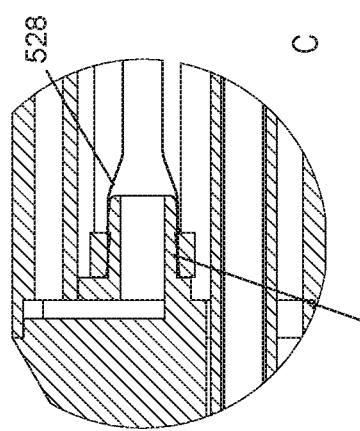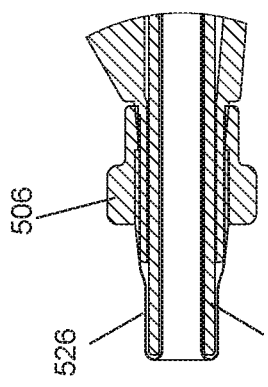

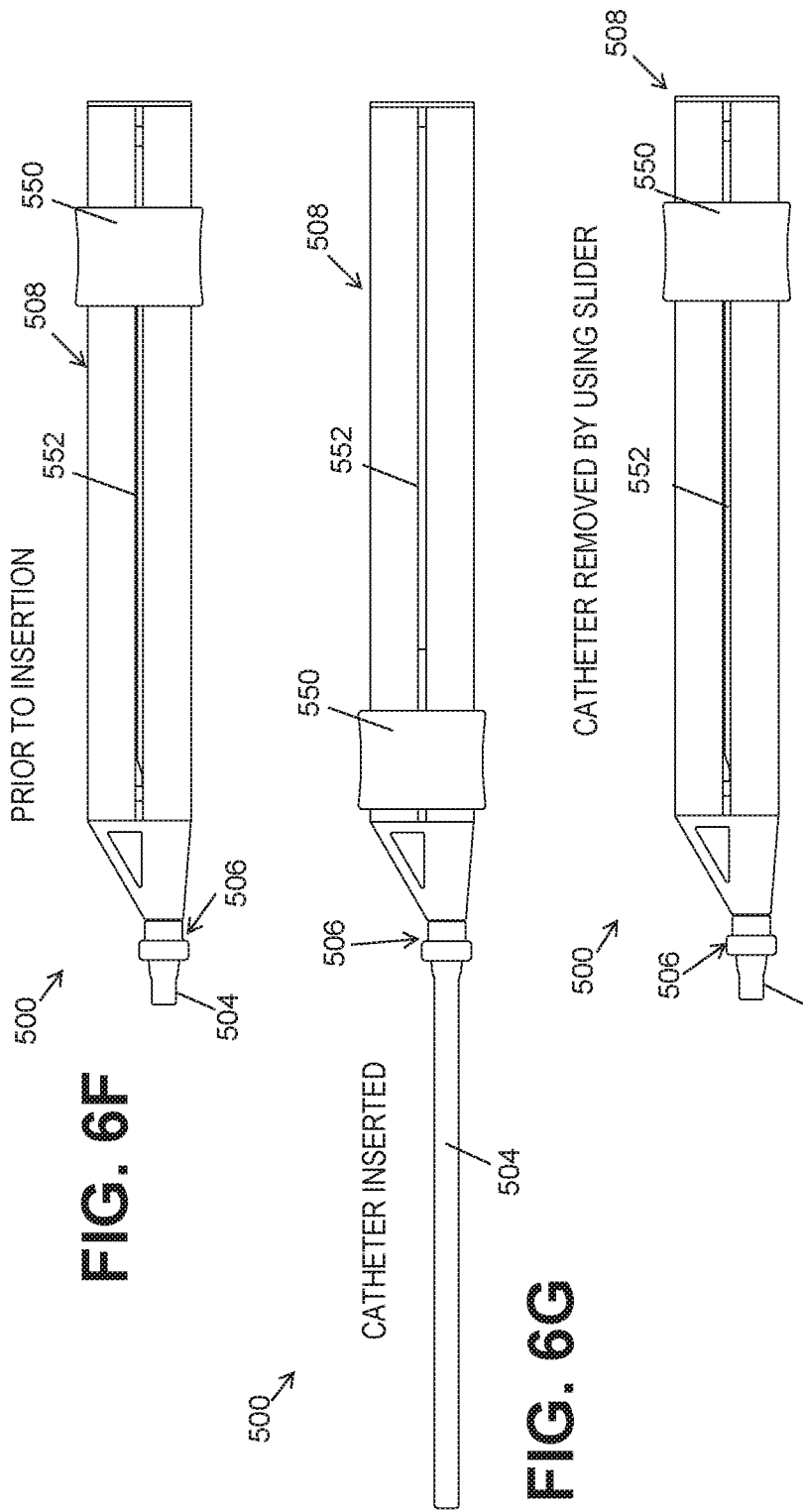

CATHETER INSERTED

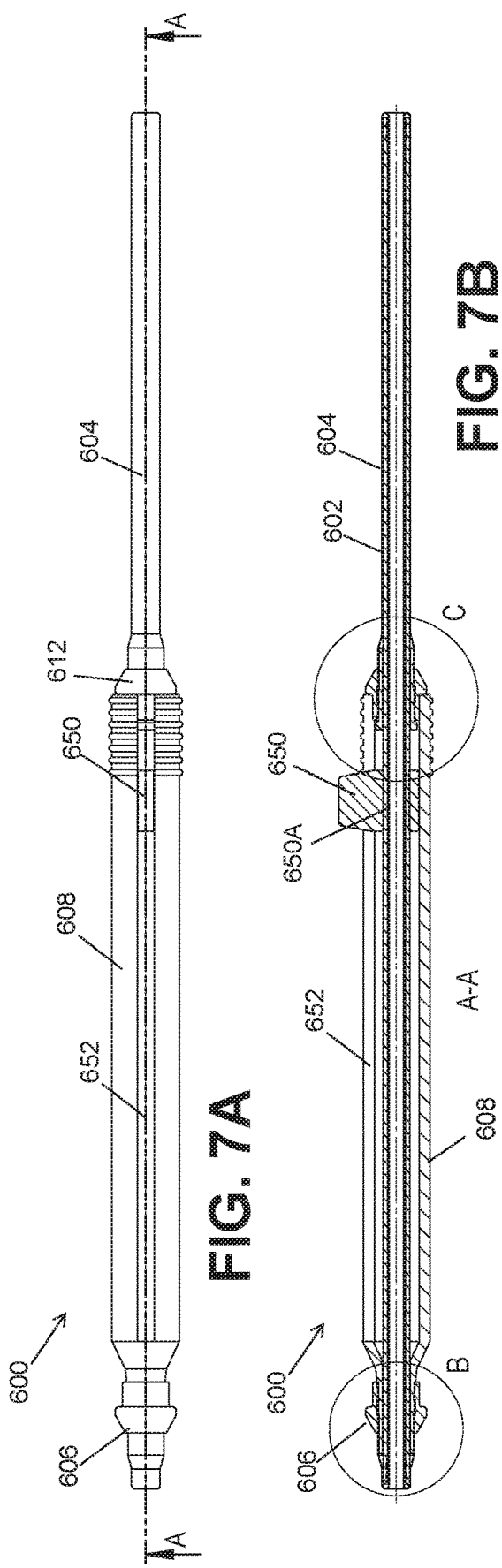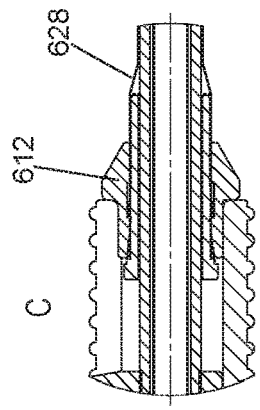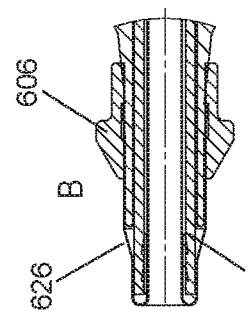

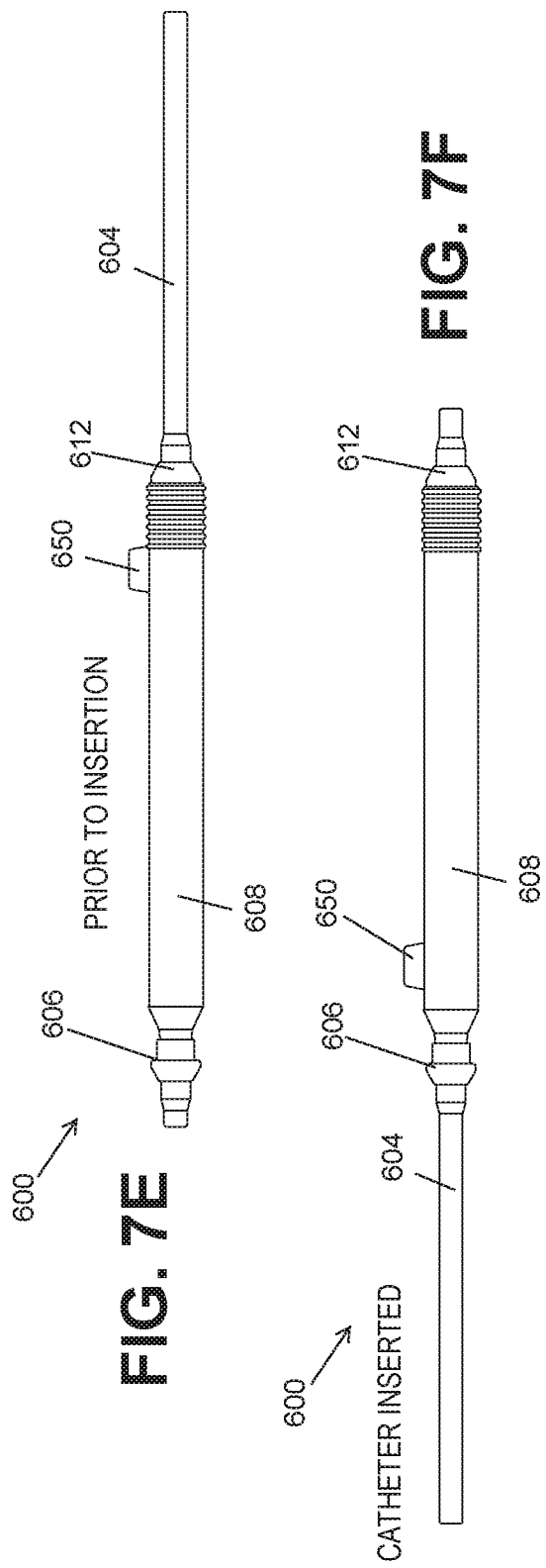

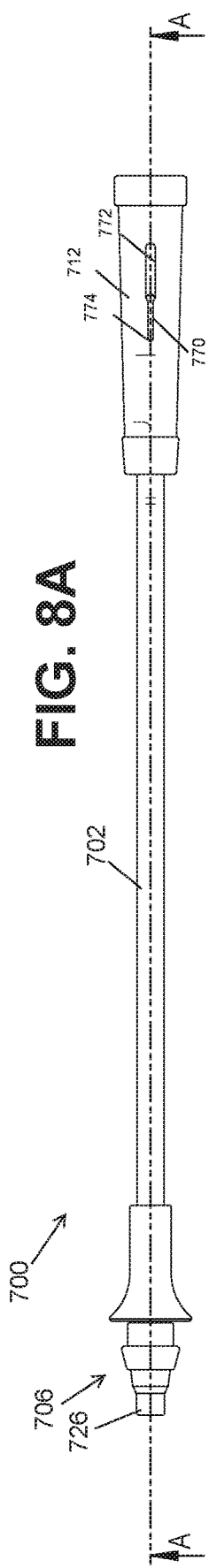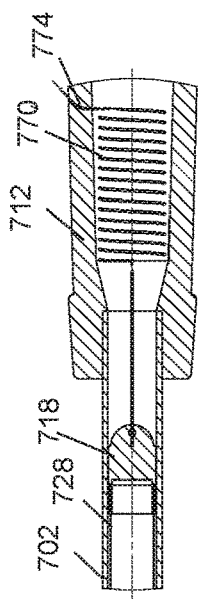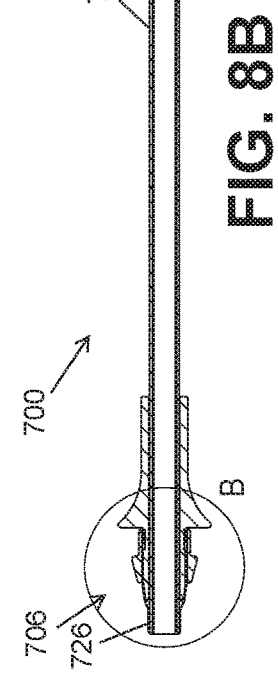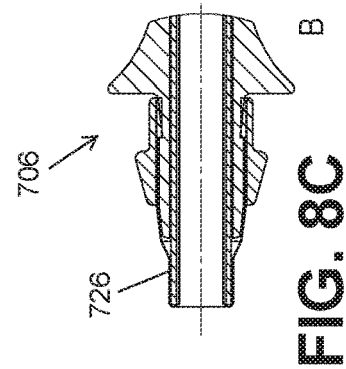
FIG. 8A
FIG. 8B
FIG. 8C
FIG. 8D

PRIOR TO INSERTION

CATHETER INSERTED

CATHETER REMOVED BY PULLING FILAMENT WITH PULL MEMBER

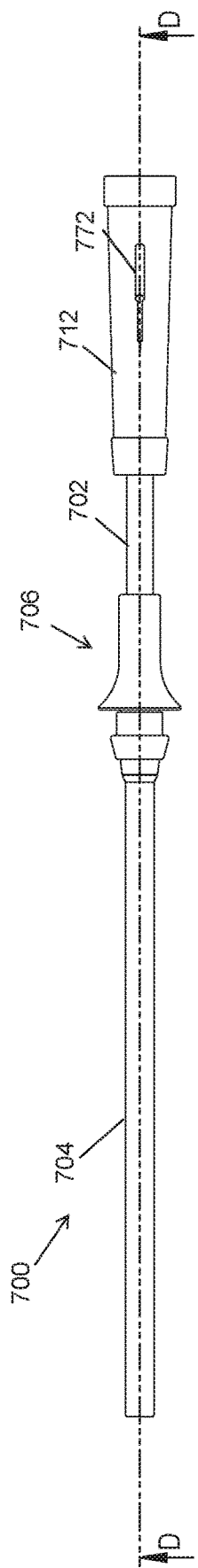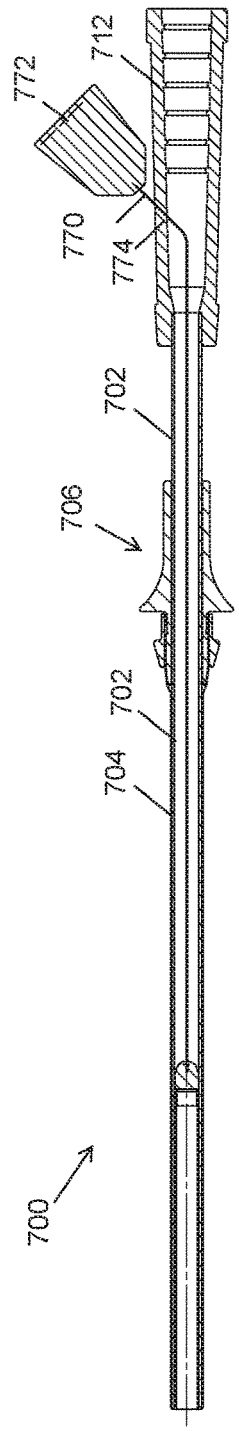
FIG. 8H
CATHETER INSERTED
FIG. 8I

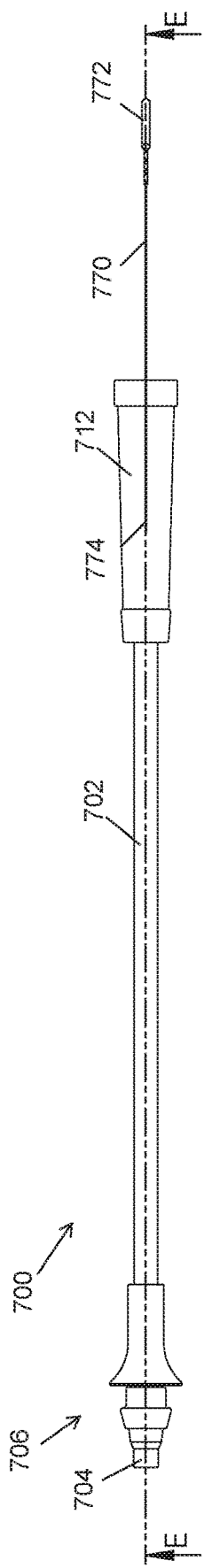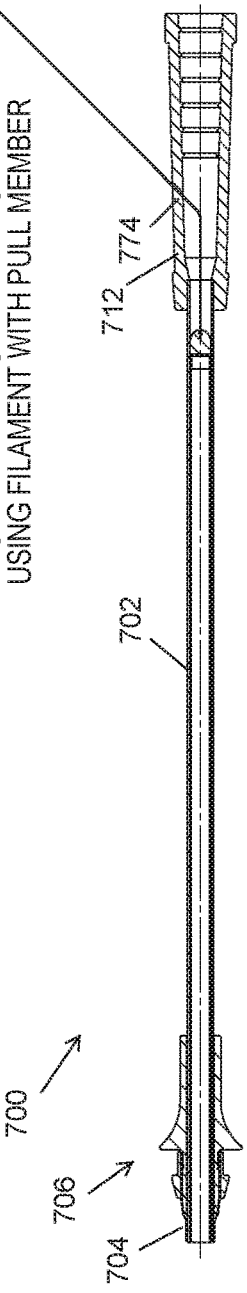

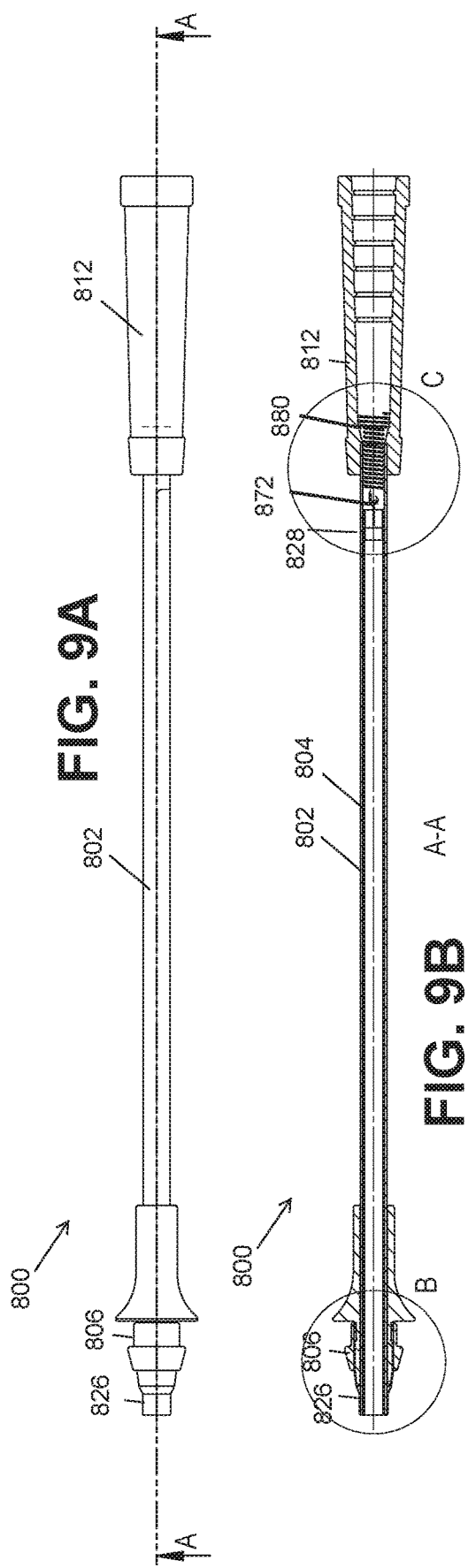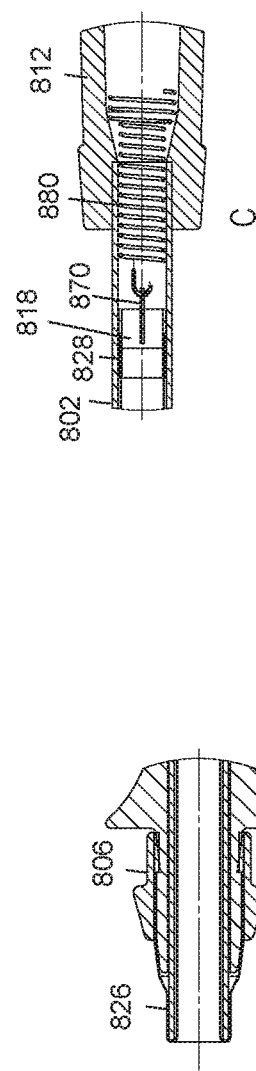

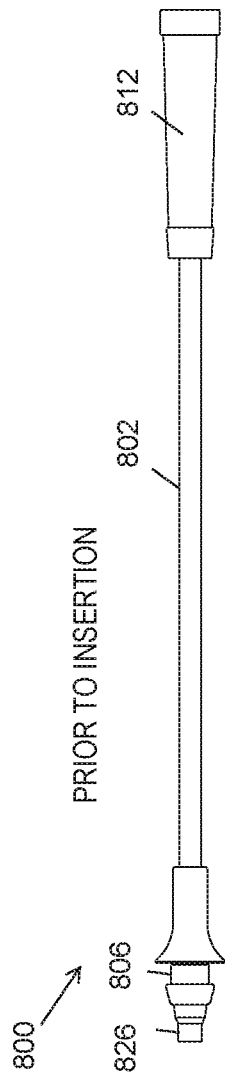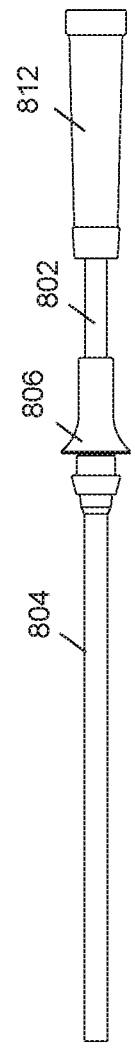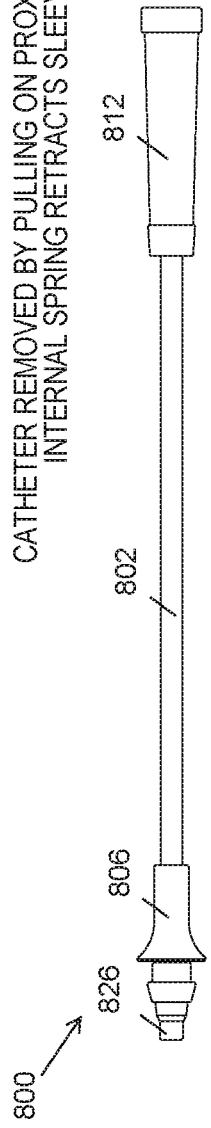
FIG. 9E — PRIOR TO INSERTION
FIG. 9F — CATHETER INSERTED
FIG. 9G — CATHETER REMOVED BY PULLING ON PROXIMAL HUB INTERNAL SPRING RETRACTS SLEEVE

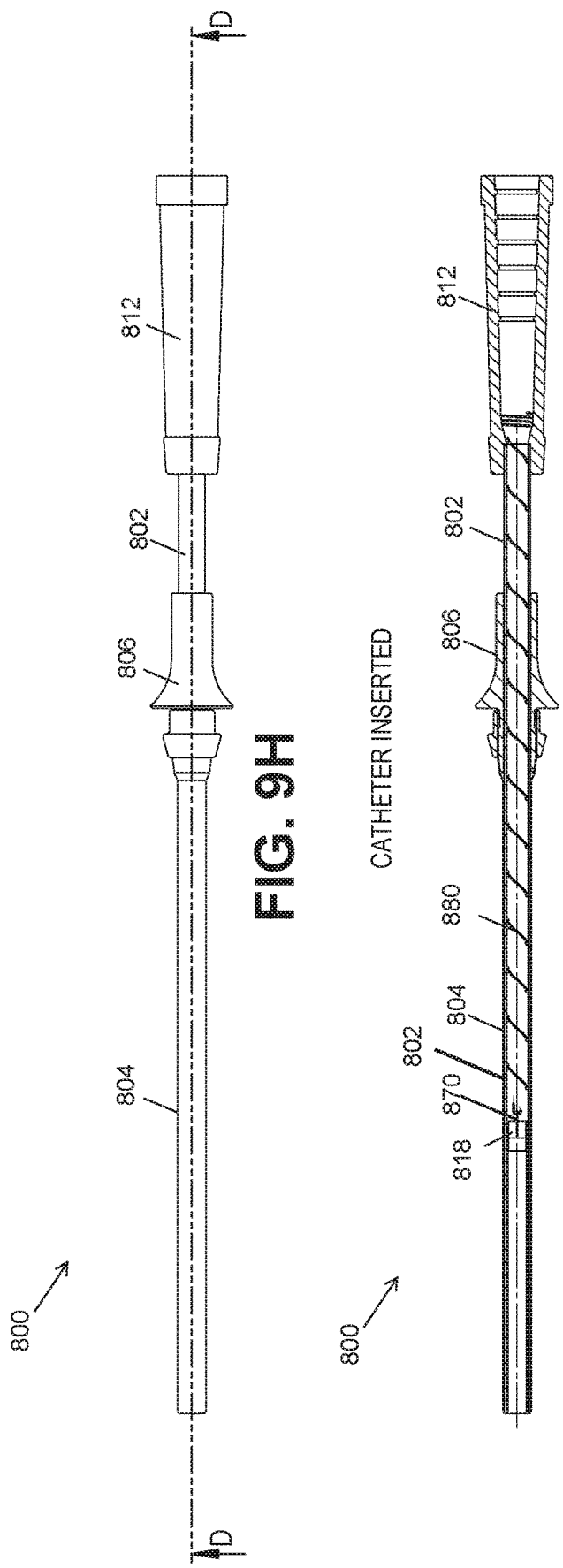

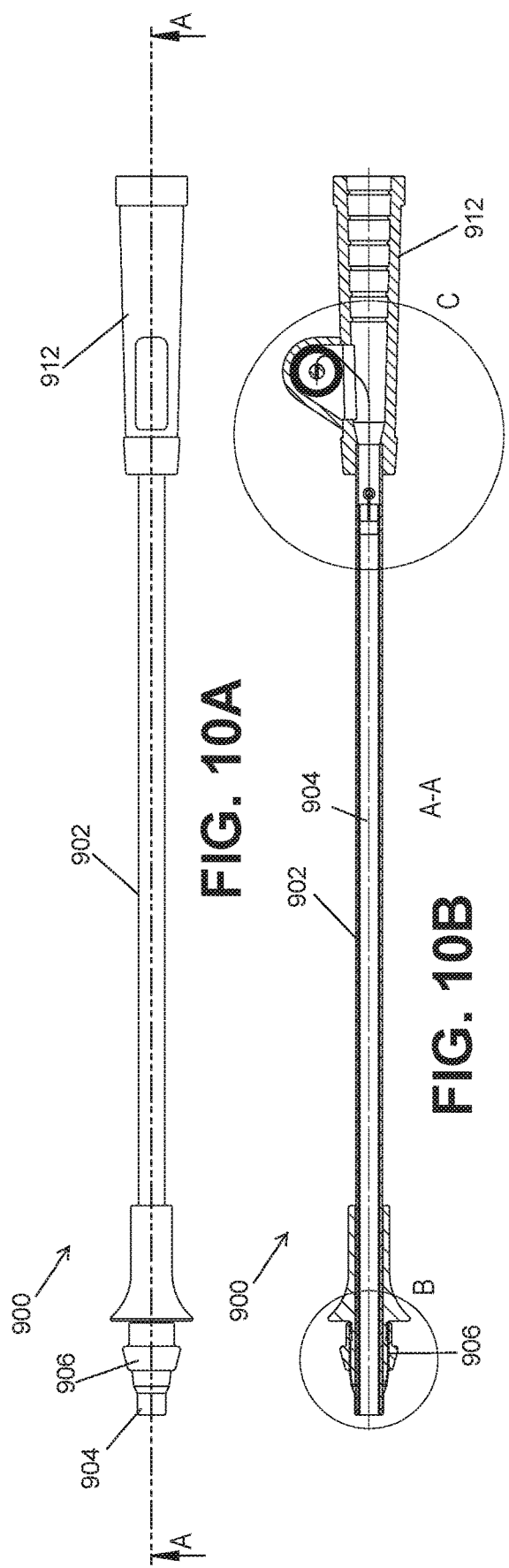

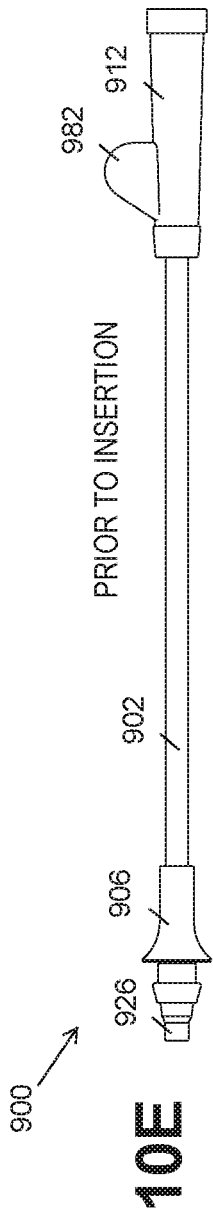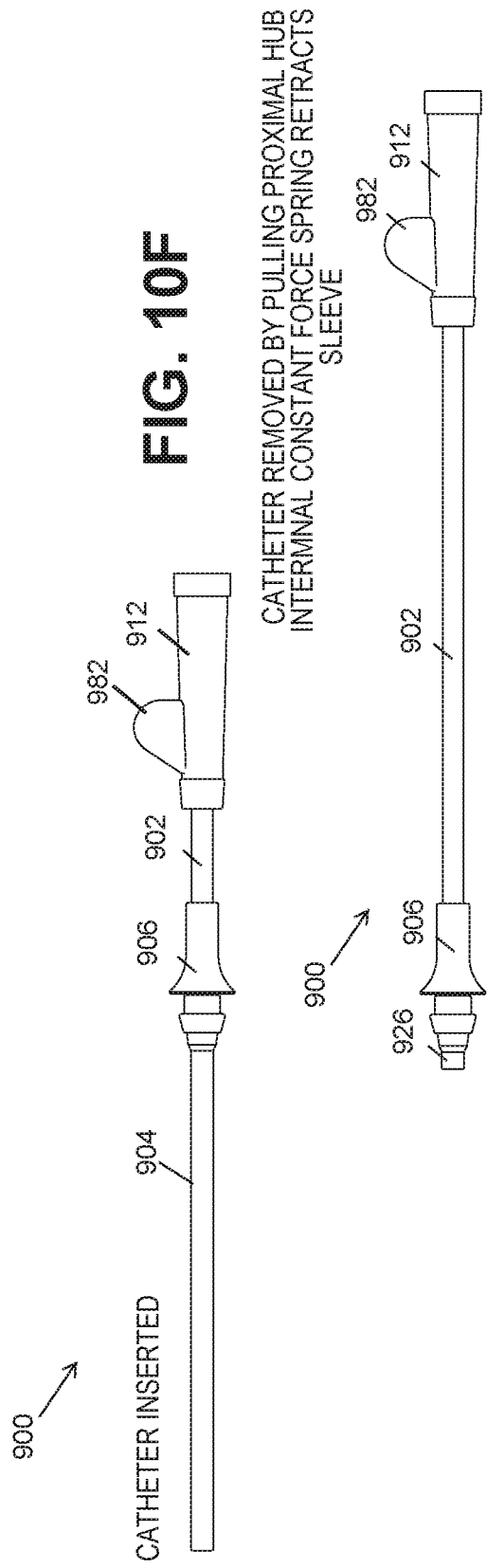

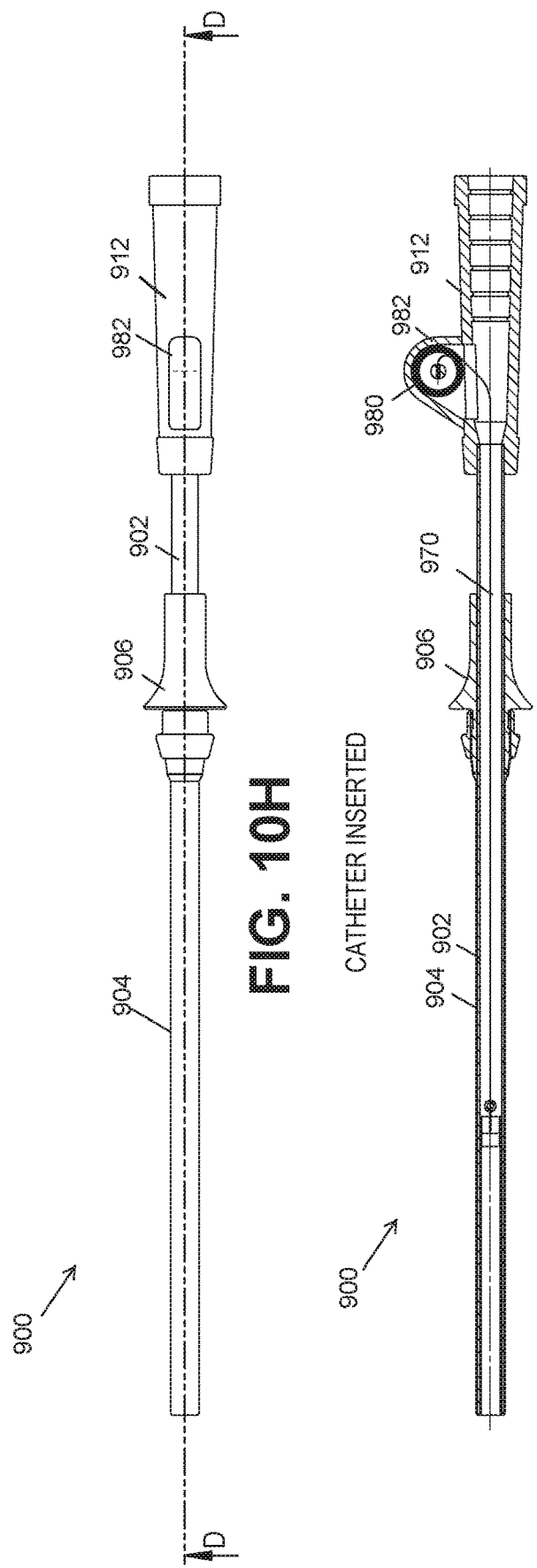

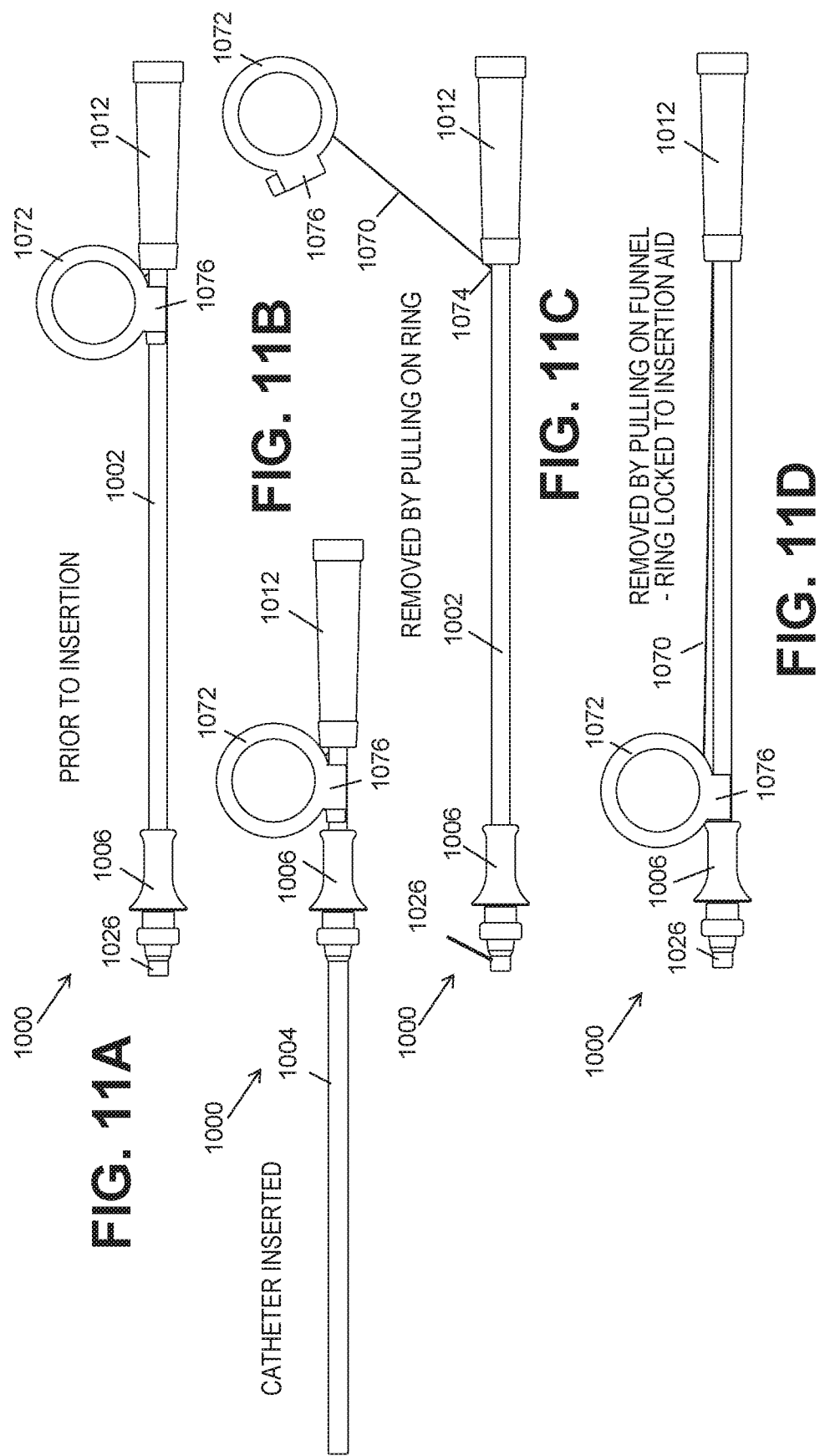

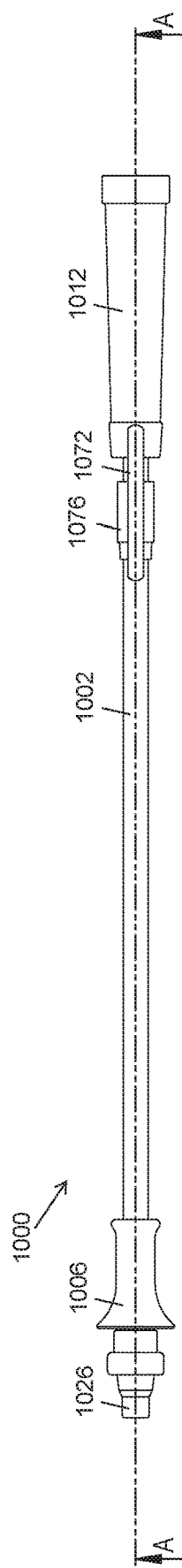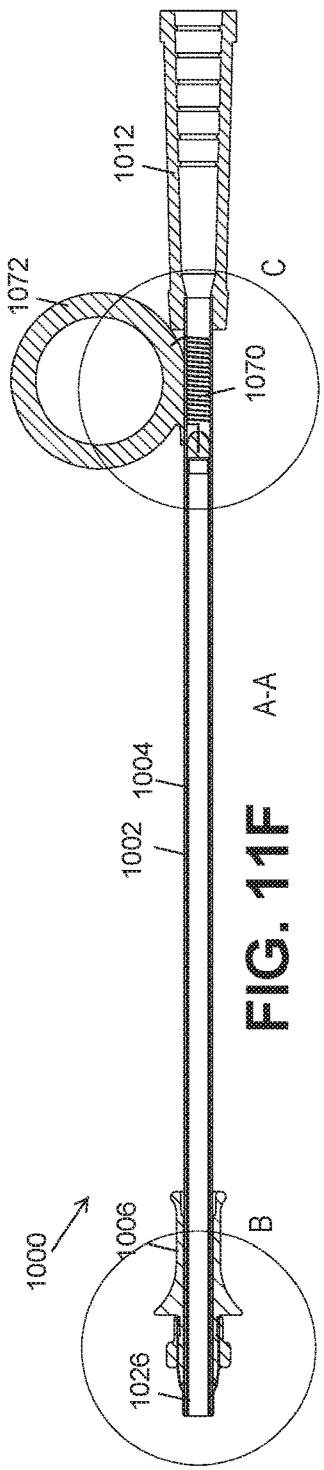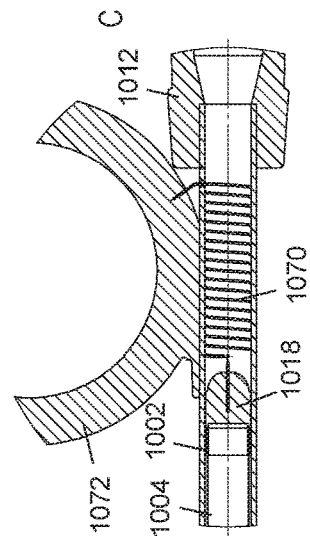
FIG. 11E
FIG. 11F
FIG. 11G
FIG. 11H

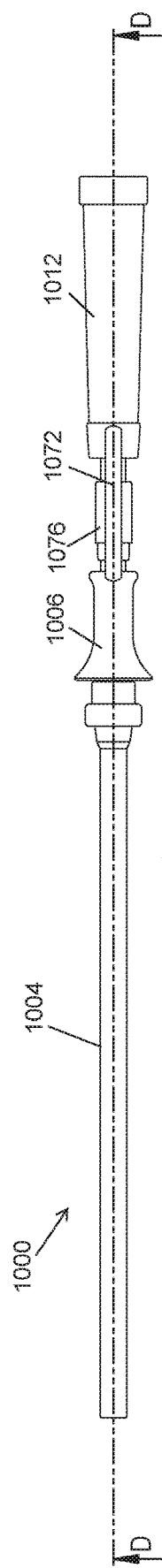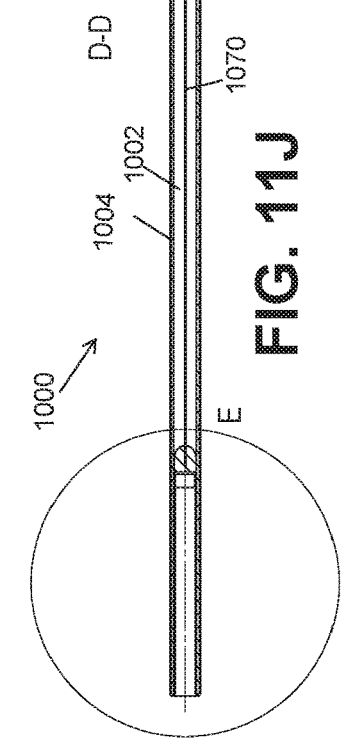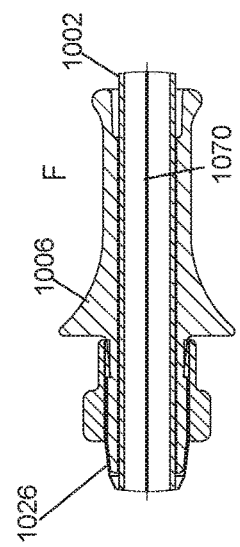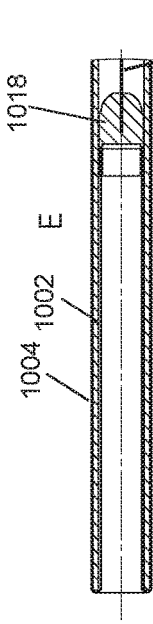

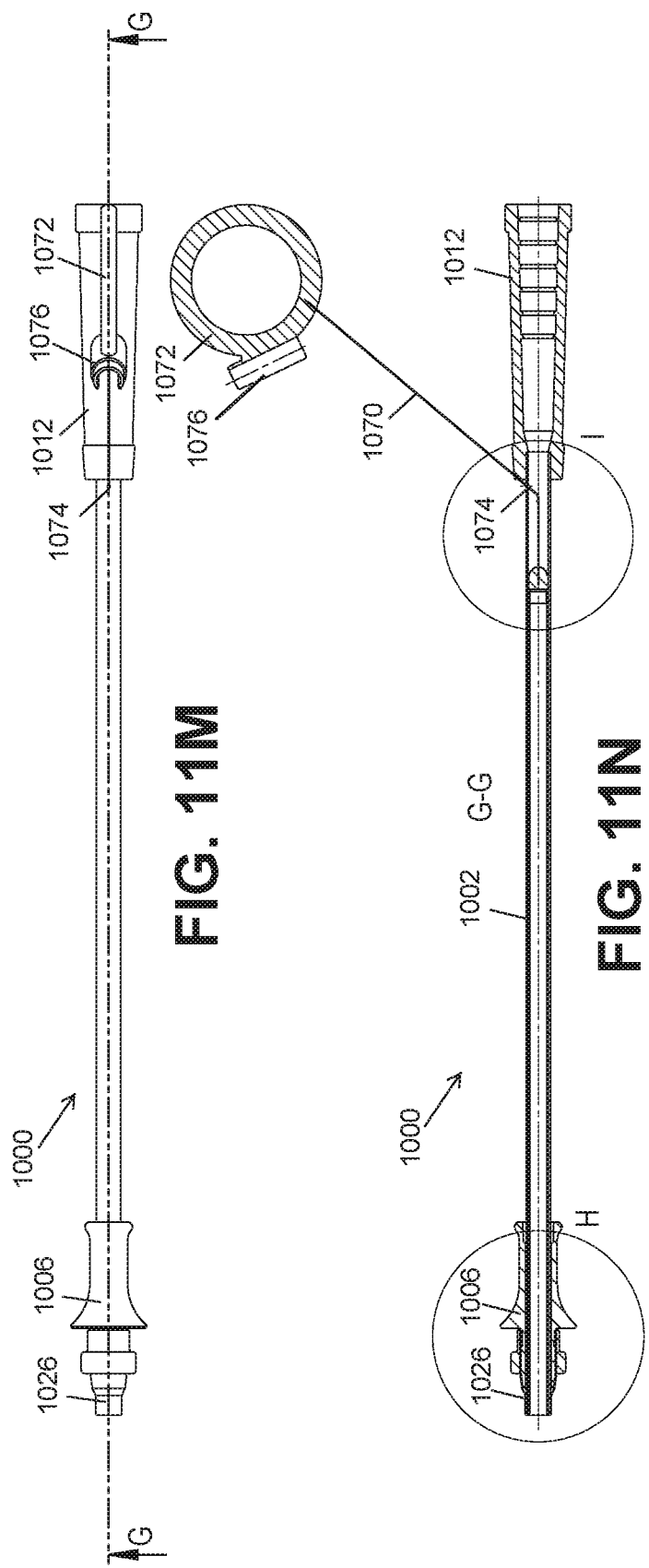
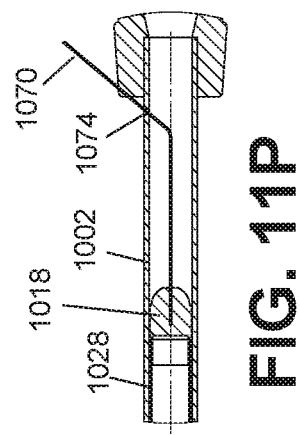
FIG. 11M
FIG. 11N
FIG. 11O
FIG. 11P

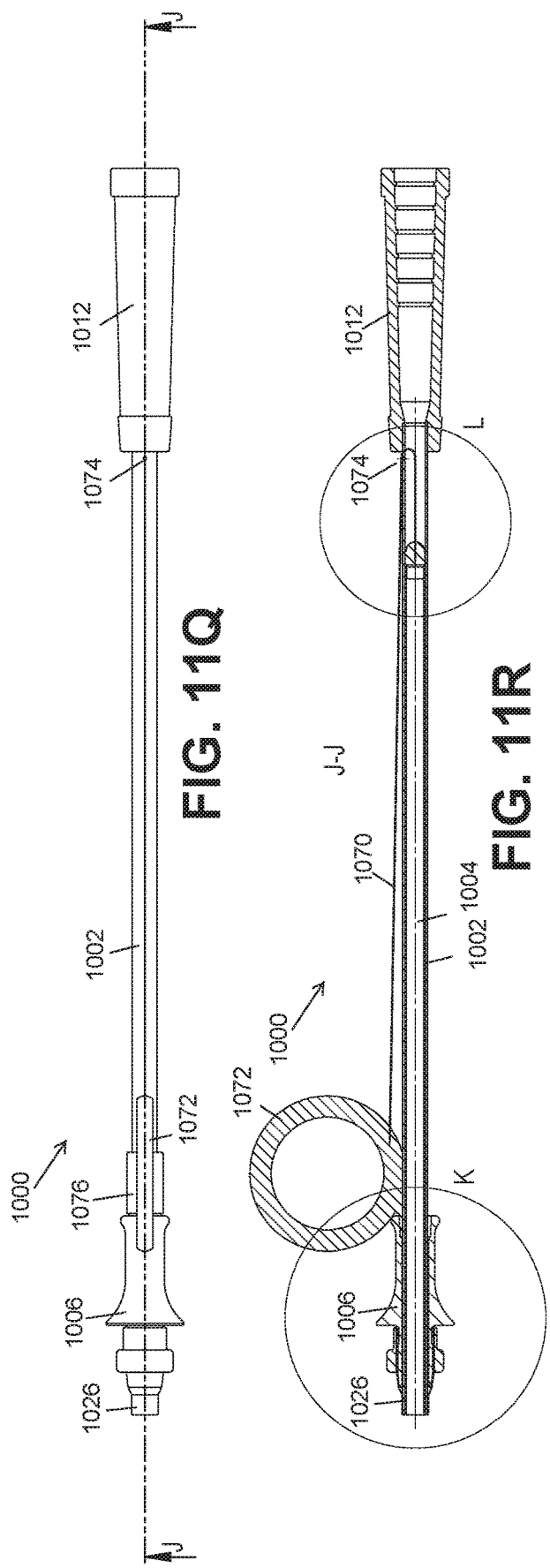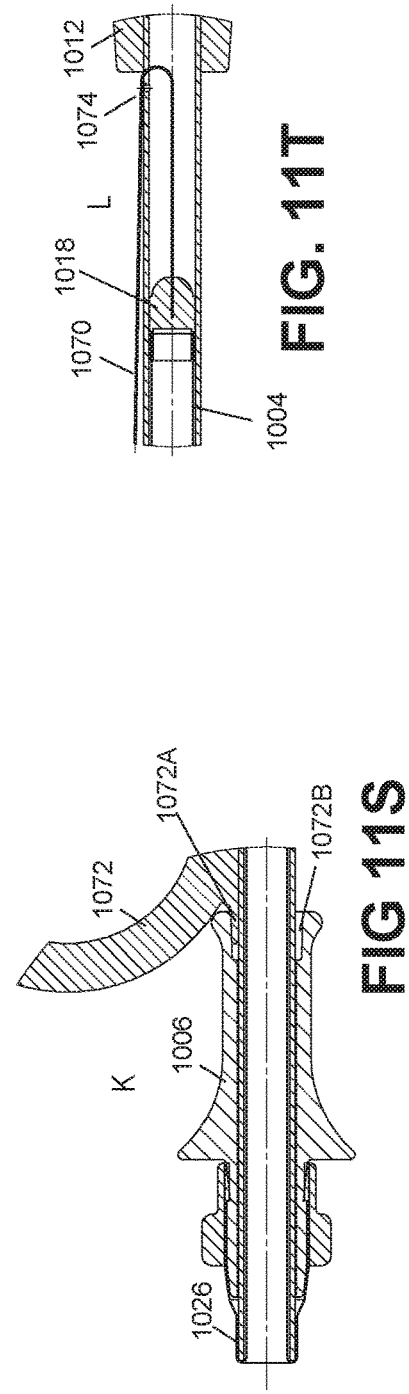

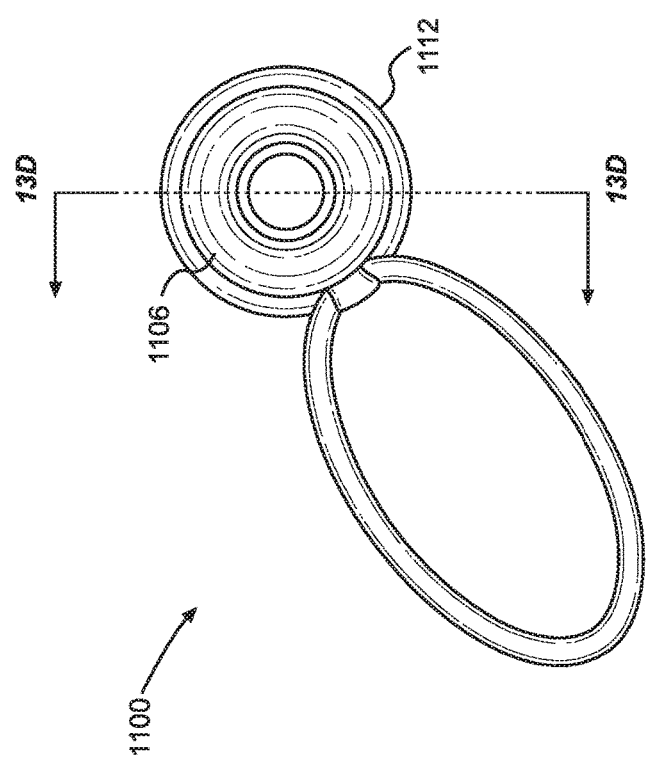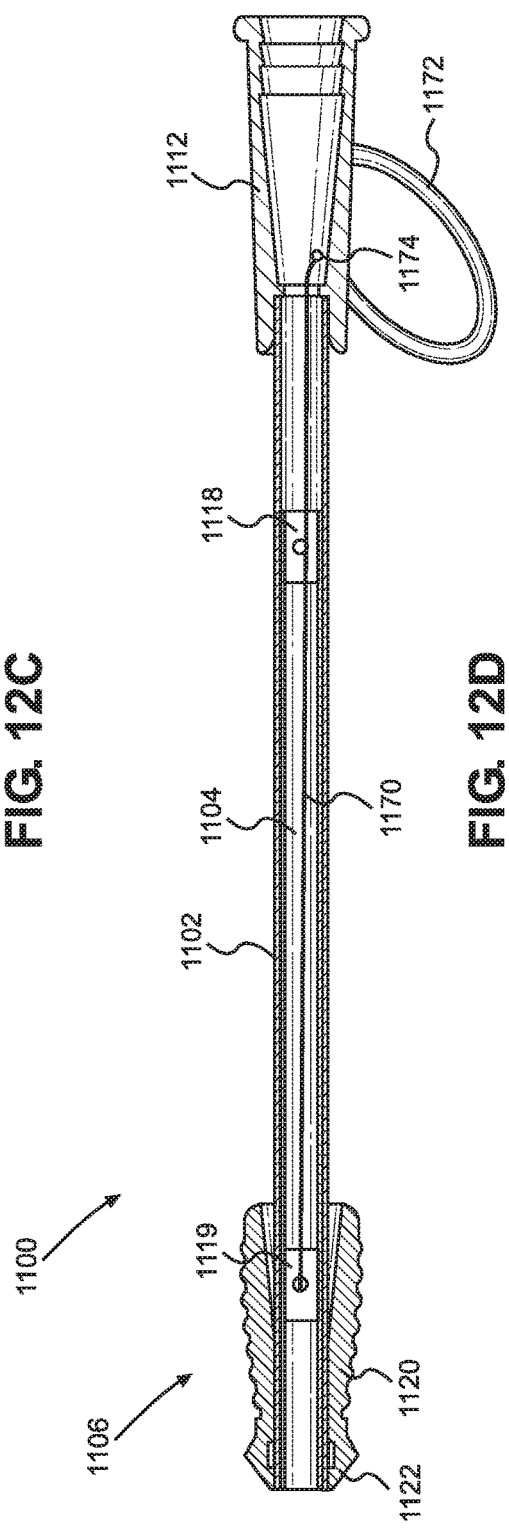
FIG. 12C
FIG. 12D

MOLDED TIP ATTACHED TO EXTRUSION
MAY HAVE VARIABLE PITCH

SPIRAL CUT ON TIP OF EXTRUSION
MAY HAVE VARIABLE PITCH

SKIVED OPENINGS THROUGH EXTRUSION
SIZE, SHAPE AND LOCATION OF SKIVES MAY BE VARIABLE

FRICTIONLESS CATHETER

This application claims priority to U.S. Provisional Patent Application No. 62/585,357, filed on Nov. 13, 2017, and titled "FRICTIONLESS CATHETER", the entire disclosure of which is incorporated herein.

BACKGROUND

Technical Field

This application relates generally to systems, devices, and methods for inserting a medical device into a lumen, and more specifically to systems, devices, and methods of a frictionless catheter for insertion into a urethra.

Background

Urinary catheters are often used to void urine from a patient's bladder by being inserted through a urethra and into the bladder. The urinary catheter may be temporarily inserted and removed after the bladder is voided.

SUMMARY

The present inventors recognize that there is a need to improve one or more features of the catheter. For example, the urinary catheter can be a source of a catheter-associated urinary tract infection (CAUTI) by introducing pathogens into the urethra and/or bladder. Insertion and removal of the catheter can also cause substantial pain by kinetic friction between the catheter and the mucosa of the urethra. A lubricant coating can also be unfavorable due to potential drying of the lubricant coating during storage and/or insertion, and/or discharging of the lubricant coating during use which can stain clothes of a user. The disclosed devices and methods are directed to mitigating or overcoming one or more of the problems set forth above and/or other problems of the prior art.

A first aspect of the various embodiments of the invention disclosed herein is directed to a catheter including: a tubular member having a lumen and an outer surface; a sleeve configured to be positioned in the lumen in a retracted configuration and to evert over at least a portion of the outer surface in an everted configuration; a filament configured to retract the sleeve into the retracted configuration; and an aperture proximal of a distal end of the catheter, wherein the filament extends from the lumen through the aperture and out of the catheter. In some embodiments, the catheter may include a distal member having a distal opening, wherein the aperture extends through the distal member. In some embodiments, the catheter may further include a pull member on a distal end of the filament. In some embodiments, the pull member may include a pull ring or a pull tab. In some embodiments, the filament may be looped, coiled, and/or bunched in the catheter when the sleeve is in the retracted configuration. In some embodiments, a shuttle may be attached to a distal end of the sleeve, where the shuttle is a tubular member configured to maintain patency of the sleeve, and the filament engages the shuttle to retract the sleeve into the lumen. In some embodiments, the filament may extend past the shuttle in the retracted configuration. In some embodiments, the filament may be attached to the shuttle. In some embodiments, the catheter may include a second shuttle proximal of the shuttle, where the filament is attached to the second shuttle, and retraction of the filament causes the second shuttle to abut the shuttle and retract the sleeve. In some embodiments, the tubular member may include at least one cut or hole extending through a proximal portion of the tubular member to increase flexibility of the proximal portion. In some embodiments, the at least one cut or hole extends along less than half of a length of the tubular member. In some embodiments, the at least one cut or hole varies along a length of the proximal portion to provide variable flexibility. In some embodiments, the catheter may include a proximal member secured to a proximal portion of the sleeve, where the proximal member is configured to slide over at least a portion of the tubular member to evert the sleeve over the tubular member. In some embodiments, the catheter may include a bag distal of the tubular member.

A second aspect of the various embodiments of the invention disclosed herein is directed to a method of draining a volume of fluid with the catheter, the method including inserting the tubular member into a bodily lumen; everting the sleeve over the outer surface of the tubular member from the lumen of the tubular member; and pulling the filament to pull the sleeve through the lumen to remove the tubular member from the bodily lumen. In some embodiments, the filament may be looped, coiled, or bunched in the lumen of the catheter before inserting the tubular member. In some embodiment, the pulling the filament may include pulling the filament through the aperture of the catheter. In some embodiments, the pulling the filament may include pulling a pull tab or a pull ring attached to a distal end of the filament. In some embodiments the method may further include sliding a proximal member secured to a proximal end of the sleeve to evert the sleeve over the outer surface.

A third aspect of the various embodiments of the invention disclosed herein is directed to a catheter comprising: a tubular member having a lumen and an outer surface; a sleeve configured to be positioned in the lumen of the tubular member in a retracted configuration and to evert over at least a portion of the outer surface of the tubular member in an everted configuration; and a chamber configured to receive a distal portion of the sleeve in the retracted configuration. In some embodiments, the catheter comprises a distal housing including the chamber, wherein the distal housing comprises a diameter larger than the tubular member. In some embodiments, the distal housing comprises a distal member secured to the distal portion of the sleeve, and a chamber member enclosing the chamber, where the distal member is configured to separate from the chamber member to pull the sleeve distally through the lumen of the tubular member. In some embodiments, the distal portion of the sleeve extends between the distal member and chamber member. In some embodiments, a locking member is configured to releasably secure the distal member and the chamber member. In some embodiments, a slider is configured to slide relative to the distal housing to advance and/or retract the tubular member relative to the distal housing. In some embodiments, the slider comprises an actuator configured to pinch the sleeve to retract the tubular member. In some embodiments, the distal housing is configured to receive the tubular member. In some embodiments, a pulley is configured to slide in the distal housing, the pulley being configured to support the sleeve. In some embodiments, a proximal member is secured to a proximal portion of the sleeve and configured to slide over at least a portion of the tubular member to evert the sleeve of the tubular member. In some embodiments, the proximal member includes a mushroom-shaped proximal end configured to engage an opening of a bodily lumen. In some embodiments, the distal portion of the sleeve is folded and/or pleated in the chamber. In another embodiment, the tubular member comprises a spiral cut extending through a proximal portion of the tubular member. In some embodiments, the spiral cut extends along less than half of a length of the tubular member. In some embodiments, the spiral cut has a variable pitch.

There are, of course, additional aspects of the various embodiments of the invention disclosed herein that will be described below and which will form the subject matter of the claims. In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the disclosure are illustrated by way of examples in the accompanying drawings.

FIGS. 1A-D illustrate a first exemplary embodiment of a catheter of the present invention.

FIGS. 3A-L illustrate a second exemplary embodiment of a catheter of the present invention.

FIGS. 4A-L illustrate a third exemplary embodiment of a catheter of the present invention.

FIGS. 5A-K illustrate a fourth exemplary embodiment of a catheter of the present invention.

FIGS. 6A-J illustrate a fifth exemplary embodiment of a catheter of the present invention.

FIGS. 7A-I illustrate a sixth exemplary embodiment of a catheter of the present invention.

FIGS. 8A-K illustrate a seventh exemplary embodiment of a catheter of the present invention.

FIGS. 9A-I illustrate an eighth exemplary embodiment of a catheter of the present invention.

FIGS. 10A-I illustrate a ninth exemplary embodiment of a catheter of the present invention.

FIGS. 11A-T illustrate a tenth exemplary embodiment of a catheter of the present invention.

FIGS. 12A-F illustrate an eleventh exemplary embodiment of a catheter of the present invention.

Aspects of a catheter according to aspects of the disclosure are described with reference to the drawings, in which like reference numerals refer to like parts throughout.

DETAILED DESCRIPTION

Figure 1C:
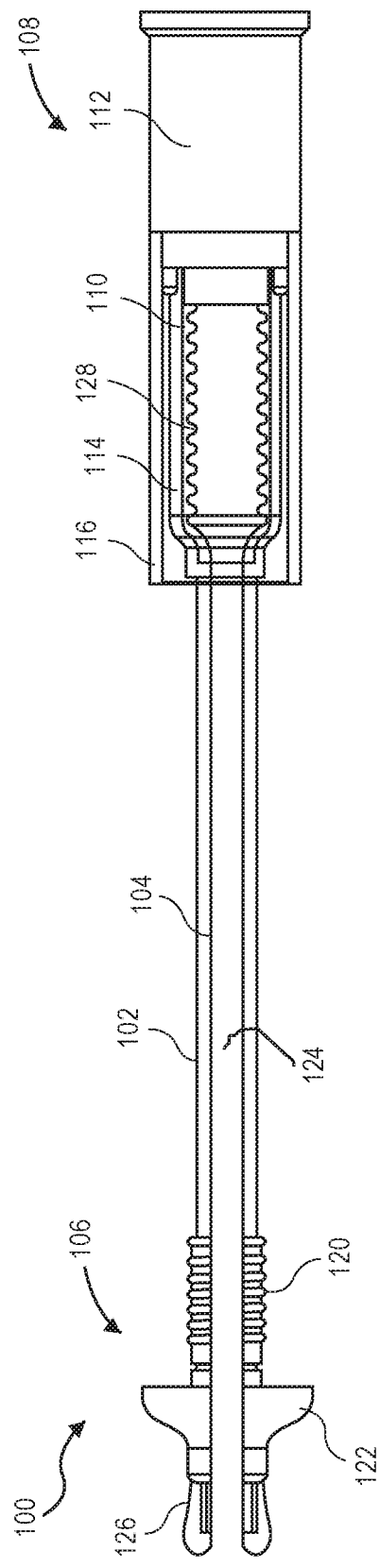

The presently disclosed invention is generally directed frictionless catheters and methods of use to partially or completely eliminate kinetic friction of the catheter when inserted into a lumen contacting tissue, such as the urethra. The catheter may include a tubular member having a lumen housing a rolling sleeve. As used herein, the term "sleeve" or "rolling sleeve" shall refer to a generally flexible, thin membrane or sheath, in tubular or hollow form, defining an internal lumen therethrough, which can be continuously everted from an inner lumen of the tubular member, over a proximal opening of the tubular member, and then distally over the outer surface of the tubular member. The term "proximal" shall refer to in the direction of insertion into the body during the intended use, and term "distal" shall refer to in the opposite direction toward the portion of the catheter handled by the user during the intended use.

A proximal portion of the rolling sleeve may be attached to a proximal member configured to slide over at least a portion of an outer surface of the tubular member. In some embodiments, the outer diameter of the tube and an inner diameter of the proximal portion may have an oval cross-section to reduce relative rotation and twisting of the sleeve. In some embodiments, a distal portion of the rolling sleeve may be stored in a chamber adjacent to or near a distal portion of the tubular member, and the rolling sleeve may be folded and/or pleated in the stored and/or retracted configuration in said chamber. During insertion of the catheter, the proximal member is configured to engage female or male anatomy (e.g., the urethra meatus) and slide distally over the tubular member, drawing the rolling sleeve out of the lumen of the tubular member and everting the rolling sleeve over an outer surface of the tubular member as the tubular member advances into the urethra. The catheter allows passage of urine from the bladder into the proximal opening of the tubular member and out of a distal opening of a distal member. The distal member may include an inner funnel section to provide favorable fluid flow into a bathroom receptacle (e.g., a toilet or urinal). In some embodiments, the distal member may be attached to a bag that collects the urine for later disposal.

In some embodiments, the rolling sleeve may be attached to a filament, which may be pulled to draw the rolling sleeve back through the lumen of the tubular member. The filament may have a pull member (e.g., a pull ring or a pull tab). The pull member may be larger than the filament and be made of a more rigid material than the filament to facilitate grasping and pulling by a patient with reduced dexterity. The filament may also extend through an aperture proximal of a distal end of the catheter to provide an improved angle for self-administration and to improve sanitation by reducing urine contact with the filament and pull member. The pull member may be enlarged to prevent passage of the pull member through the aperture. The positioning of the aperture may allow for attachment of a bag on a distal end of the catheter without interference with the filament or pull member.

The catheter may include one or more tubular shuttles. The sleeve may have a tubular shuttle attached to a distal end. The tubular shuttle may have a greater hoop strength than the sleeve to maintain patency of the sleeve. The filament may directly or indirectly engage with the shuttle to retract the sleeve. For example, in some embodiments, the catheter system may include a single shuttle attached to the distal end of the filament and the proximal end of the sleeve, such that pulling the filament directly pulls the shuttle and sleeve distally through the lumen of the tubular member. In these embodiments, the filament may be looped, coiled, and/or bunched between the attachment of the pull member and the attachment of the shuttle and disposed in the lumen of the catheter during storage to ensure that a sufficient length of filament is provided and maintained sterile. In other embodiments, the catheter may include a first shuttle attached to a distal end of the sleeve and a second shuttle fixed to the filament, where the second shuttle is positioned proximally of the first shuttle. In these embodiments, the second shuttle may maintain tension on the filament during storage, and during retraction of the filament, the second shuttle may abut and slide the first shuttle distally to pull the sleeve into the tubular member. The filament may extend proximally past the shuttle attached to the sleeve to maintain sufficient length of filament in the lumen of the catheter during storage to enable retraction of the sleeve after voiding. For example, in some embodiments, the stored length of filament may be at least half of the length of the tubular member or catheter overall. In some embodiments, the stored length of filament may be at least three-quarters of the length of the tubular member or catheter overall. In some embodiments, the stored length of filament may be at least substantially equal to or greater than the length of the tubular member or catheter overall.

The drawing of the rolling sleeve through the tubular member and the interaction between the rolling sleeve and the outer surface of the tubular member delivers internal friction to the catheter. However, the relative movement of the rolling sleeve along the mucosa of the urethra is minimal or zero, thus delivering minimal or zero kinetic friction to the urethra. The catheter shaft and the rolling sleeve may be dry and uncoated to prevent cracking of the sleeve. The rolling sleeve may be ultra-thin having a thickness less than 10 microns. The catheters of the present disclosure may reduce the likelihood of CAUTI since the rolling sleeve does not draw pathogens into the urethra and bladder. In some embodiments, the likelihood of CAUTI may be even further reduced with the storage of the distal portion of the rolling sleeve in the chamber of the catheters.

The catheters of the various embodiments may be compact with ergonomic attributes lending to ease of use and device handling. In some embodiments, the user may handle the tubular member to facilitate handling during insertion. The catheters do not require lubricant coatings or fluid activation, reducing the risk of stained clothes of the user during insertion. The dwell-time of the catheters may be irrelevant, without any coating or osmolality concerns. The dry sleeves and catheters may also be odorless, with reduced user aseptic preparation. Furthermore, the dry sleeves of the present disclosure do no provide nourishment for pathogen colonization. The components of the catheters may be assembled completely mechanically (e.g., snap-fit), without the use of adhesives to produce simpler and more environment-friendly catheters. The catheters may further permit fluid lumen patency regardless of insertion length. In some embodiments, the catheters may be reassembled to limit dripping of urine during disposal of the catheters.

Figure 1D:
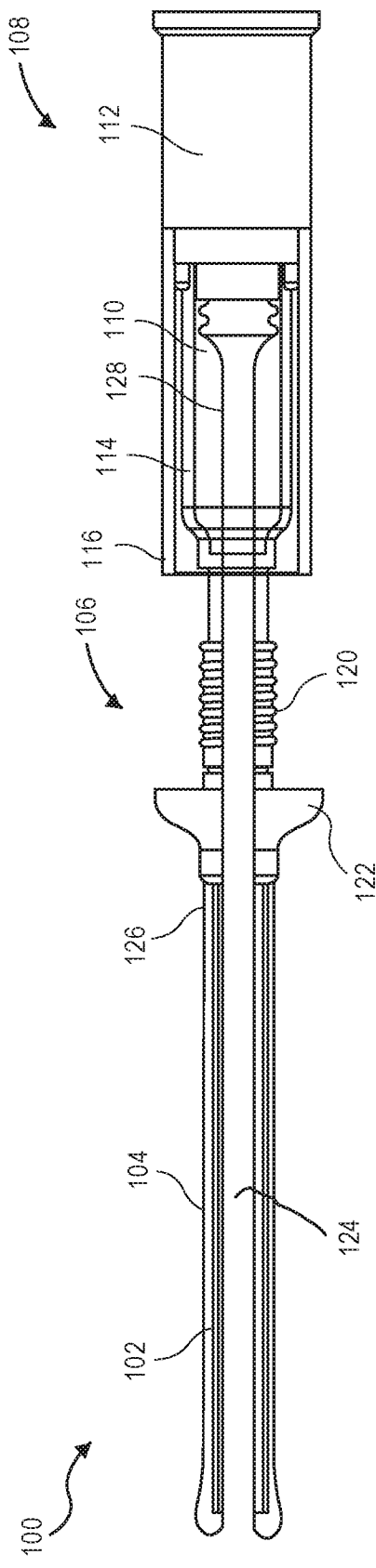
Figure 2A:
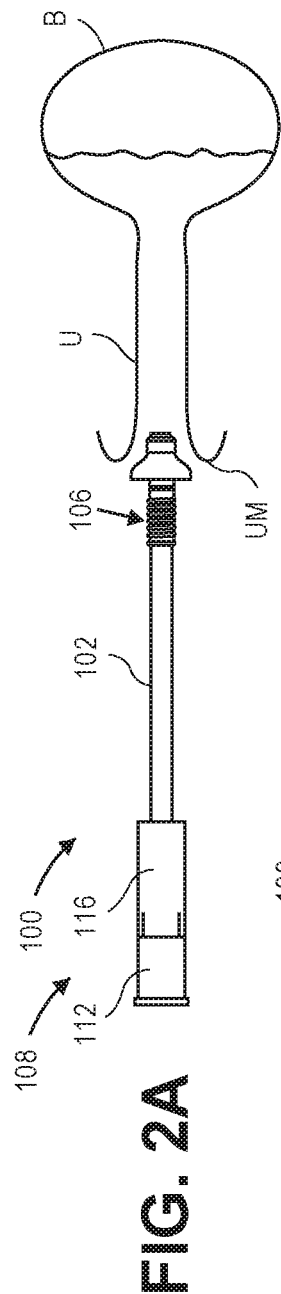
FIGS. 2A-D illustrate exemplary steps of a method of using the first exemplary embodiment of FIGS. 1A-2D.
Figure 2B:
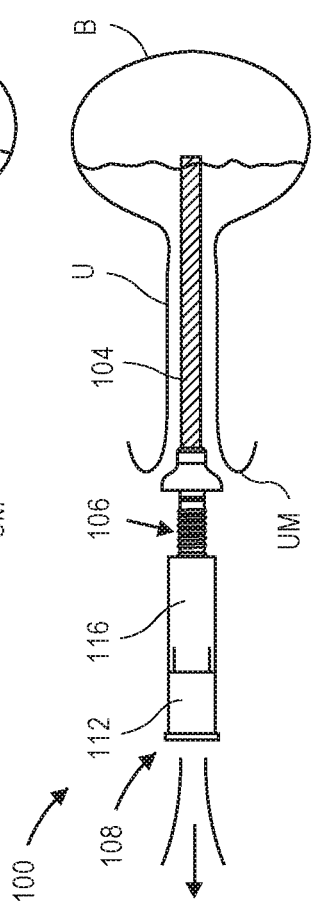
Figure 2C:
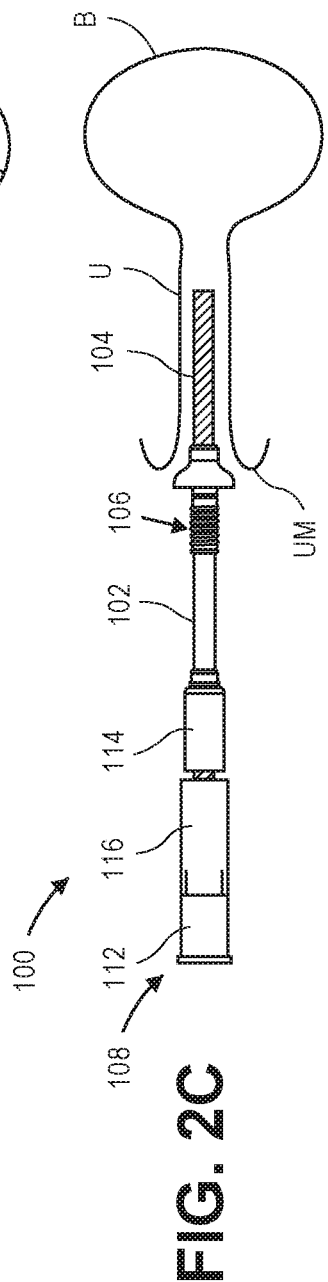
Figure 2D:
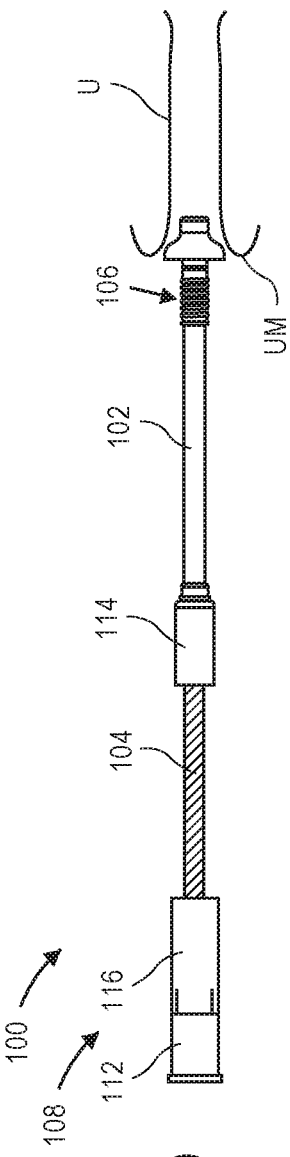

FIGS. 1A-D illustrate a first exemplary embodiment of a frictionless catheter 100 of the present invention, having a tubular member 102, a sleeve 104, a proximal member 106, and a distal housing 108 enclosing a chamber 110. FIG. 1A shows the catheter 100 in a partially inserted configuration, with the tubular member 102 partially advanced past the proximal member 106, and the sleeve 104 everted over a proximal opening of tubular member 102. FIG. 1B shows the catheter 100 in an exploded disassembled form. FIGS. 1C and 2A show the catheter 100 in a ready-to-insert and retracted configuration. FIGS. 1D and 2B show the catheter 100 in a fully inserted and everted configuration. FIG. 2C shows the catheter 100 in the middle of being retracted after insertion. FIG. 2D shows the catheter 100 fully retracted after insertion. The catheter 100 may be inserted through a urethra and/or into a bladder to facilitate drainage of a bladder, as discussed herein. Aspects and components of the catheter 100 may be further discussed with regard to the other embodiments of this disclosure. In that sense, similar components are provided with reference numbers having the same last two digits throughout the present disclosure.

As illustrated in FIGS. 1A-B, the distal housing 108 may include a distal member 112, a chamber member 114, and a tubular jacket 116. The chamber member 114 may at least partially enclose the chamber 110, and the distal member 112 may have a tubular extension 118 at least partially received in the chamber member 114. The chamber 110 and/or the chamber member 114 may have a diameter larger than the tubular member 102 to receive a distal portion of the sleeve 104 in a stored and/or retracted configuration. The distal housing 108 may be releasably secured through an interference and/or snap fit. For example, the chamber member 114 may include one or more protrusions configured to snap into a groove on the distal member 112, and/or vice versa. The one or more protrusions may be configured to release the distal member 112 when sufficient force is applied to the distal member 112 and/or the chamber member 114.

The chamber member 114 may be attached to a distal portion of the tubular member 102, and the distal member 112 may be attached to the distal portion 128 of the sleeve 104. Therefore, after the distal member 112 is released from the chamber member 114, the distal member 112 may be retracted away from the chamber member 114 to retract the sleeve 104 through the tubular member 102. The retraction of the sleeve 104 through the tubular member pulls the sleeve 104 and the tubular member 102 through the urethra for removal of the catheter 100, as discussed herein. The distal member 112 may include a distal opening and an inner funnel section to facilitate passage of urine out of the distal opening when in communication with the urethra and/or bladder. The distal opening may also be fluidly connected to a urinary bag to collect the urine.

As further illustrated in FIGS. 1A-B, the proximal member 106 may be configured to slide along the tubular member 102 to draw the sleeve 104 through (into or out) of the tubular member 102. For example, when the proximal member 106 slides distally along the tubular member 102, the sleeve 104 is pulled out of the tubular member 102. The proximal member 106 slides proximally along the tubular member 102, when the sleeve 104 is pulled into the tubular member 102. The proximal member 106 may also function as an introducer aid to facilitate handling and insertion into the urethra. The proximal member 106 may have a gripping or handling portion 120 on a distal portion and a tissue engaging member 122 on a proximal portion. The handling portion 120 may include one or more ribs and/or grooves, or the like to enhance grip of the user. The tissue engaging member 122 may include a convex mushroom-shaped portion to engage anatomy, such as the urethra meatus. The convex portion may include a concave portion on its distal side configured to shield the convex portion from the handling portion 120, reducing manual contact of the convex portion and introduction of pathogens into the urethra. The handling portion 120 and the tissue engaging member 122 may be separable, as illustrated in FIG. 1B.

The tubular member 102 may be sized and shaped for any type of anatomy. When configured to treat male and/or female urethra, the tubular member 102 may have a round cross-section, not necessarily reflective of the urethra. However, it is contemplated that the tubular member 102 may have non-round cross-sections. An oval cross-section for the tubular member 102 and/or proximal member 106 is particularly advantageous to prevent relative rotation and torsion on the sleeve 104, that would produce tearing or friction relative to the urethra. In some embodiments, the tubular member 102 may be curved along a length in order to accommodate a curvature of a male urethra. In some embodiments, the tubular member 102 may be shorter in length to traverse a female urethra. The tubular member 102 may receive a cuff 130 on a proximal opening.

As illustrated in FIGS. 1C-D, the sleeve 104 may extend from the distal housing 108, through the lumen 124 of the tubular member 102, and evert over at least a portion of an outer surface of the tubular member 102 at its proximal end. The sleeve 104 may have a proximal portion 126 attached to the proximal portion of the proximal member 106 and a distal portion 128 received in the chamber 110. The distal portion 128 of the sleeve 104 may be secured around the tubular extension 118 of the distal member 112, thus extending between the distal member 112 and the chamber member 114. As illustrated in FIG. 1C, the distal portion 128 may be folded and/or pleated when positioned over the tubular extension 118 in the chamber 110 in a stored and/or retracted configuration. The sleeve 104 may elongate and the distal portion 128 may unfold, for example, when the proximal member 106 slides distally along the tubular member 102 (e.g., FIG. 1D) and/or the distal member 112 is retracted relative to the chamber member 114. However, the folded and/or pleated configuration ensures patency of the sleeve 104, by preventing bunching of the sleeve 104 in the lumen of the catheter 100 and allowing bladder voiding function independent of the length of the urethra and/or the extension of the tubular member 102.

FIGS. 2A-D illustrate exemplary steps of a method of using the catheter 100 of FIGS. 1A-D. As illustrated in FIG. 2A, the proximal member 106 may act as an introducer aid and facilitate handing of the catheter and location/engagement of a bodily lumen, such as the urethra meatus (UM). A covered proximal length of the tubular member 102 may extend proximally out of the proximal member 106, for example, promoting navigation through the *Labia majora* and *Labia minora* and location of the urethra meatus (UM) for females. However, because the proximal portion of the tubular member 102 is sheathed by the sleeve 104 and the sleeve 104 everts, further insertion of the tubular member 102 and the sleeve 104 into the urethra does not push pathogens from the initial location of the urethra meatus.

As illustrated in FIG. 2B, the tubular member 102 and the sleeve 104 may be advanced into a urethra (U) and/or a bladder (B) to void the bladder. The tubular member 102 and the sleeve 104 may be advanced by pushing the tubular member 102 proximally relative to the proximal member 106 and/or pulling the proximal member 106 relative to the tubular member 102. Once inserted into the urethra (U) and/or the bladder (B), urine may pass through the proximal opening of the tubular member 102, which may be lined by the sleeve 104, and out the distal opening of the distal member 112. In some embodiments, the urine may then be received in a bag attached to the distal member 112.

As illustrated in FIGS. 2C-D, after voiding is complete, the distal member 112 may be released from the chamber member 114 to remove the tubular member 102 and the sleeve 104 from the urethra (U) and bladder (B). The distal member 112 may be retracted relative to the chamber member 114 to retract the tubular member 102 through the proximal member 106 and the sleeve 104 through the lumen of the tubular member 102. Thus, the distal member 112, which may be initially attached to the distal end of sleeve 104 and separates from the chamber member 114 during retraction. The distal housing 108 may then be reassembled to reduce dripping of urine prior to disposal, for example, by feeding the sleeve 104 back into the chamber member 114 and reassembling the distal member 112 and the chamber member 114.

Figure 3H:
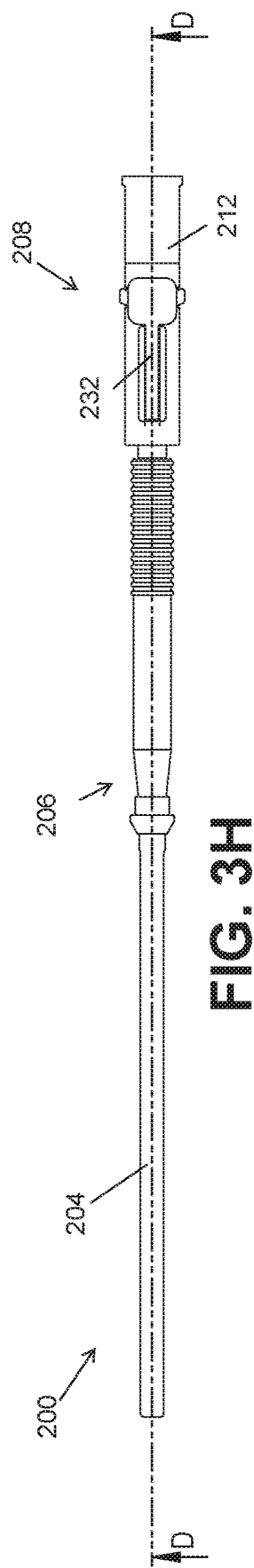
Figure 3I:
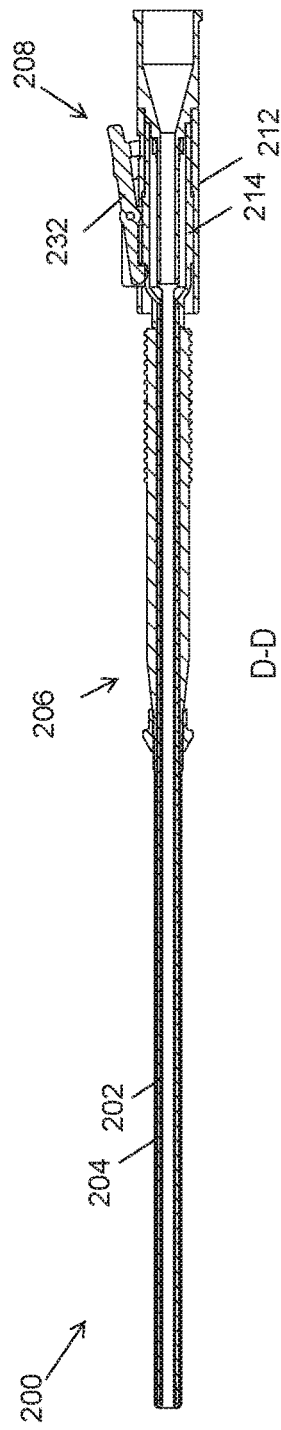

FIGS. 3A-L illustrate a second exemplary embodiment of a frictionless catheter 200 of the present invention, having a tubular member 202, a sleeve 204, a proximal member 206, and a distal housing 208 having an inner chamber 210. FIGS. 3A-E show the catheter 200 in a ready-to-insert and retracted configuration. FIG. 3B is a cross-sectional view of the catheter 200 in FIG. 3A taken along line A-A. FIG. 3C is an enlarged view of the region B shown in FIG. 3B. FIG. 3D is an enlarged view of the region C shown in FIG. 3B. FIGS. 3F, 3H, and 3I show the catheter 200 in a fully inserted and everted configuration. FIG. 3I is a cross-sectional view of the catheter 200 in FIG. 3H taken along line D-D. FIGS. 3J, 3K, and 3L show the catheter 200 fully retracted after insertion. FIG. 3K is a cross-sectional view of the catheter 200 in FIG. 3J taken along line E-E. FIG. 3L is another view of the catheter 200 from a side rotated 90 degrees relative to FIG. 3J. The catheter 200 may be inserted through a urethra and/or into a bladder to facilitate drainage of a bladder, as discussed herein. Aspects and components of the catheter 200 may be further discussed with regard to the other embodiments of this disclosure. In that sense, similar components are provided with reference numbers having the same last two digits throughout the present disclosure.

The proximal member 206 may have a handling portion 220 of substantial length to facilitate handling and navigating harder to reach anatomy, and a tissue engaging member 222 for insertion into the urethral meatus, as well as to attach to a proximal end 226 of the sleeve 204. The sleeve 204 is thus attached to the proximal member 206 at its proximal end. The sleeve 204 may extend through the inner lumen of tubular member 202 and attach at its distal portion 228 to a distal member 212 of the distal housing 208. The distal portion 228 may be folded, pleated, or otherwise longitudinally compressed over a tubular extension 218 of the distal member 212 and inside of a chamber member 214, when in the ready-to-insert and retracted configuration. Thus, the sleeve 204 may extend between the distal member 212 and chamber 214 to maintain patency of the sleeve 204.

The sleeve 204 everts or rolls into the inner lumen of tubular member 202 over the proximal end opening of tubular member 202, as the catheter 200 is inserted into a urethra. The proximal member 206 slides over the tubular member 202, such that when a user inserts the tissue engaging member 222 of the proximal member 206 into the urethral meatus and pushes the tubular member 202 and/or distal housing 208, the tubular member 202 advances into the urethra while the proximal member 206 slides distally over tubular member 202. The sleeve 204 is pulled proximally from inside the lumen of the tubular member 202 to continuously evert over the proximal opening of the tubular member 202 to form a barrier or layer between the tubular member 202 and the urethra. Thus, the sleeve 204 is stationary relative to the urethra during insertion and retraction, thereby allowing for zero or low kinetic friction during such insertion and retraction. The tubular member 202 may key with an inner surface of the proximal member 206, preventing relative rotation between the tubular member 202 and the proximal member 206 to prevent twisting of the sleeve 204 which may block bladder voiding.

The distal housing 208 may also include a locking member 232 configured to prevent release of a distal member 212 from a chamber member 214 during handling and insertion of the tubular member 202. The distal member 212 may house the chamber member 214. The locking member 232 may include a latching member and/or lever attached to the distal member 212 and biased into engagement with the chamber member 214. The locking member 232 may prevent retraction of the distal member 212 from the chamber member 214 before actuation. For example, the locking member 232 may have a proximal protrusion pivotally received in a locking aperture of the chamber member 214. Upon completion of the voiding of the bladder, a user may actuate the locking member 232 (e.g., by pressing and/or pivoting) to release the distal member 212 from the chamber member 214. Release of the locking member 232 allows retraction of a distal portion 228 of the sleeve 204 relative to the tubular member 202 to facilitate removal of the catheter 200 from the urethra. Thus, the distal member 212 which may be attached to the distal end of sleeve 204 and separates from the chamber member 214 during retraction.

FIGS. 4A-L illustrate a third exemplary embodiment of a frictionless catheter 300 of the present invention, having a tubular member 302, a sleeve 304, a proximal member 306, and a distal housing 308 having an inner chamber 310. FIGS. 5A-D show the catheter 300 in a ready-to-insert and retracted configuration. FIG. 4B is a cross-sectional view of the catheter 300 in FIG. 4A taken along line A-A. FIG. 4C is an enlarged view of the region B shown in FIG. 4B. FIG. 4D is an enlarged view of the region C shown in FIG. 4B. FIGS. 4F, 4I, and 4J show the catheter 300 in a fully inserted and everted configuration. FIG. 4J is a cross-sectional view of the catheter 300 in FIG. 4I taken along line D-D. FIGS. 4G, 4K, and 4L show the catheter 300 fully retracted after insertion. FIG. 4L is a cross-sectional view of the catheter 300 in FIG. 4K taken along line E-E. FIG. 4H shows the catheter 300 in a collapsed configuration for disposal. The catheter 300 may be inserted through a urethra and/or into a bladder to facilitate drainage of a bladder, as discussed herein. Aspects and components of the catheter 300 may be further discussed with regard to the other embodiments of this disclosure. In that sense, similar components are provided with reference numbers having the same last two digits throughout the present disclosure.

The sleeve 304 may be attached to the proximal member 306 at its proximal end. The sleeve 304 may evert or roll into the inner lumen of tubular member 302 over the proximal end opening of tubular member 302. The sleeve 304 may extend through the inner lumen of tubular member 302 and attach at its distal end 328 to a distal member 312 on the distal housing 308. The distal portion of the sleeve 304 may be folded, pleated, or otherwise longitudinally compressed over a tubular extension 318 of the distal member 312 and inside of the distal housing 308, when in the ready-to-insert and retracted configuration. Thus, the sleeve 304 may extend over the distal member 312 to maintain patency of the sleeve 304. The distal housing 308 may include an outer tube housing 334 and an inner tube housing 336.

A slider 350 may be configured to slide along a slot 352 in the outer tube housing 334 and the inner tube housing 336. The slider 350 may be configured to advance the tubular member 302 from the distal housing 308 by pushing a distal end of the tubular member 302. The slider 350 may also include an actuator 354 configured to be depressed and pinch and/or grip the sleeve 304 to retract the sleeve 304 through the tubular member 302 and retract the tubular member 302. The pinching and/or gripping of the sleeve 304 by the actuator 354 may eliminate any slack in the sleeve 304, such that the retraction of the sleeve 304 and tubular member 302 commences immediately upon retraction of the slider 350. The slack in the sleeve 304 may be due to the advancement of the catheter 300 into the urethra to a distance where voiding commences. This distance can vary due to anatomy and user size variances, and the catheter 300 is designed to accommodate full shaft length insertion. Thus, slack is generated by the difference between the insertion length and the full shaft length.

As illustrated in FIGS. 4F-H and 4K-L, the slider 350 may be retracted distally and may eventually engage with the inner tube housing 336. The slider 350 pushes the inner tube housing 336 out from the outer tube housing 334 until the entire tubular member 302 is retracted from the urethra in a frictionless manner and is received in the outer tube housing 334. The inner tube housing 336 may manage the sleeve 304, and the user may have no visual of the sleeve-tubular member mechanism. The slider 350 only pushes the tubular member 302, and the slider 350 disengages from the tubular member 302 when the slider 350 is retracted. Thus, the tubular member 302 may be floating and only be retracted by the slider 350 retracting the sleeve 304. After the slider 350 is retracted, the inner tube housing 336 may be slid back into the outer tube housing 334 to form a fully collapsed, compact configuration.

FIGS. 5A-K illustrate a fourth exemplary embodiment of a frictionless catheter 400 of the present invention, having a tubular member 402, a sleeve 404, a proximal member 406, and a distal housing 408 enclosing a chamber 410. FIGS. 5A-E show the catheter 400 in a ready-to-insert and retracted configuration. FIG. 5B is a cross-sectional view of the catheter 400 in FIG. 5A taken along line A-A. FIG. 5C is an enlarged view of the region C shown in FIG. 5B. FIG. 5D is an enlarged view of the region B shown in FIG. 5B. FIGS. 5F, 5H, and 5I show the catheter 400 in a fully inserted and everted configuration. FIG. 5I is a cross-sectional view of the catheter 400 in FIG. 5H taken along line D-D. FIGS. 5G, 5J, and 5K show the catheter 400 fully retracted after insertion. FIG. 5K is a cross-sectional view of the catheter 400 in FIG. 5J taken along line E-E. The catheter 400 may be inserted through a urethra and/or into a bladder to facilitate drainage of a bladder, as discussed herein. Aspects and components of the catheter 400 may be further discussed with regard to the other embodiments of this disclosure. In that sense, similar components are provided with reference numbers having the same last two digits throughout the present disclosure.

The sleeve 404 may be attached to the proximal member 406 at its proximal end 426. The sleeve 404 may invert or roll into the inner lumen of tubular member 402 over the proximal end opening of tubular member 402. The sleeve 404 may extend through the inner lumen of tubular member 402 and attach at its distal portion 428 to a distal member 412 on the distal housing 408. The distal portion 428 of the sleeve 404 may be folded, pleated, or otherwise longitudinally compressed over a tubular extension 418 of the distal member 412 and inside of the distal housing 308, when in the ready-to-insert and retracted configuration to maintain patency of the sleeve 404.

The catheter 400 may have a compact, enclosed tubular member 402 with ergonomical attributes lending to ease of use and device handling. The catheter 400 may be provided to the user in a compact state where the tubular member 402 and the sleeve 404 residing the distal housing 408. The distal housing 408 may include an outer housing tube or chamber member 414 to provide a favorable low-profile and handling for self-insertion. The distal housing 408 may also include the distal member 412 configured to be releasably secured to the chamber member 414. A slider 450 may be configured to slide along the chamber member 414 and engage the tubular member 402 through a slot (not shown) in the chamber member 414. The slider 450 may be configured to advance the tubular member 402 from the chamber member 414 into the urethra by pushing a distal end of the tubular member 402. The advancement of the tubular member 402 may draw the sleeve 404 from the chamber 410, and the sleeve 404 everts over the tubular member 402 as the tubular member 402 is advanced into the urethra and/or bladder. Although FIG. 5E depicts the chamber 410 being disposed in the chamber member 414, the chamber 410 may, additionally or alternatively, be in the distal member 412.

The distal housing 408 may further include a locking member 432 configured to prevent release of the distal member 412 from the chamber member 414 during handling and insertion of the tubular member 402. The locking member 432 may include a latching member and/or lever attached to the distal member 412 and biased into engagement with the chamber member 414. The locking member 432 may prevent retraction of the distal member 412 from the chamber member 414 before actuation. Upon completion of the voiding of the bladder, a user may actuate the locking member 432 (e.g., by pressing and/or pivoting) to release the distal member 412 from the chamber member 414. The locking member 432 may have a proximal protrusion received in an aperture of the chamber member 414, such that pressing a proximal portion of the locking member 432 may release the distal member 412 from the chamber member 414. Release of the locking member 432 may allow retraction of the distal portion 428 and and extension of the sleeve 404 relative to the tubular member 402 to facilitate removal of the catheter 400 from the urethra.

Figure 6I:
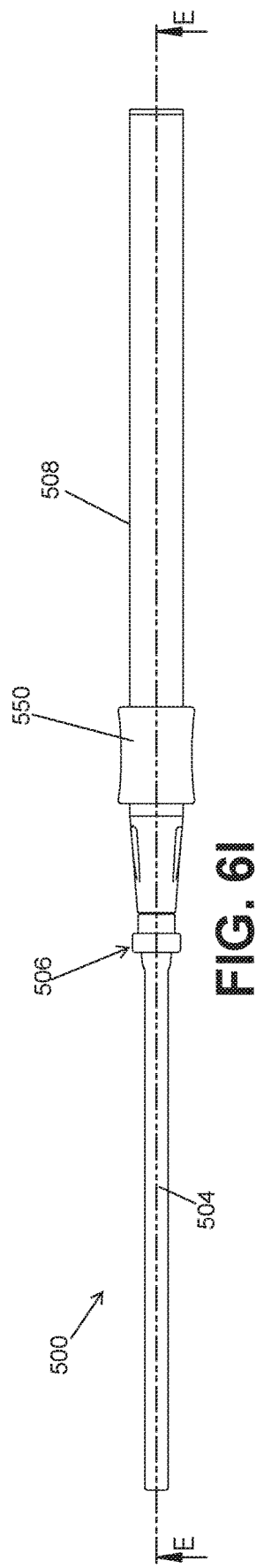
Figure 6J:
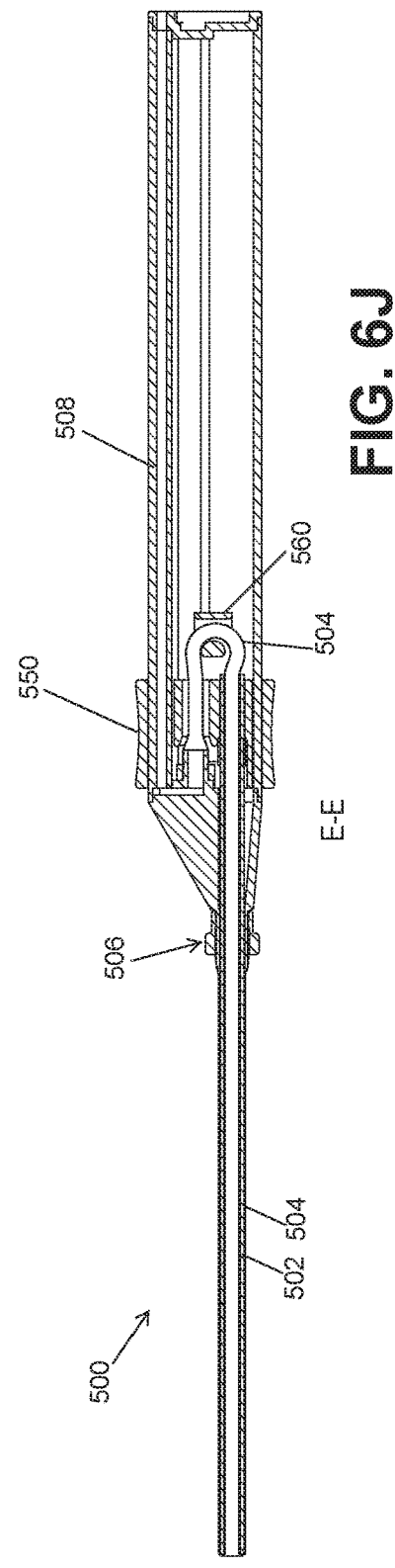

FIGS. 6A-J illustrate a fifth exemplary embodiment of a frictionless catheter 500 of the present invention, having a tubular member 502, a sleeve 504, a proximal member 506, and a housing 508 having a chamber 510. FIGS. 6A-F show the catheter 500 in a ready-to-insert and retracted configuration. FIG. 6B is a cross-sectional view of the catheter 500 in FIG. 6B taken along line A-A. FIG. 6C is an enlarged view of the region B shown in FIG. 6B. FIG. 6D is an enlarged view of the region C shown in FIG. 6B. FIG. 6E is an enlarged view of the region D shown in FIG. 6B. FIGS. 6G, 6I, and 6J show the catheter 500 in a fully inserted and everted configuration. FIG. 6J is a cross-sectional view of the catheter 500 in FIG. 6I taken along line E-E. FIG. 6H shows the catheter 500 fully retracted after insertion. The catheter 500 may be inserted through a urethra and/or into a bladder to facilitate drainage of a bladder, as discussed herein. Aspects and components of the catheter 500 may be further discussed with regard to the other embodiments of this disclosure. In that sense, similar components are provided with reference numbers having the same last two digits throughout the present disclosure.

The sleeve 504 may be attached to the proximal member 506 at its proximal end 526. The sleeve 504 may invert or roll into the inner lumen of tubular member 502 over the proximal end opening of tubular member 502 and extend through the inner lumen of tubular member 502. The sleeve 504 may attach at its distal end 528 over a tubular extension 518 inside the housing 508. The sleeve 504 may extend over the tubular extension 518 to maintain patency of the sleeve 504. The catheter 500 may be provided to a user in a compact state where the tubular member 502 is received in the chamber 510 of the housing 508 in a stored configuration.

Once the user has engaged the catheter 500 with the urethra meatus, the user may advance the tubular member 502 by sliding a slider 550 through a slot 552 in the housing 508. The slider 550 may thus advance a portion of the sleeve 504 while a proximal portion 526 of the sleeve 504 is attached to the proximal member 506 and a distal portion 528 of the sleeve 504 is attached to the tubular extension 518. The sleeve 504 may be folded in the distal housing with a substantially 180 degree turn, which may be engaged by a hook or pulley-type member 560. The pulley-type member 560 may be connected to the slider 505 or be free floating and slide with the sleeve 504 along the longitudinal axis of the housing 508.

Once the catheter 500 reaches the bladder, the catheter 500 may void urine from the bladder. The urine may pass through the tubular member 502 and the sleeve 504, around the substantially 180 degree turn, and out of the sleeve 504. The urine may then pass through another substantially 180 degree turn, and though a channel 562 of the housing 508 and out of a distal end of the catheter 500.

On completion of voiding, the user may retract the slider 550 slider distally along the housing 508 to retract the tubular member 502 and the sleeve 504 back into the housing 508. The advancement/retraction rate of the tubular member 502 is the same as the advancement/retraction rate of the slider 550, facilitating insertion and removal of the tubular member 502 into the urethra and bladder. The tubular member 502 and the sleeve 504 is retained within the housing 508 before and after device use for easier and more hygienic handling, storage, and disposal.

Figure 7H:
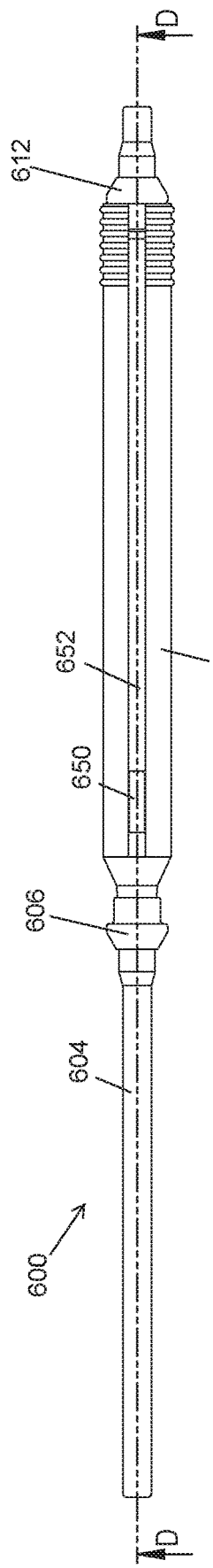
Figure 7I:
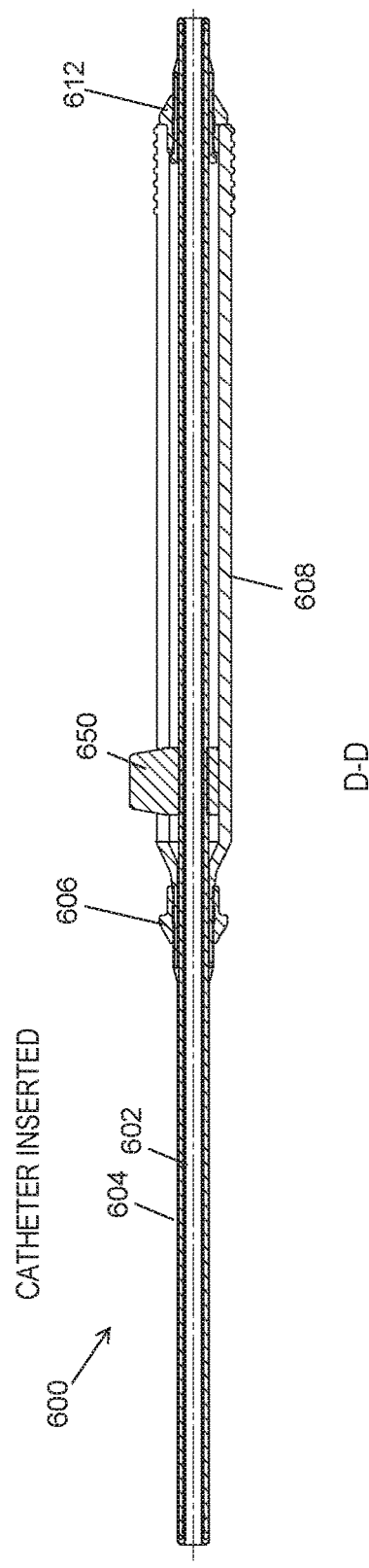

FIGS. 7A-I illustrate a sixth exemplary embodiment of a frictionless catheter 600 of the present invention, having a tubular member 602, a sleeve 604, a proximal member 606, and a housing member 608. FIGS. 7A-E show the catheter 600 in a ready-to-insert and retracted configuration. FIG. 7B is a cross-sectional view of the catheter 600 in FIG. 7A taken along line A-A. FIG. 7C is an enlarged view of the region B shown in FIG. 7B. FIG. 7D is an enlarged view of the region C shown in FIG. 7B. FIGS. 7F, 7H, and 7I show the catheter 600 in a fully inserted and everted configuration. FIG. 7I is a cross-sectional view of the catheter 600 in FIG. 7H taken along line D-D. FIG. 7G shows the catheter 600 fully retracted after insertion. The catheter 600 may be inserted through a urethra and/or into a bladder to facilitate drainage of a bladder, as discussed herein. Aspects and components of the catheter 600 may be further discussed with regard to the other embodiments of this disclosure. In that sense, similar components are provided with reference numbers having the same last two digits throughout the present disclosure.

The sleeve 604 may be attached to the proximal member 606 at its proximal end 626. The sleeve may evert or roll into the inner lumen of tubular member 602 over the proximal end opening of tubular member 602. The sleeve may extend through the inner lumen of tubular member 602 and attach at its distal end 628 to a distal portion 612 of the housing member 608. The housing member 608 may be profiled to favor device handling for self-insertion. A slider 650 may be configured to slide along a slot 652 in the housing member 608. The slider 650 may be configured to advance or retract the tubular member 602 relative to and within the housing member 608 by pushing an attachment portion 650A on the tubular member 602. The slider 650 may thus translate the tubular member 602 and the sleeve 604 in a conveyor-like manner. The tubular member 602 and the sleeve may translate between a distal configuration prior to insertion, and a proximal configuration to insert the catheter 600 into the urethra and/or bladder. The slider 650 may also retract the tubular member 602 and the sleeve 604 back to the distal configuration to remove the catheter 600 from the urethra and/or bladder. In the distal configuration, the tubular member 602 and sleeve 604 may extend distally from the housing 608. In the proximal configuration, the tubular member 602 and sleeve 604 may extend proximally from the housing 608. The catheter 600 may be used without a connected bag.

Figure 8E:
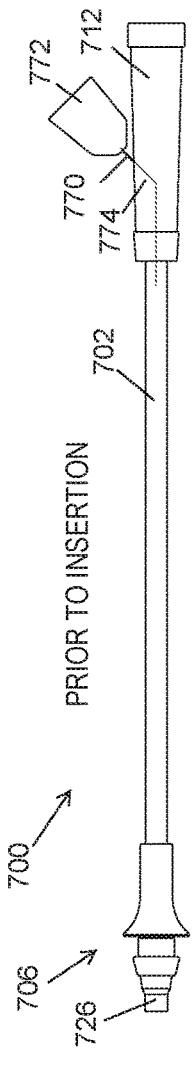
Figure 8F:
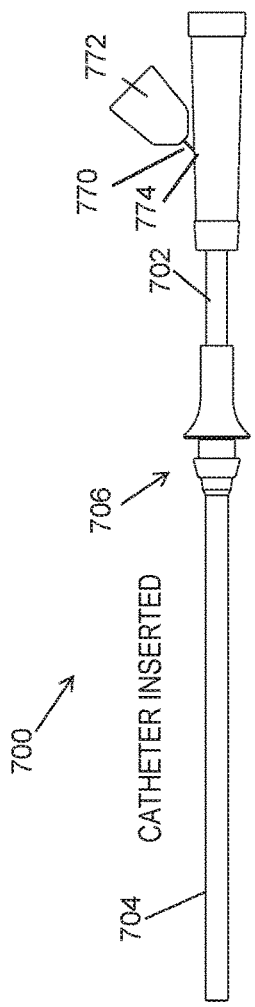
Figure 8G:
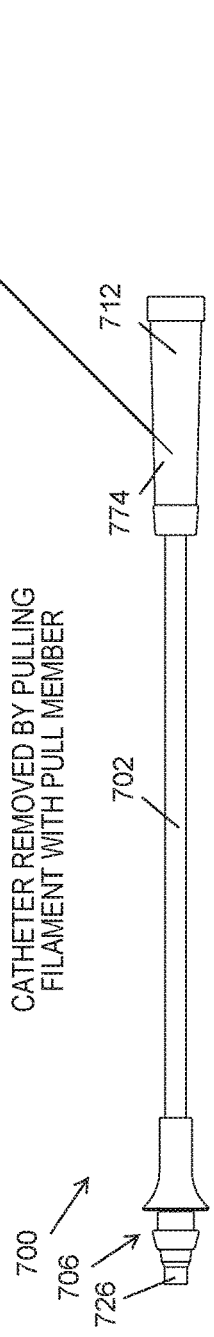

FIGS. 8A-K illustrate a seventh exemplary embodiment of a frictionless catheter 700 of the present invention, having a tubular member 702, a sleeve 704, a proximal member 706, and a distal member 712. FIGS. 8A-E show the catheter 700 in a ready-to-insert and retracted configuration. FIG. 8B is a cross-sectional view of the catheter 700 in FIG. 8A taken along line A-A. FIG. 8C is an enlarged view of the region B shown in FIG. 8B. FIG. 8D is an enlarged view of the region C shown in FIG. 8B. FIGS. 8F, 8H, and 8I show the catheter 700 in a fully inserted and everted configuration. FIG. 8I is a cross-sectional view of the catheter 700 in FIG. 8H taken along line D-D. FIGS. 8G, 8J, and 8K show the catheter 700 fully retracted after insertion. The catheter 700 may be inserted through a urethra and/or into a bladder to facilitate drainage of a bladder, as discussed herein. Aspects and components of the catheter 700 may be further discussed with regard to the other embodiments of this disclosure. In that sense, similar components are provided with reference numbers having the same last two digits throughout the present disclosure.

The catheter 700 may be provided to the user in the retracted configuration where the sleeve 704 substantially resides within the tubular member 702. The sleeve 704 may be attached to the proximal member 706 at its proximal end 726. The proximal end 726 may evert or roll over the proximal end opening of tubular member 702 and into the inner lumen of tubular member 702. The sleeve 704 may extend through the inner lumen of tubular member 702 and attach at its distal end 728 to a shuttle 718 which slides within the inner lumen of tubular member 702. The shuttle 718 may be a tubular member having a greater hoop strength than the sleeve 704 to maintain patency of the sleeve 704. The tubular member 702 has a low-profile to provide favorable handling, insertion, and drainage. Once the user engages the proximal member 706 with the urethra meatus, the user may advance the tubular member 702 into the urethra by pushing the catheter 700 and/or retracting the proximal member 706 which slides over the tubular member 702. The sleeve 704 everts over the tubular member 702 as the tubular member 702 advances through the urethra and/or bladder.

The catheter 700 may include a filament 770 which facilitates removal and/or retraction of the tubular member 702 upon completion of bladder voiding. The filament 770 may be attached to the shuttle 718 with an eyelet, a knot, an adhesive, and/or a weld. Retraction of the filament 770 may reverse the sleeve insertion mechanism, such that the tubular member 702 retracts from the urethra with no kinetic friction between the catheter 700 and urethra. The filament 770 may be attached at its distal end to a pull member 772, such as a pull tab, a pull flag, or a pull rod, to facilitate handling and pulling. The filament 770 may extend through an aperture 774 through a sidewall of the tubular member 702 or distal member 712 and out of the catheter 700, where the aperture 774 is proximal of the distal end of the catheter 700. The aperture 774 extending through the sidewall of the distal member 712 may be especially desirable due to an improved angle and minimizing interference with the insertion of the catheter 700. The filament 770 may be stored in a coiled configuration and housed in the distal member 712 and/or tubular member 702. In some embodiments, the filament 770 may be heat-set to make the filament 770 assume a particular form, such as a coil, or to have resilient and/or springy qualities in such particular form when the sleeve 704 is in the retraction configuration. The filament 770 lengthens and straightens as the sleeve 704 advances proximally through the tubular member 702 and everts over the outer surface of the tubular member 702 to the everted configuration. After voiding, the user may pull the pull member 772 to pull the filament 770 through the aperture 774 from outside of the catheter 700, which in turn pulls the shuttle 718 and sleeve 704 through the lumen of the tubular member 702 back to the retracted configuration.

The catheter 700 may be connected to a urine bag as the funnel section is not affected by the filament 770 or pull member 772. The aperture 774 may allow for pulling in a lateral or outward direction while still providing frictionless removal, facilitating the use of the catheter 700 with a bag or when a user is on a toilet. The catheter 700 also improves hygienic handling, storage, and disposability.

FIGS. 9A-I illustrate an eighth exemplary embodiment of a frictionless catheter 800 of the present invention, having a tubular member 802, a sleeve 804, a proximal member 806, and a distal member 812. FIGS. 9A-E show the catheter 800 in a ready-to-insert and retracted configuration. FIG. 9B is a cross-sectional view of the catheter 800 in FIG. 9A taken along line A-A. FIG. 9C is an enlarged view of the region B shown in FIG. 9B. FIG. 9D is an enlarged view of the region C shown in FIG. 9B. FIGS. 9F, 9H, and 9I show the catheter 800 in a fully inserted and everted configuration. FIG. 9I is a cross-sectional view of the catheter 800 in FIG. 9H taken along line D-D. FIG. 9G shows the catheter 800 fully retracted after insertion. The catheter 800 may be inserted through a urethra and/or into a bladder to facilitate drainage of a bladder, as discussed herein. Aspects and components of the catheter 800 may be further discussed with regard to the other embodiments of this disclosure. In that sense, similar components are provided with reference numbers having the same last two digits throughout the present disclosure.

The catheter 800 may be provided to the user in the retracted configuration where the sleeve 804 substantially resides within the tubular member 802. The sleeve 804 may be attached to the proximal member 806 at its proximal end 826. The proximal end 826 may evert or roll over the proximal end opening of tubular member 802 and into the inner lumen of tubular member 802. The sleeve 804 may extend through the inner lumen of the tubular member 802 and attach at its distal end 828 to a shuttle 818 which slides within the inner lumen of tubular member 802. Once the user has engaged the proximal member 806 with the urethra meatus, the user may advance the tubular member into the urethra by pushing the distal member 812 and/or retracting the proximal member 806 which slides over the tubular member 802. The sleeve 804 everts over the tubular member 802 as the tubular member 802 advances through the urethra and/or bladder.

The catheter 800 may further include a filament 870 which facilitates removal of the tubular member 802 upon completion of bladder voiding. The filament 870 may be attached to the shuttle 818 to which the distal end 828 of sleeve 804 is attached. The shuttle 818 may be a tubular member having a greater hoop strength than the sleeve 804 to maintain patency of the sleeve 804. The filament 870 may be attached to the shuttle 818 with an eyelet, a knot, an adhesive, and/or a weld. The tubular member 802 has a low-profile to provide favor handling, insertion, and drainage. Retraction of the shuttle 818 may reverse the sleeve insertion mechanism, such that the tubular member 802 retracts from the urethra with no kinetic friction between the catheter 800 and urethra.

A spring 880 may be connected to the filament 870 through a hook of the proximal end of the spring 880 and loop on a distal end of the filament 870. However, in some embodiments, the spring 880 may be connected directly to the shuttle 818 or the distal portion 828 of the sleeve 804, without any separate filament 870. The spring 880 may be housed in the tubular member 802 and/or distal member 812. The spring 880 may be a helical compression/extension filament and may be positioned along the longitudinal axis of the catheter 800. The spring 880 may extend when the sleeve 804 is pulled proximally as the catheter 800 is advanced through the urethra and/or bladder. The spring 880 may provide a restoration force and/or re-coil to the sleeve 804 when an insertion counterforce is removed, for example, when the catheter 800 is removed from the urinary meatus. The restoration force of the spring 880 may pull the sleeve 804, which retracts the sleeve 804 and the tubular member 802. The catheter 800 can be connected to a urine bag.

FIGS. 10A-I illustrate a ninth exemplary embodiment of a frictionless catheter 900 of the present invention, having a tubular member 902, a sleeve 904, a proximal member 906, and a distal member 912. FIGS. 10A-E show the catheter 900 in a ready-to-insert and retracted configuration. FIG. 10B is a cross-sectional view of the catheter 1100 in FIG. 10A taken along line A-A. FIG. 10C is an enlarged view of the region B shown in FIG. 10B. FIG. 10D is an enlarged view of the region C shown in FIG. 10B. FIGS. 10F, 10H, and 10I show the catheter 900 in a fully inserted and everted configuration. FIG. 10I is a cross-sectional view of the catheter 900 in FIG. 10H taken along line D-D. FIG. 10G shows the catheter 900 fully retracted after insertion. The catheter 900 may be inserted through a urethra and/or into a bladder to facilitate drainage of a bladder, as discussed herein. Aspects and components of the catheter 900 may be further discussed with regard to the other embodiments of this disclosure. In that sense, similar components are provided with reference numbers having the same last two digits throughout the present disclosure.

The catheter 900 may be provided to the user in the retracted configuration where the sleeve 904 substantially resides within the tubular member 902. The sleeve 904 may be attached to the proximal member 906 at its proximal end 926. The proximal end 926 may evert or roll over the proximal end opening of tubular member 902 and into the inner lumen of tubular member 902. The sleeve 904 may extend through the inner lumen of tubular member 902 and attach at its distal end 928 to a shuttle 918 which slides within the inner lumen of tubular member 902. The shuttle 918 may be a tubular member having a greater hoop strength than the sleeve 904 to maintain patency of the sleeve 904. The tubular member 902 has a low-profile to provide favor handling, insertion, and drainage. Once the user engages the proximal member 906 with the urethra meatus, the user may advance the tubular member into the urethra by pushing the catheter 900 and/or retracting the proximal member 906 which slides over the tubular member 902. The sleeve 904 everts over the tubular member 902 as the tubular member 902 advances through the urethra and/or bladder.

The catheter 900 may further include a filament 970 which facilitates removal of the tubular member 902 upon completion of bladder voiding. The filament 970 may be attached to the sliding shuttle 918 with an eyelet, a knot, an adhesive, and/or a weld. Retraction of the filament 970 may reverse the sleeve insertion mechanism, such that the tubular member 902 retracts from the urethra with no kinetic friction between the catheter 900 and urethra. The filament 970 may be attached to a spring 980 housed within the distal member 912. In another embodiment, the filament 970 may actually be just an extension of the spring 980 itself. The spring 980 may be a torsional spring (e.g., leaf spring) housed within an off-axis spring housing 982 of the distal member 912. The spring 980 may be attached to a spool which winds or coils the filament 970 around an axis, and the filament 970 may be pulled when the catheter 900 is advanced through the urethra and/or bladder. The spring 980 may recoil and provide a restoration force to the filament 970 when an insertion counterforce is removed, for example, when the catheter 900 is removed from the urinary meatus. The restoration force of the spring 980 may pull the filament 970, which retracts the sleeve 904 and the tubular member 902. The spring 980 may provide a constant, or approximately constant, spring force for retraction. The spool may retain and/or store the filament 970 when the sleeve 904 is in the retracted configuration. The catheter 900 can be connected to a urine bag as the funnel section is not affected by the filament 970 or the spring 980.

FIGS. 11A-T illustrate a tenth exemplary embodiment of a frictionless catheter 1000 of the present invention, having a tubular member 1002, a sleeve 1004, a proximal member 1006, and a distal member 1012. FIGS. 11A and 11E-H show the catheter 1000 in a ready-to-insert and retracted configuration. FIG. 11F is a cross-sectional view of the catheter 1000 in FIG. 11E taken along line A-A. FIG. 11G is an enlarged view of the region B shown in FIG. 11F. FIG. 11H is an enlarged view of the region C shown in FIG. 11F. FIGS. 11B and 11I-L show the catheter 1000 in a fully inserted and everted configuration. FIG. 11J is a cross-sectional view of the catheter 1000 in FIG. 11I taken along line D-D. FIG. 11K is an enlarged view of the region E shown in FIG. 11J. FIG. 11L is an enlarged view of the region F shown in FIG. 11J. FIGS. 11C-D and 11M-T show the catheter 1000 in a fully retracted configuration. FIG. 11N is a cross-sectional view of the catheter 1000 in FIG. 11M taken along line G-G. FIG. 11O is an enlarged view of the region H shown in FIG. 11N. FIG. 11P is an enlarged view of the region I shown in FIG. 11N. FIG. 11R is a cross-sectional view of the catheter 1000 in FIG. 11Q taken along line J-J. FIG. 11S is an enlarged view of the region K shown in FIG. 11R. FIG. 11T is an enlarged view of the region L shown in FIG. 11R. The catheter 1000 may be inserted through a urethra and/or into a bladder to facilitate drainage of a bladder, as discussed herein. Aspects and components of the catheter 1000 may be further discussed with regard to the other embodiments of this disclosure. In that sense, similar components are provided with reference numbers having the same last two digits throughout the present disclosure.

The catheter 1000 may be provided to the user in the retracted configuration where the sleeve 1004 substantially resides within the tubular member 1002. The sleeve 1004 may be attached to the proximal member 1006 at its proximal end 1026. The proximal end 1026 may evert or roll over the proximal end opening of tubular member 1002 and into the inner lumen of tubular member 1002. The sleeve 1004 may extend through the inner lumen of the tubular member 1002 and attach at its distal end 1028 to a shuttle 1018 which slides within the inner lumen of tubular member 1002. The shuttle 1018 may be a tubular member having a greater hoop strength than the sleeve 1004 to maintain patency of the sleeve 1004.

The catheter 1000 may further include a filament 1070 which facilitates removal of the tubular member 1002 upon completion of bladder voiding. Retraction of the filament 1070 may reverse the sleeve insertion mechanism, such that the tubular member 1002 retracts from the urethra with no kinetic friction between the catheter 1000 and urethra. A shuttle 1018 may be attached to a distal end portion 1028 of the sleeve 1004 and a distal portion of the filament 1070. The filament 1070 may be attached to the shuttle 1018 with an eyelet, a knot, an adhesive, and/or a weld. The filament 1070 may extend through an aperture 1074 through a sidewall of the tubular member 1002 or distal member 1012 and out of the catheter 1000, where the aperture 1074 is proximal of the distal end of the catheter 1000. The aperture 1074 extending through the sidewall of the distal member 1012 may be especially desirable due to an improved angle and minimizing interference with the insertion of the catheter 1000. The filament 1070 may be attached to a pull member 1072, which may embody a pull ring, to facilitate handling and pulling. Thus, the filament 1070 may extend from the shuttle 1018 through aperture 1074 and attached to the pull member 1072. A proximal portion of the filament 1070 may be stored in a coiled configuration and housed in the tubular member 1002 and/or distal member 1012. The filament 1070 may also be heat-set to make the filament 1070 take a particular form, such as a coil, or to have resilient and/or springy qualities to be biased into the particular form. The aperture 1074 may allow for pulling in an upward direction while still providing frictionless removal, facilitating the use of the catheter 1000 with a bag or when a user is on a toilet. The catheter 1000 can be connected to a urine bag as the funnel section is not affected by the filament 1070 or pull member 1072. The catheter 1000 also improves hygienic handling, storage, and disposability.

The pull member 1072 may include a securing member 1076 configured to releasably secure the pull member 1072 onto an outer surface of the tubular member 1002. The pull member 1072 may be secured onto the tubular member 1002 prior to insertion of the catheter 1000 and during insertion of the catheter 1000. The securing member 1076 may be in the form of a resilient clip configured to partially extend around the tubular member 1002. After voiding is complete, the securing member 1076 may be released from the tubular member 1002 and pulled to retract the sleeve 1004 and remove the catheter 1000, as illustrated in FIGS. 11M-P.

After removal of the catheter 1000, the pull member 1072 may be clipped back onto the tubular member 1102 and additionally locked to the proximal member 1006, as shown in FIGS. 11Q-S. For example, the pull member 1072 may include a locking or securing element 1072A such as an extension of the securing member 1076, which mates or locks into a complementary locking or securing element 1072B, such as a recess, on the proximal member 1006. The recess 1072B may secure the extension 1072A with a frictional and/or interference fit. The retention of the extension 1072A in the recess 1072B maintains tension on the filament 1070 to facilitate storage and/or disposal after use.

Figure 12A:
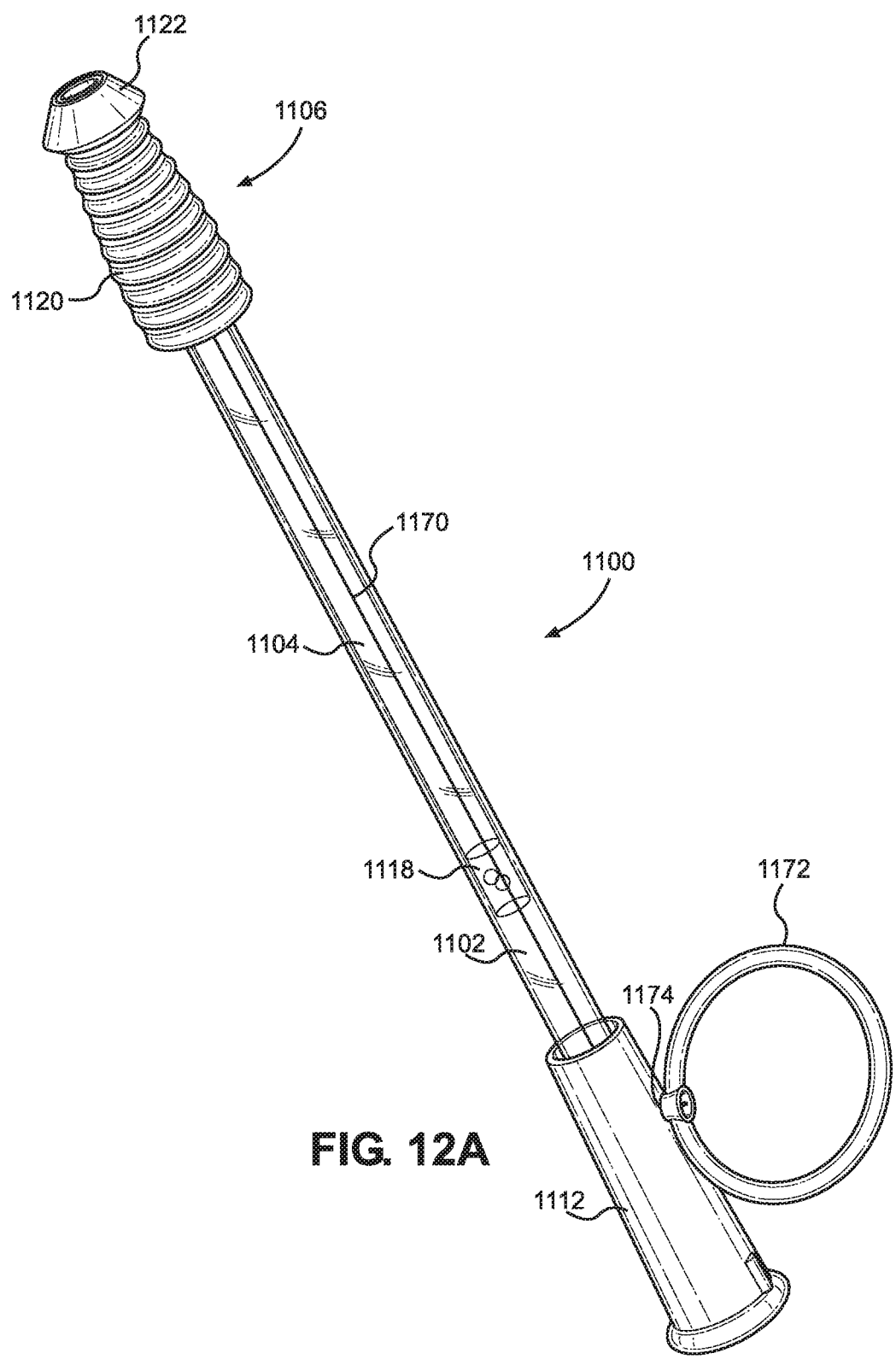
Figure 12B:
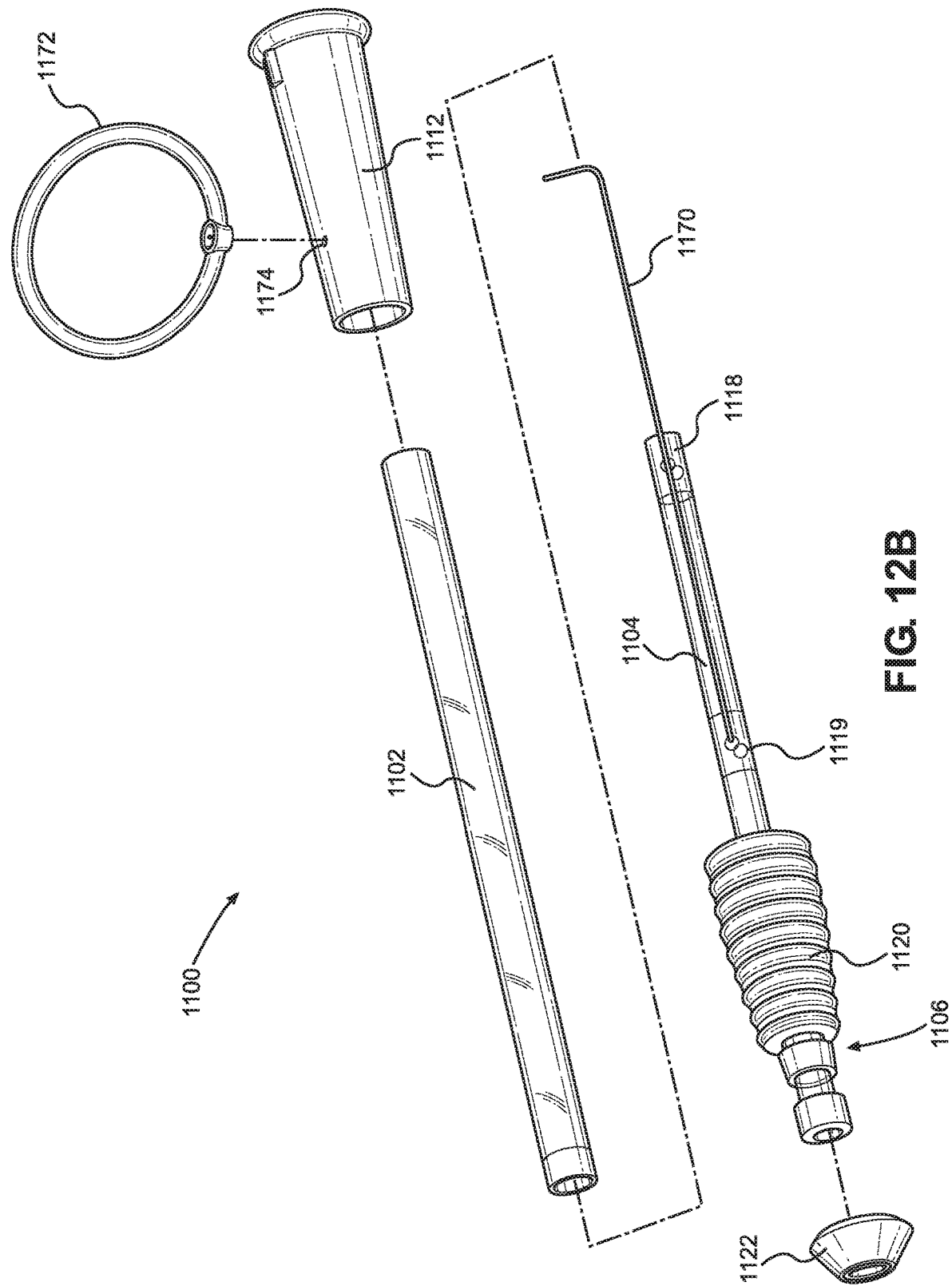
Figure 12E:
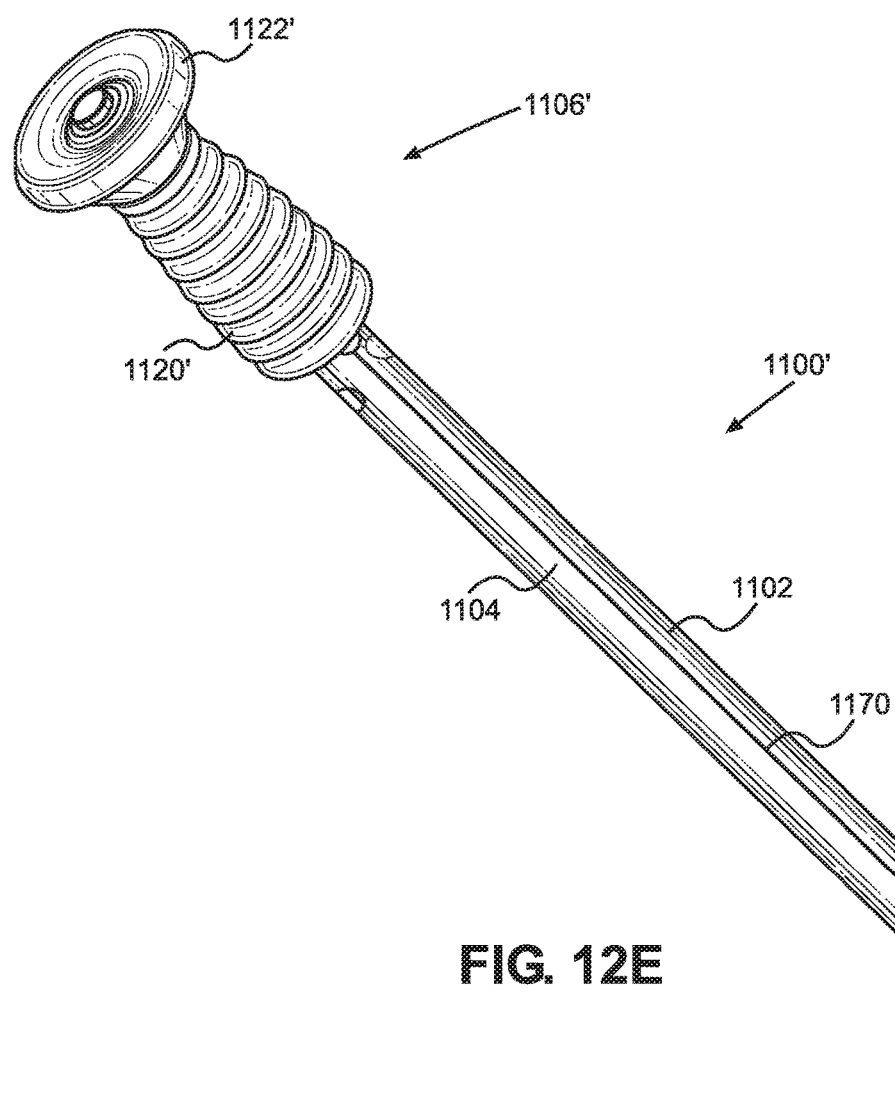
Figure 12F:
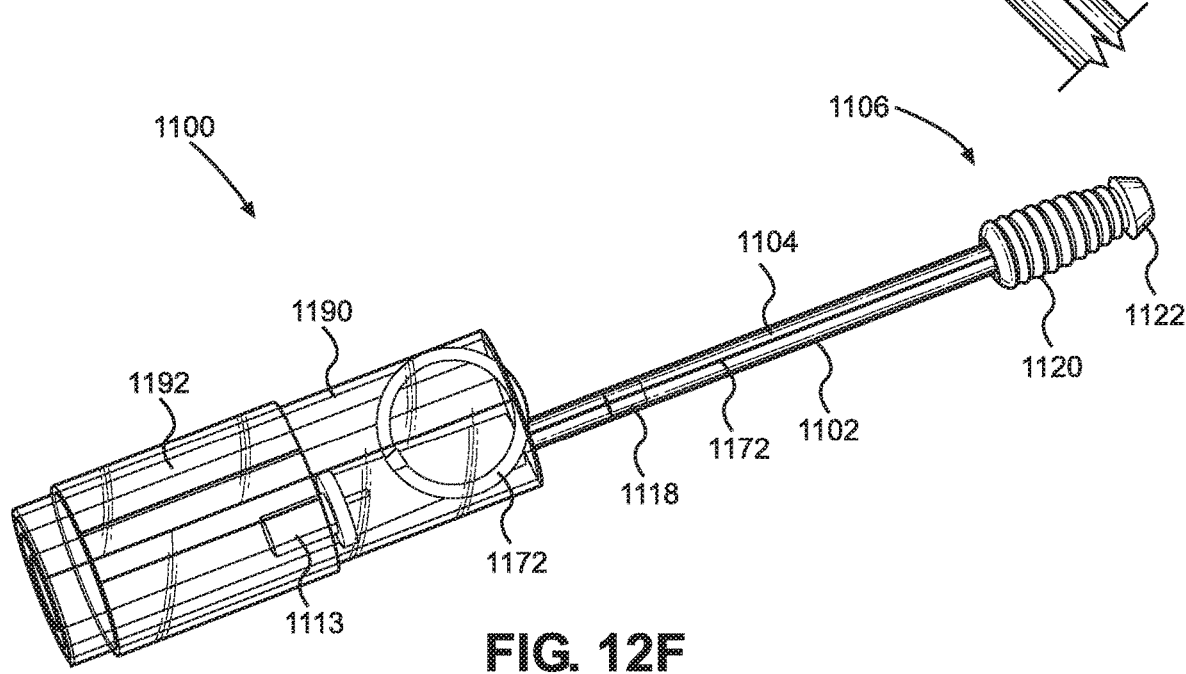

FIGS. 12A-F illustrate an eleventh exemplary embodiment of a catheter 1100 having a tubular member 1102, a sleeve 1104, a proximal member 1106, and a distal member 1112. FIGS. 12A-F show the catheter 1100 in a ready-to-insert and retracted configuration. FIG. 12A illustrates a perspective view of the catheter 1100. FIG. 12B illustrates an exploded view of the catheter 1100. FIG. 12C illustrates a frontal view of the catheter 1100. FIG. 12D illustrates a cross-sectional view of the catheter 1100 along the plane indicated in FIG. 12C. FIG. 12E illustrates the catheter 1100 having a proximal member 1106' for engaging male anatomy. FIG. 12F illustrates the catheter 1100 having a pre-attached bag 1190. The catheter 1100 may be inserted through a urethra and/or into a bladder to facilitate drainage of a bladder, as discussed herein. Aspects and components of the catheter 1100 may be further discussed with regard to the other embodiments of this disclosure. In that sense, similar components are provided with reference numbers having the same last two digits throughout the present disclosure.

The catheter 1100 may be provided to the user in the retracted configuration where the sleeve 1104 substantially resides within the tubular member 1102. The sleeve 1104 may be attached to the proximal member 1106 at its proximal end. The proximal end may evert or roll over the proximal end opening of tubular member 1102 and into the inner lumen of tubular member 1102. The sleeve 1104 may extend through the inner lumen of tubular member 1102 and may attach at its distal end to a first shuttle 1118. The first shuttle 1118 may be configured to slide through the inner lumen of tubular member 1102. The first shuttle 1118 may be a tubular member having a greater hoop strength than the sleeve 1104 to maintain patency of the sleeve 1104. The tubular member 1102 has a low-profile to provide favor handling, insertion, and drainage. Once the user engages the proximal member 1106 with the urethra meatus, the user may advance the tubular member 1102 into the urethra by pushing the catheter 1100 and/or retracting the proximal member 1106 which slides over the tubular member 1102. The sleeve 1104 everts over the tubular member 1102 as the tubular member 1102 advances through the urethra and/or bladder (as similarly illustrated in FIGS. 2A-D). The advancement of the sleeve 1104 may also advance the first shuttle 1118 through the tubular member 1102. In a fully advanced position of the sleeve 1104, the first shuttle 1118 may approximate and/or abut a second shuttle 1119 positioned in the lumen of the tubular member 1102 proximal of the first shuttle 1118.

The catheter 1100 may further include a filament 1170 having a pull member 1172, which facilitates removal of the tubular member 1102 upon completion of bladder voiding. The filament 1170 may extend from the pull member 1172 through an aperture 1174 through a sidewall of the tubular member 1102 or distal member 1112 and out of the catheter 1100, where the aperture 1174 is proximal of a distal end of the catheter 1100. The aperture 774 extending through the sidewall of the distal member 1112 may be especially desirable due to an improved angle and minimizing interference with the insertion of the catheter 1100. The filament 1170 may then extend proximally through the distal member 1112 and/or tubular member 1102. The filament 1170 may extend through and proximally past the first shuttle 1118. The filament 1170 may attach to the second shuttle 1119 proximal of the first shuttle 1118. The filament 1170 may be attached to the second shuttle 1119 with an eyelet, a knot, an adhesive, and/or a weld. Attachment of the filament 1170 to the second shuttle 1119 may maintain tension on the filament 1170 prior to insertion of the catheter 1100. Retraction of the filament 1170 may reverse the sleeve insertion mechanism, such that the tubular member 1102 retracts from the urethra with no kinetic friction between the catheter 1100 and urethra. Retraction of the filament 1170 may cause retraction of the second shuttle 1119, which contacts and pulls the first shuttle 1118 distally through the lumen of the tubular member 1102. The first shuttle 1118 may pull the sleeve 1104 into the lumen of the tubular member 1102 to the retracted configuration.

As illustrated in FIG. 12F, the catheter 1100 may be packaged with a pre-attached bag 1190 in fluid communication with the distal member 1112. As packaged, the bag 1190 may be wrapped around the distal member 1112 and secured in the wrapped configuration with an overlying sleeve 1192. Thus, after opening the package, the user may remove the overlying sleeve 1192 to unfold the bag 1190 prior to use. In embodiments with the bag 1190, the distal member 1112 may receive a tubular extension 1113 to provide improved fluid flow into the bag 1190. The tubular extension 1113 may be received in the lumen of the distal member 1112 through an interference or threaded fit. The bag 1190 may also receive the pull member 1172 in the wrapped configuration. As further discussed above the proximal member 1106 may include separable components including a tissue engaging member 1122 or 1122' and a handling portion 1120 or 1120'. The handling portion 1120 or 1120' may include one or more ribs and/or grooves, or the like to enhance grip of the user. The tissue engaging member 1122 may include a convex proximal surface to engage female anatomy. Alternatively, the tissue engaging member 1122' may include a concave proximal surface to engage male anatomy.

Figure 13A:
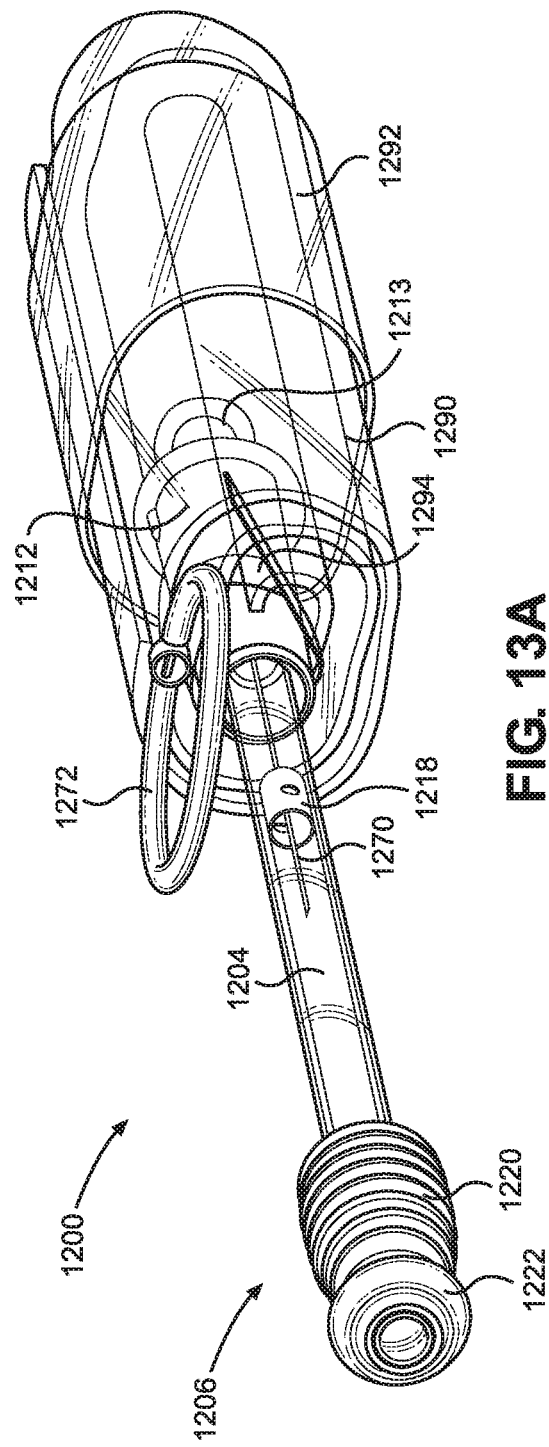
FIGS. 13A-D illustrate a twelfth exemplary embodiment of a catheter of the present invention.
Figure 13B:
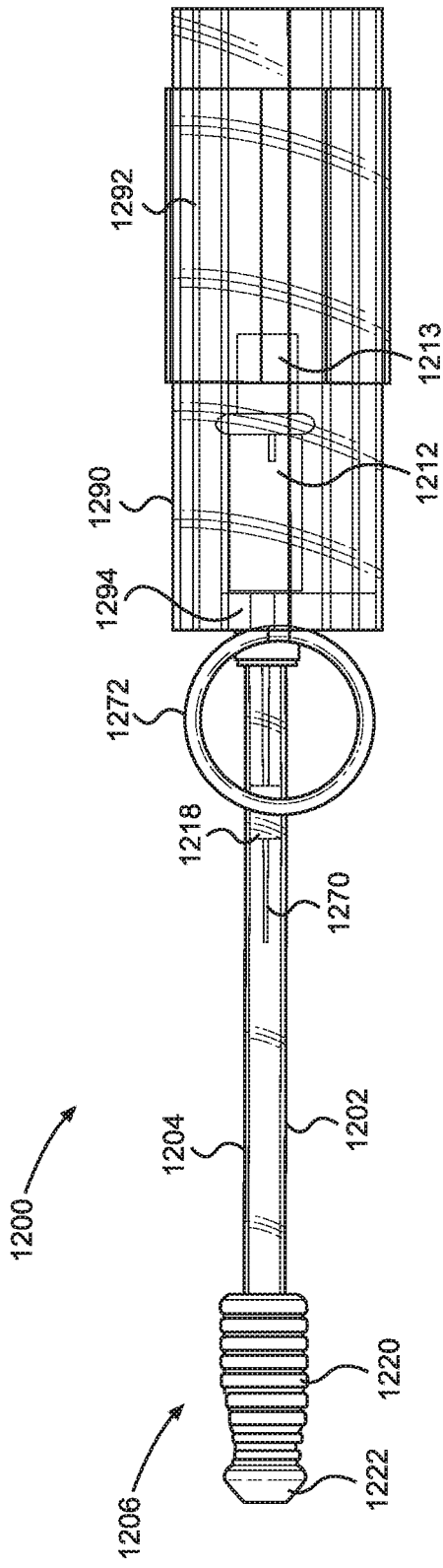
Figure 13C:
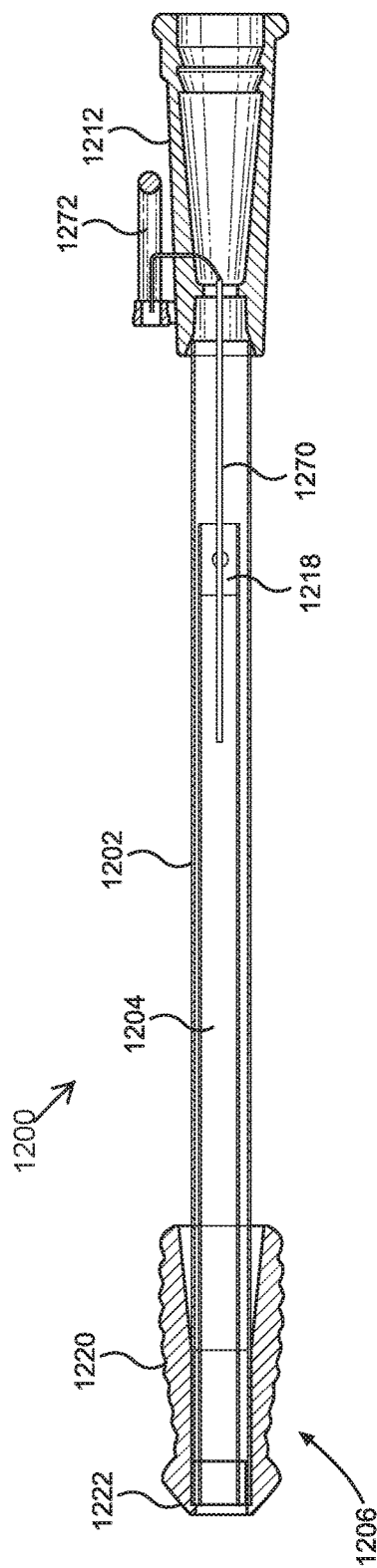
Figure 13D:
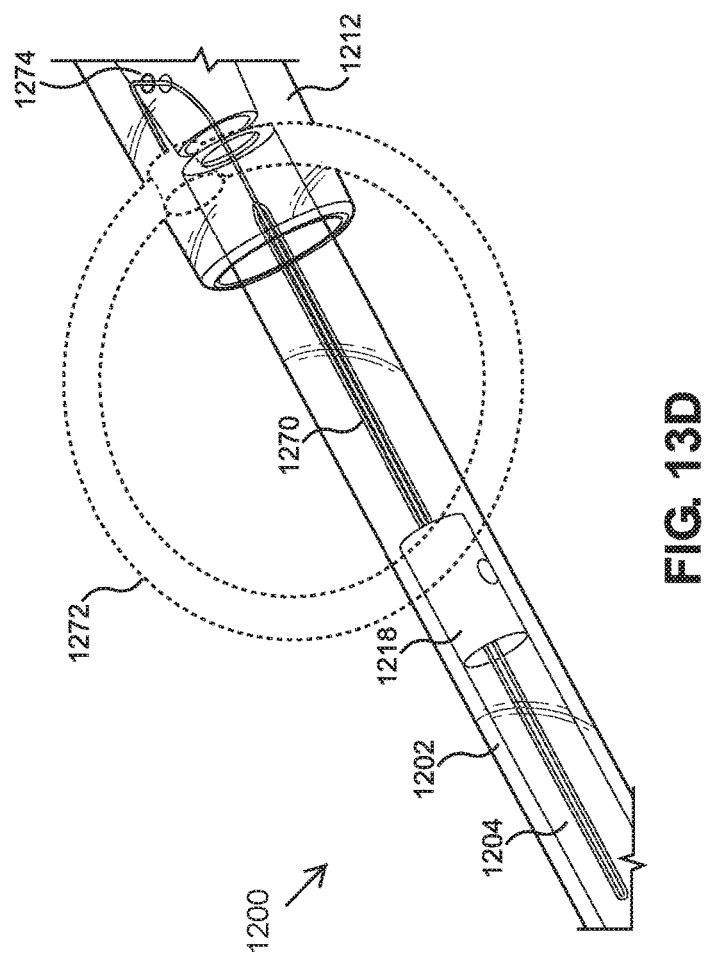

FIGS. 13A-D illustrate a twelfth exemplary embodiment of a catheter 1200 having a tubular member 1202, a sleeve 1204, a proximal member 1206, and a distal member 1212. FIGS. 13A-D show the catheter 1200 in a ready-to-insert and retracted configuration. FIG. 13A illustrates a perspective view of the catheter 1200. FIG. 13B illustrates a top view of the catheter 1200. FIG. 13C illustrates a side cross-sectional view of the catheter 1200. FIG. 13D illustrates a close-up view of a filament 1270. The catheter 1200 may be inserted through a urethra and/or into a bladder to facilitate drainage of a bladder, as discussed herein. Aspects and components of the catheter 1200 may be further discussed with regard to the other embodiments of this disclosure. In that sense, similar components are provided with reference numbers having the same last two digits throughout the present disclosure.

The catheter 1200 may be provided to the user in a retracted configuration where the sleeve 1204 substantially resides within the tubular member 1202. The sleeve 1204 may be attached to the proximal member 1206 at its proximal end. The proximal end may evert or roll over the proximal end opening of tubular member 1202 and into the inner lumen of tubular member 1202. The sleeve 1204 may extend through the inner lumen of tubular member 1202 and attach at its distal end to a shuttle 1218. The shuttle 1218 may be configured to slide within the inner lumen of tubular member 1202. The shuttle 1218 may be a tubular member having a greater hoop strength than the sleeve 1204 to maintain patency of the sleeve 1204. The filament 1270 may be attached to the shuttle 1218 with an eyelet, a knot, an adhesive, and/or a weld. The tubular member 1202 has a low-profile to provide favor handling, insertion, and drainage. Once the user engages the proximal member 1206 with the urethra meatus, the user may advance the tubular member into the urethra by pushing the catheter 1200 and/or retracting the proximal member 1206 which slides over the tubular member 1202. The sleeve 1204 everts over the tubular member 1202 as the tubular member 1202 advances through the urethra and/or bladder (as similarly illustrated in FIGS. 2A-D). The advancement of the sleeve 1204 may also advance the shuttle 1218 through the tubular member 1202.

The filament 1270 may have a pull member 1272, which facilitates removal of the tubular member 1202 upon completion of bladder voiding. The filament 1270 may be attached to the shuttle 1218 to which the distal end of sleeve 1204 is attached. In the ready-to-use and retracted configuration of the catheter 1200, the filament 1270 may be longitudinally looped and/or bunched in the lumen of the catheter 1200. As illustrated in FIG. 13D, the filament 1270 may extend from the pull member 1272 through an aperture 1274 through a sidewall of the distal member 1212 or tubular member 1202 and out of the catheter 1200, where the aperture 1274 is proximal of a distal end of the catheter 1200. The aperture 1274 extending through the sidewall of the distal member 1212 may be especially desirable due to an improved angle and minimizing interference with the insertion of the catheter 1200. The filament 1270 may then extend proximally through the distal member 1212 and/or tubular member 1202. The filament 1270 may extend proximally past and through the shuttle 1218. The filament 1270 may then make a first 180° turn distally. The filament 1270 may extend distally past and through the shuttle 1218. The filament 1270 may then make a second 180° turn proximally. The filament 1270 may then extend proximally, and rigidly connect to the shuttle 1218. However, the filament 1270 may be longitudinally looped and/or bunched with a single 180° turn. The looping and/or bunching of the filament 1270 may ensure storage and sterility of the filament in the catheter 1200. During insertion of the catheter 1200, the filament 1270 may straighten as the sleeve 1204 everts and extends over the outer surface of the tubular member 1202. After voiding of the bladder, the user may retract/pull the filament 1270 to reverse the sleeve insertion mechanism, such that the tubular member 1202 retracts from the urethra with no kinetic friction between the catheter 1200 and urethra. Retraction of the filament 1270 may pull the shuttle 1218 distally through the lumen of the tubular member 1202. The shuttle 1218 may pull the sleeve 1204 through the lumen of the tubular member 1202 to the retracted configuration.

As illustrated in FIG. 13A-B, the catheter 1200 may be packaged with a pre-attached bag 1290 in fluid communication with the distal member 1212. As packaged, the bag 1290 may be wrapped around the distal member 1212 and secured in the wrapped configuration with an overlying sleeve 1292. Thus, after opening the package, the user may remove the overlying sleeve 1292 to unfold the bag 1290 prior to use. In embodiments with the bag 1290, the distal member 1212 may receive a tubular extension 1213 to provide improved fluid flow into the bag 1290. The tubular extension 1213 may be received in the lumen of the distal member 1212 through an interference or threaded fit. A support member 1294 may be disposed inside the bag 1290 to prop the pull member 1272 into a proximal configuration outside of the bag 1290. The support member 1294 may be a sleeve or wrap disposed around the distal member 1212 to abut the distal side of the pull member 1272. As further discussed above, the proximal member 1206 may include separable components including a tissue engaging member 1222 and a handling portion 1220. The handling portion 1220 may include one or more ribs and/or grooves, or the like to enhance grip of the user. The tissue engaging member 1222 may include a convex proximal surface to engage female anatomy. Alternatively, the tissue engaging member may include a concave proximal surface to engage male anatomy.

Figure 14A:
FIGS. 14A-C illustrate various configurations of a proximal portion of any of the catheters disclosed herein.
Figure 14B:
Figure 14C:

FIGS. 14A-C show various configurations of a proximal portion of any of the tubular members disclosed herein, including tubular members 102, 202, 302, 402, 502, 602,

702, 802, 902, 1002, 1102, and 1202, having features that render the proximal portion of such tubular member relatively more flexible than the rest of the tubular member. Such features may include a pattern of holes. As one set of examples, shown in FIGS. 14A and 14C, the holes are formed on four lines, one each on four sides of the tube, with a first line pair of holes, with one line each on two opposing sides that are longitudinally aligned and facing each other, and a second line of a pair of holes, with one line each on two other opposing sides that are longitudinally aligned and facing each other, but first line pair and second line pair are offset longitudinally relative to each other by a distance of one spacing between holes in a line. In the example shown in FIG. 14A, the holes can be oval or elliptical in shape, while in the example shown in FIG. 14C, the holes can be circular. In the example shown in FIG. 14B, a score line or cut in the wall of the tube is in a spiral pattern, with the pitch of the spiral being variable and becoming tighter, or lower, as the spiral progresses towards the tip of the tube. When the proximal portion of the tube is more flexible, it allows for easier insertion through the urethra, especially in cases where the path of travel is curved or tortuous. However, the various configurations shown in FIGS. 14A-C can be used anywhere along the catheter tubes as disclosed herein, so as to render a particular length of tubing more or less flexible. Advantageously, the use of the various patterns shown in FIGS. 14A-C in a tubular member such as tubular members 102, 202, 302, 402, 502, 602, 702, 802, 902, 1002, 1102, and 1202 with an external sleeve such as sleeve 104, 204, 304, 404, 504, 604, 704, 804, 904, 1004, 1104, and 1204 facilitates folding or bending of the assembly yet still will carry fluid flow down the catheter lumen due to the presence of the sleeve.

The catheters of the present disclosure and various embodiments of the catheters 100, 200, 300, 400, 500, 600, 700, 800, 900, 1000, 1100, and 1200 may be made from a variety of materials. Advantageously, it has been discovered that the sleeve 104, 204, 304, 404, 504, 604, 704, 804, 904, 1004, 1104, and 1204 can be made of a high density polyethylene film, while the tubular member 102, 202, 302, 402, 502, 602, 702, 802, 902, 1002, 1102, and 1202 can be made of polyvinyl chloride (PVC), the combination of which will produce superior performance in terms of low internal friction within the catheter system, with associated benefits in terms of lower cost relative to other materials. The sleeves 104, 204, 304, 404, 504, 604, 704, 804, 904, 1004, 1104, and 1204 may be dry and uncoated to reduce the risk of contamination. The filaments 770, 870, 970, 1070, 1170, and 1270 may be made of plastic or metal and embody a braided or woven string or a monofilament. Each of the catheters 100, 200, 300, 400, 500, 600, 700, 800, 900, 1000, 1100, and 1200 may include a proximal end portion for engagement with female anatomy (e.g., 1106 illustrated in FIGS. 13A-D) or a proximal end portion for engagement with male anatomy (e.g., 1106' illustrated in FIG. 12E). Each of the catheters 100, 200, 300, 400, 500, 600, 700, 800, 900, 1000, 1100, and 1200 may be packaged with a pre-attached bag (e.g., 1190 or 1290 as illustrated in FIGS. 12F, 13A-B) to collect urine, or packaged without a pre-attached bag (e.g. illustrated in FIG. 12A, 13C) to drain urine directly into a bathroom receptacle. The catheters 100, 200, 300, 400, 500, 600, 700, 800, 900, 1000, 1100, and 1200 are primarily discussed herein as being inserted through a urethra and/or into a bladder to facilitate drainage of a bladder. However, it is also contemplated that the catheter 100 may be used in vascular procedures, as an introduction aid, and/or for any number of other applications.

The many features and advantages of the frictionless catheter described herein are apparent from the detailed specification, and thus, the claims cover all such features and advantages within the scope of this application. further, numerous modifications and variations are possible. As such, it is not desired to limit the frictionless catheter to the exact construction and operation described and illustrated and, accordingly, all suitable modifications and equivalents may fall within the scope of the claims.

The invention claimed is:

1. A catheter comprising:
    a tubular member having a lumen and an outer surface;
    a sleeve configured to be positioned in the lumen of the tubular member in a retracted configuration and to evert over at least a portion of the outer surface of the tubular member in an everted configuration;
    a filament configured to retract the sleeve into the retracted configuration; and
    an aperture proximal of a distal end of the catheter, wherein the filament extends from the lumen through the aperture and out of the catheter.

2. The catheter of claim 1, further comprising a distal member having a distal opening, wherein the aperture extends through the distal member or the tubular member.

3. The catheter of claim 2, wherein the distal member comprises a funnel.

4. The catheter of claim 1, further comprising a pull member on a distal end of the filament.

5. The catheter of claim 4, wherein the pull member comprises a pull ring or a pull tab.

6. The catheter of claim 1, the filament is looped, coiled, and/or bunched in the catheter when the sleeve is in the retracted configuration, and the filament lengthens or straightens as the sleeve everts.

7. The catheter of claim 1, further comprising a shuttle attached to a distal end of the sleeve, wherein the shuttle comprises a tubular member configured to maintain patency of the sleeve, and the filament engages the shuttle to retract the sleeve into the lumen.

8. The catheter of claim 7, wherein the filament extends proximally past the shuttle in the retracted configuration.

9. The catheter of claim 7, wherein the filament is attached to the shuttle.

10. The catheter of claim 7, further comprising a second shuttle proximal of the shuttle, wherein the filament is attached to the second shuttle, and retraction of the filament causes the second shuttle to abut the shuttle and retract the sleeve.

11. The catheter of claim 1, wherein the tubular member comprises at least one cut or hole extending through a proximal portion of the tubular member to increase flexibility of the proximal portion.

12. The catheter of claim 11, wherein the at least one cut or hole extends along less than half of a length of the tubular member.

13. The catheter of claim 11, wherein the at least one cut or hole varies along a length of the proximal portion to provide variable flexibility.

14. The catheter of claim 1, further comprising a proximal member secured to a proximal portion of the sleeve, wherein the proximal member is configured to slide over at least a portion of the tubular member to evert the sleeve over the tubular member.

15. The catheter of claim 1, further comprising a bag positioned distal of the tubular member.

16. A method of draining a volume of fluid, the method comprising:

receiving the catheter of claim 1;

inserting the tubular member into a bodily lumen;

everting the sleeve over the outer surface of the tubular member from the lumen of the tubular member; and pulling the filament to pull the sleeve through the lumen to remove the tubular member from the bodily lumen.

17. The method of claim 16, wherein when receiving the catheter, the filament is looped, coiled, and/or bunched in the lumen of the catheter, and the filament lengthens or straightens as the sleeve everts.

18. The method of claim 16, wherein pulling the filament includes pulling the filament through the aperture of the catheter.

19. The method of claim 16, wherein pulling the filament includes pulling a pull tab or a pull ring attached to a distal end of the filament.

20. The method of claim 16, further comprising sliding a proximal member secured to a proximal end of the sleeve to evert the sleeve over the outer surface.

21. A catheter comprising:

a tubular member having a lumen and an outer surface;

a sleeve configured to be positioned in the lumen of the tubular member in a retracted configuration and to evert over at least a portion of the outer surface of the tubular member in an everted configuration; and a chamber configured to receive a distal portion of the sleeve in the retracted configuration, wherein the sleeve is longitudinally compressed in the chamber in the retracted configuration.

22. The catheter of claim 21, further comprising a distal housing enclosing the chamber, wherein the distal housing has a diameter larger than the tubular member.

23. The catheter of claim 22, wherein the distal housing comprises:

a distal member secured to a distal portion of the sleeve; and a chamber member enclosing the chamber, wherein the distal member is configured to separate from the chamber member to pull the sleeve distally through the lumen of the tubular member.

24. The catheter of claim 23, wherein the distal portion of the sleeve extends between the distal member and the chamber member.

25. The catheter of claim 21, further comprising a proximal member secured to a proximal portion of the sleeve, the proximal member being configured to slide over at least a portion of the tubular member to evert the sleeve over the outer surface.

26. The catheter of claim 21, wherein the distal portion of the sleeve is folded and/or pleated in the chamber in the retracted configuration.

\* \* \* \* \*